US012714564B2

(12) United States Patent
Hiorth et al.

(10) Patent No.: US 12,714,564 B2
(45) Date of Patent: Aug. 25, 2026

(54) DEVICE FOR HEART REPAIR

(71) Applicant: CARDIOMECH AS, Trondheim (NO)

(72) Inventors: Nikolai Hiorth, Oslo (NO); Hans Emil Hiorth, Trondheim (NO)

(73) Assignee: CardioMech AS, Trondheim (NO)

( * ) Notice: Subject to any disclaimer, the term of this patent is extended or adjusted under 35 U.S.C. 154(b) by 1124 days.

(21) Appl. No.: 17/298,065

(22) PCT Filed: Nov. 29, 2019

(86) PCT No.: PCT/EP2019/083170
§ 371 (c)(1),
(2) Date: May 28, 2021

(87) PCT Pub. No.: WO2020/109599
PCT Pub. Date: Jun. 4, 2020

(65) Prior Publication Data

US 2022/0117734 A1 Apr. 21, 2022

(30) Foreign Application Priority Data

Nov. 29, 2018 (GB) ..................................... 1819480
Nov. 29, 2018 (GB) ..................................... 1819484
(Continued)

(51) Int. Cl.
*A61F 2/24* (2006.01)
*A61B 17/04* (2006.01)
(Continued)

(52) U.S. Cl.
CPC ........ *A61F 2/2466* (2013.01); *A61B 17/0401* (2013.01); *A61B 17/0467* (2013.01);
(Continued)

(58) Field of Classification Search
CPC .................. A61F 2/2466; A61F 2/2457; A61F 2220/0016; A61F 2002/9534; A61F 2/24;
(Continued)

(56) References Cited

U.S. PATENT DOCUMENTS 854,551 A 5/1907 Allen
4,741,330 A 5/1988 Hayhurst
(Continued)

FOREIGN PATENT DOCUMENTS

AU 2012261998 3/2017
CA 2920384 2/2015
(Continued)

OTHER PUBLICATIONS

Office Action issued in corresponding Chinese Application No. 201980089994.X, dated Jan. 13, 2024 (English Translation provided).
(Continued)

*Primary Examiner* — Yashita Sharma
*Assistant Examiner* — Kia Xiong White
(74) *Attorney, Agent, or Firm* — Norton Rose Fulbright US LLP

(57) ABSTRACT

A catheter device is described. The device is for implanting a leaflet anchor (10) into the heart as part of a procedure for implanting an artificial chordae line (14). The catheter device comprises: a leaflet anchor (10) for attachment to the leaflet (12) of the heart; and a leaflet anchor deployment mechanism (6), (30), (38) for deploying the leaflet anchor (10). The leaflet anchor deployment mechanism (6), (30), (38) allows for retraction and repositioning of the leaflet anchor (10) after deployment of the anchor (10) into the leaflet (12) via an ejector unit (36) having a grasping device (50) with a first configuration arranged to permit deployment of the leaflet anchor (10) into the leaflet (12) without
(Continued)

disengagement of the leaflet anchor (10) from the ejector unit (34), and a second configuration in which the leaflet anchor (10) is reversibly released from the ejector unit (36). In the first configuration the grasping device (50) of the ejector unit (36) grasps a proximal end of the leaflet anchor (10), whilst a distal end of the leaflet anchor (10) is unimpeded by the grasping device (50) to enable it to be implanted in the leaflet (12). In the second configuration the grasping device (50) is disengaged from the leaflet anchor (10).

26 Claims, 32 Drawing Sheets

(30) Foreign Application Priority Data

Nov. 29, 2018 (GB) ..................................... 1819489
Nov. 29, 2018 (GB) ..................................... 1819490
Dec. 12, 2018 (GB) ..................................... 1820258
Dec. 21, 2018 (GB) ..................................... 1820990
Apr. 3, 2019 (GB) ..................................... 1904688
May 20, 2019 (GB) ..................................... 1907110
Aug. 16, 2019 (GB) ..................................... 1911812
Aug. 16, 2019 (GB) ..................................... 1911817
Sep. 10, 2019 (GB) ..................................... 1913057
Sep. 16, 2019 (GB) ..................................... 1913360

(51) Int. Cl.
*A61B 17/00* (2006.01)
*A61B 17/29* (2006.01)
*A61B 90/00* (2016.01)

(52) U.S. Cl.
CPC ........ *A61B 17/0469* (2013.01); *A61F 2/2457* (2013.01); *A61F 2/2463* (2013.01); *A61B 2017/00243* (2013.01); *A61B 2017/00477* (2013.01); *A61B 2017/00526* (2013.01); *A61B 2017/00884* (2013.01); *A61B 2017/0403* (2013.01); *A61B 2017/0409* (2013.01); *A61B 2017/0417* (2013.01); *A61B 2017/0437* (2013.01); *A61B 2017/0448* (2013.01); *A61B 2017/0459* (2013.01); *A61B 2017/0464* (2013.01); *A61B 17/29* (2013.01); *A61B 2017/2947* (2013.01); *A61B 2090/0811* (2016.02); *A61F 2220/0016* (2013.01); *A61F 2220/0075* (2013.01); *A61F 2230/0013* (2013.01); *A61F 2240/00* (2013.01); *A61F 2240/001* (2013.01)

(58) Field of Classification Search
CPC ............ A61B 17/0401; A61B 17/0469; A61B 2017/0459; A61B 2017/044; A61B 2017/0441; A61B 2017/0411; A61B 2017/0416
See application file for complete search history.

(56) References Cited

U.S. PATENT DOCUMENTS 5,330,442 A 7/1994 Green et al.
5,336,239 A 8/1994 Gimpelson
5,891,160 A 4/1999 Williamson et al.
6,099,553 A 8/2000 Hart et al.
6,217,565 B1 4/2001 Cohen
6,231,561 B1 5/2001 Frazier et al.
6,626,930 B1 9/2003 Allen et al.
6,743,239 B1 6/2004 Kuehn et al.
7,316,706 B2 1/2008 Bloom et al.
7,632,308 B2 12/2009 Loulmet
7,635,386 B1 12/2009 Gammie
7,740,638 B2 6/2010 Hyde
7,780,701 B1 8/2010 Meridew et al.
7,992,567 B2 8/2011 Hirotsuka et al.
8,096,985 B2 1/2012 Legaspi et al.
8,186,355 B2 5/2012 Van Der Burg et al.
8,292,884 B2 10/2012 Levine et al.
8,333,204 B2 12/2012 Saadat
8,500,800 B2 8/2013 Maisano et al.
8,545,551 B2 10/2013 Loulmet
8,690,939 B2 4/2014 Miller et al.
D708,744 S 7/2014 Morris et al.
8,778,016 B2 7/2014 Janovsky et al.
8,784,439 B1 7/2014 Ward et al.
8,790,394 B2 7/2014 Miller et al.
8,900,295 B2 12/2014 Migliazza et al.
9,039,759 B2 5/2015 Alkhatib et al.
9,131,928 B2 9/2015 Zlotnick et al.
9,138,316 B2 9/2015 Bielefeld
9,204,964 B2 12/2015 Dahlgren et al.
9,204,965 B2 12/2015 Longoria
9,226,825 B2 1/2016 Starksen et al.
9,248,018 B2 2/2016 Chawla
9,301,842 B2 4/2016 Bielefeld
9,452,048 B2 9/2016 O'Beirne et al.
9,474,605 B2 10/2016 Rowe et al.
9,486,315 B2 11/2016 Chawla
9,545,309 B2 1/2017 Alkhatib et al.
9,572,667 B2 * 2/2017 Solem .................. A61F 2/0077
9,622,861 B2 4/2017 Miller et al.
9,668,860 B2 6/2017 Kudlik et al.
9,700,412 B2 7/2017 Yaron et al.
9,730,793 B2 8/2017 Reich et al.
9,744,038 B2 8/2017 Dahlgren et al.
9,795,482 B2 10/2017 Duffy et al.
9,877,833 B1 1/2018 Bishop et al.
10,159,571 B2 12/2018 De Canniere et al.
10,213,303 B2 2/2019 Medema et al.
10,226,339 B2 3/2019 Spence et al.
10,271,947 B2 4/2019 Alkhatib
10,285,686 B2 5/2019 Gammie et al.
10,376,673 B2 8/2019 Van Hoven et al.
10,405,979 B2 9/2019 Schaffner et al.
10,433,831 B2 10/2019 Sauer
2002/0183787 A1 12/2002 Wahr et al.
2003/0078465 A1 4/2003 Pai et al.
2003/0145865 A1 8/2003 Sterman et al.
2003/0216613 A1 11/2003 Suzuki et al.
2004/0003819 A1 1/2004 St. Goar et al.
2004/0078054 A1 4/2004 Biggs et al.
2004/0102809 A1 5/2004 Anderson
2004/0153049 A1 8/2004 Hewitt et al.
2004/0186566 A1 9/2004 Hindriches et al.
2004/0260317 A1 12/2004 Bloom et al.
2004/0260344 A1 12/2004 Lyons et al.
2005/0228413 A1 10/2005 Binmoeller et al.
2005/0251208 A1 11/2005 Elmer et al.
2006/0089711 A1 4/2006 Dolan et al.
2006/0142784 A1 6/2006 Kontos
2006/0207607 A1 9/2006 Hirotsuka et al.
2006/0287716 A1 12/2006 Banbury et al.
2006/0293698 A1 12/2006 Douk
2006/0293710 A1 12/2006 Foerster et al.
2007/0049952 A1 3/2007 Weiss
2007/0049970 A1 3/2007 Belef et al.
2007/0083235 A1 4/2007 Jervis et al.
2007/0118151 A1 5/2007 Davidson
2007/0144539 A1 6/2007 van der Burg et al.
2007/0270943 A1 11/2007 Solem
2008/0009888 A1 1/2008 Ewers et al.
2008/0027560 A1 1/2008 Jackson et al.
2008/0051807 A1 2/2008 St. Goar et al.
2008/0161762 A1 7/2008 Stehr et al.
2008/0188873 A1 8/2008 Speziali
2008/0195126 A1 * 8/2008 Solem .................. A61F 2/2457
606/155
2008/0228223 A1 9/2008 Alkhatib

(56) References Cited

U.S. PATENT DOCUMENTS

| | | | | |
|---|---|---|---|---|
| 2008/0243150 | A1 | 10/2008 | Starksen et al. | |
| 2009/0163934 | A1 | 6/2009 | Raschdorf et al. | |
| 2009/0287304 | A1 | 11/2009 | Dahlgren et al. | |
| 2010/0016958 | A1 | 1/2010 | St. Goar et al. | |
| 2010/0022823 | A1 | 1/2010 | Goldfarb et al. | |
| 2010/0042147 | A1 | 2/2010 | Janovsky et al. | |
| 2010/0145362 | A1 | 6/2010 | McLawhorn et al. | |
| 2010/0161042 | A1* | 6/2010 | Maisano | A61F 2/2457 623/2.11 |
| 2010/0217283 | A1 | 8/2010 | St. Goar et al. | |
| 2010/0280603 | A1 | 11/2010 | Maisano et al. | |
| 2011/0011917 | A1* | 1/2011 | Loulmet | A61F 2/2457 227/181.1 |
| 2011/0015618 | A1 | 1/2011 | Satou et al. | |
| 2011/0082538 | A1 | 4/2011 | Dahlgren et al. | |
| 2011/0087067 | A1 | 4/2011 | Rodrigues et al. | |
| 2011/0137400 | A1 | 6/2011 | Dorn et al. | |
| 2012/0035713 | A1 | 2/2012 | Lutter et al. | |
| 2012/0083806 | A1 | 4/2012 | Goertzen | |
| 2012/0165930 | A1 | 6/2012 | Gifford et al. | |
| 2012/0296373 | A1 | 11/2012 | Roorda et al. | |
| 2013/0035757 | A1 | 2/2013 | Zentgraf et al. | |
| 2013/0096672 | A1 | 4/2013 | Reich et al. | |
| 2013/0172978 | A1 | 7/2013 | Vidlund et al. | |
| 2013/0190861 | A1 | 7/2013 | Chau et al. | |
| 2013/0226290 | A1 | 8/2013 | Yellin et al. | |
| 2013/0253532 | A1 | 9/2013 | Fueglister | |
| 2013/0253639 | A1 | 9/2013 | Alkhatib | |
| 2013/0261663 | A1 | 10/2013 | Bittenson | |
| 2014/0031864 | A1 | 1/2014 | Jafari et al. | |
| 2014/0031926 | A1 | 1/2014 | Kudlik et al. | |
| 2014/0074226 | A1 | 3/2014 | Bielefeld et al. | |
| 2014/0088691 | A1 | 3/2014 | Bielefeld | |
| 2014/0100604 | A1 | 4/2014 | Litvack et al. | |
| 2014/0142690 | A1 | 5/2014 | Kovach et al. | |
| 2014/0207154 | A1 | 7/2014 | Bielefeld | |
| 2014/0214152 | A1 | 7/2014 | Bielefeld | |
| 2014/0371766 | A1 | 12/2014 | Morris et al. | |
| 2015/0032206 | A1 | 1/2015 | Alkhatib | |
| 2015/0051616 | A1 | 2/2015 | Haasl et al. | |
| 2015/0250590 | A1 | 9/2015 | Gries et al. | |
| 2015/0272758 | A1 | 10/2015 | Morris et al. | |
| 2015/0313620 | A1 | 11/2015 | Suri | |
| 2015/0359531 | A1 | 12/2015 | Sauer | |
| 2015/0374492 | A1 | 12/2015 | Alkhatib | |
| 2016/0096004 | A1 | 4/2016 | Gerrans et al. | |
| 2016/0256270 | A1 | 9/2016 | Folan et al. | |
| 2017/0007233 | A1 | 1/2017 | Diduch et al. | |
| 2017/0007405 | A1 | 1/2017 | Griffin et al. | |
| 2017/0035569 | A1 | 2/2017 | Deem et al. | |
| 2017/0049435 | A1 | 2/2017 | Sauer et al. | |
| 2017/0156861 | A1 | 6/2017 | Longoria et al. | |
| 2017/0252032 | A1* | 9/2017 | Hiorth | A61F 2/2457 |
| 2017/0258592 | A1 | 9/2017 | Longoria | |
| 2017/0304050 | A1 | 10/2017 | Keidar et al. | |
| 2018/0014931 | A1 | 1/2018 | Morriss et al. | |
| 2018/0185152 | A1 | 7/2018 | Bishop et al. | |
| 2018/0289480 | A1 | 10/2018 | D'Ambra et al. | |
| 2018/0296333 | A1 | 10/2018 | Dixon et al. | |
| 2018/0303614 | A1 | 10/2018 | Schaffner et al. | |
| 2018/0311037 | A1 | 11/2018 | Morriss et al. | |
| 2018/0318083 | A1 | 11/2018 | Bolling et al. | |
| 2019/0000614 | A1 | 1/2019 | Morriss et al. | |
| 2019/0000624 | A1 | 1/2019 | Wilson et al. | |
| 2019/0008639 | A1 | 1/2019 | Landon et al. | |
| 2019/0015205 | A1 | 1/2019 | Rajagopal et al. | |
| 2019/0029671 | A1 | 1/2019 | Zhang et al. | |
| 2019/0029812 | A1 | 1/2019 | Gifford et al. | |
| 2019/0053903 | A1 | 2/2019 | Rohl et al. | |
| 2019/0059876 | A1 | 2/2019 | Decker et al. | |
| 2019/0117400 | A1 | 4/2019 | Medema et al. | |
| 2019/0167197 | A1 | 6/2019 | Abunassar et al. | |
| 2019/0175345 | A1 | 6/2019 | Schaffer et al. | |
| 2019/0175346 | A1* | 6/2019 | Schaffner | A61F 2/2466 |
| 2019/0183648 | A1 | 6/2019 | Trapp et al. | |
| 2019/0290260 | A1 | 9/2019 | Caffes et al. | |
| 2019/0290431 | A1 | 9/2019 | Genovese et al. | |
| 2019/0343633 | A1 | 11/2019 | Garvin et al. | |
| 2020/0113719 | A1* | 4/2020 | Desrosiers | A61B 17/3468 |
| 2020/0330729 | A1 | 10/2020 | Petitpierre et al. | |

FOREIGN PATENT DOCUMENTS

| | | |
|---|---|---|
| CA | 2914495 | 12/2015 |
| CN | 204121085 | 1/2015 |
| CN | 204121092 | 1/2015 |
| CN | 204293210 | 4/2015 |
| CN | 104055600 | 2/2016 |
| CN | 107252327 | 10/2017 |
| CN | 108186163 | 6/2018 |
| CN | 109044564 | 12/2018 |
| CN | 208448390 | 2/2019 |
| CN | 109498216 | 3/2019 |
| DE | 102017002974 | 10/2018 |
| EP | 1330190 | 5/2008 |
| EP | 2537487 | 12/2012 |
| EP | 3027144 | 11/2017 |
| FR | 3063631 | 3/2019 |
| GB | 2530487 | 3/2016 |
| GB | 2563155 | 12/2018 |
| JP | 2018030028 | 3/2018 |
| JP | 2018086571 | 6/2018 |
| JP | 6582748 | 10/2019 |
| WO | WO 89/10096 | 11/1989 |
| WO | WO 00/03759 | 1/2000 |
| WO | WO 00/60995 | 10/2000 |
| WO | WO 02/34167 | 5/2002 |
| WO | WO 03/001893 | 1/2003 |
| WO | WO 03/105670 | 12/2003 |
| WO | WO 2004/017845 | 3/2004 |
| WO | WO 2004/041119 | 5/2004 |
| WO | WO 2004/103162 | 12/2004 |
| WO | WO 2004/103434 | 12/2004 |
| WO | WO 2005/062980 | 7/2005 |
| WO | WO 2005/110244 | 11/2005 |
| WO | WO 2005/112792 | 12/2005 |
| WO | WO 2006/039199 | 4/2006 |
| WO | WO 2006/039223 | 4/2006 |
| WO | WO 2006/039296 | 4/2006 |
| WO | WO 2006/047709 | 5/2006 |
| WO | WO 2006/116558 | 11/2006 |
| WO | WO 2007/021834 | 2/2007 |
| WO | WO 2007/035449 | 3/2007 |
| WO | WO 2007/056502 | 5/2007 |
| WO | WO 2007/061834 | 5/2007 |
| WO | WO 2007/146338 | 12/2007 |
| WO | WO 2007/146362 | 12/2007 |
| WO | WO 2008/101113 | 8/2008 |
| WO | WO 2010/028502 | 3/2010 |
| WO | WO 2010/098804 | 9/2010 |
| WO | WO 2011/154942 | 12/2011 |
| WO | WO 2012/102928 | 8/2012 |
| WO | WO 2012/106328 | 8/2012 |
| WO | WO 2012/137208 | 10/2012 |
| WO | WO 2013/003613 | 1/2013 |
| WO | WO 2013/082454 | 6/2013 |
| WO | WO 2013/173587 | 11/2013 |
| WO | WO 2013/173618 | 11/2013 |
| WO | WO 2013/175468 | 11/2013 |
| WO | WO 2013/177111 | 11/2013 |
| WO | WO 2013/192107 | 12/2013 |
| WO | WO 2014/011794 | 1/2014 |
| WO | WO 2014/028112 | 2/2014 |
| WO | WO 2014/064695 | 5/2014 |
| WO | WO 2014/093861 | 6/2014 |
| WO | WO 2014/110023 | 7/2014 |
| WO | WO 2014/164151 | 10/2014 |
| WO | WO 2014/197620 | 12/2014 |
| WO | WO 2015/020816 | 2/2015 |
| WO | WO 2015/061378 | 4/2015 |
| WO | WO 2015/085307 | 6/2015 |
| WO | WO 2015/161558 | 10/2015 |
| WO | WO 2015/198125 | 12/2015 |
| WO | WO 2016/042022 | 3/2016 |

(56) References Cited

FOREIGN PATENT DOCUMENTS

| | | |
|---|---|---|
| WO | WO 2014/195786 | 4/2017 |
| WO | WO 2017/059426 | 4/2017 |
| WO | WO 2017/066888 | 4/2017 |
| WO | WO 2017/066889 | 4/2017 |
| WO | WO 2017/066890 | 4/2017 |
| WO | WO 2017/079153 | 5/2017 |
| WO | WO 2017/117560 | 7/2017 |
| WO | WO 2017/156259 | 9/2017 |
| WO | WO 2017/210433 | 12/2017 |
| WO | WO 2018/109755 | 6/2018 |
| WO | WO 2018/126188 | 7/2018 |
| WO | WO 2018/167388 | 9/2018 |
| WO | WO 2018/187753 | 10/2018 |
| WO | WO 2019/013994 | 1/2019 |
| WO | WO 2019/145941 | 8/2019 |
| WO | WO 2019/154847 | 8/2019 |
| WO | WO 2020/109576 | 6/2020 |
| WO | WO 2020/109579 | 6/2020 |
| WO | WO 2020/109582 | 6/2020 |
| WO | WO 2020/109588 | 6/2020 |
| WO | WO 2020/109596 | 6/2020 |
| WO | WO 2020/109599 | 6/2020 |

OTHER PUBLICATIONS

Combined Search and Examination Report under Sections 17 and 18(3) issued in United Kingdom Application No. GB1600635.5, dated Jul. 14, 2016.
European Search Report issued in European Application No. 19157011.8, dated Jun. 3, 2019.
Extended European Search Report Office issued in European Application No. 19157011.8, mailed Jun. 3, 2019.
International Search Report and Written Opinion issued in International Application No. PCT/EP2015/071207, mailed Apr. 19, 2016.
International Search Report and Written Opinion issued in International Application No. PCT/EP2019/083135, mailed Feb. 6, 2020.
International Search Report and Written Opinion issued in International Application No. PCT/EP2019/083143, mailed Jan. 31, 2020.
International Search Report and Written Opinion issued in International Application No. PCT/EP2019/083151, mailed Feb. 18, 2020.
International Search Report and Written Opinionissued in International Application No. PCT/EP2019/083159, mailed Feb. 19, 2020.
International Search Report and Written Opinion issued in International Application No. PCT/EP2019/083164, mailed Feb. 11, 2020.
International Search Report and Written Opinion issued in International Application No. PCT/EP2019/083170, mailed Mar. 4, 2020.
Office Action issued in U.S. Appl. No. 15/511,365, dated Apr. 1, 2019.
Office Action issued in U.S. Appl. No. 16/285,716, dated May 3, 2021.
Official Communication issued in European Patent Application No. 15775117.3, dated Sep. 18, 2019.
Search Report Under Section 17(5) for United Kingdom Patent Application No. GB1820258.0, dated May 28, 2019.
Search Report Under Section 17(5) for United Kingdom Patent Application No. GB1819480.3, dated May 28, 2019.
Search Report Under Section 17(5) for United Kingdom Patent Application No. GB1819484.5, dated May 28, 2019.
Search Report Under Section 17(5) for United Kingdom Patent Application No. GB1819489.4, dated May 13, 2019.
Search Report Under Section 17(5) for United Kingdom Patent Application No. GB1819490.2, dated May 16, 2019.
Search Report under Section 17(5) for United Kingdom Patent Application No.. GB1907110.9, dated Nov. 18, 2019.
Search Report under Section 17(5) for United Kingdom Patent Application No. GB2017930.5, dated May 12, 2021.
Search Report under Section 17(5) for United Kingdom Patent Application No. GB1416383.6, dated March 19, 2015.
Search Report under Section 17(5) for United Kingdom Patent Application No. GB1819489.5, dated May 28, 2019.
Search Report under Section 17(5) for United Kingdom Patent Application No. GB1911817.3, dated May 27, 2020.
Search Report under Section 17(5) for United Kingdom Patent Application No. GB1913360.2, dated May 27, 2020.
Search Report under Section 17(5) for United Kingdom Patent Application No. GB1911812.4, dated May 27, 2020.
Search Report under Section 17(5) for United Kingdom Patent Application No. GB2008286.3, dated Nov. 25, 2020.
Search Report under Section 17(5) for United Kingdom Patent Application No. GB2018203.6, dated Apr. 16, 2021.
Search Report under Section 17(6) for United Kingdom Patent Application No. GB1416383.6, dated Dec. 3, 2015, 2 pages.

* cited by examiner

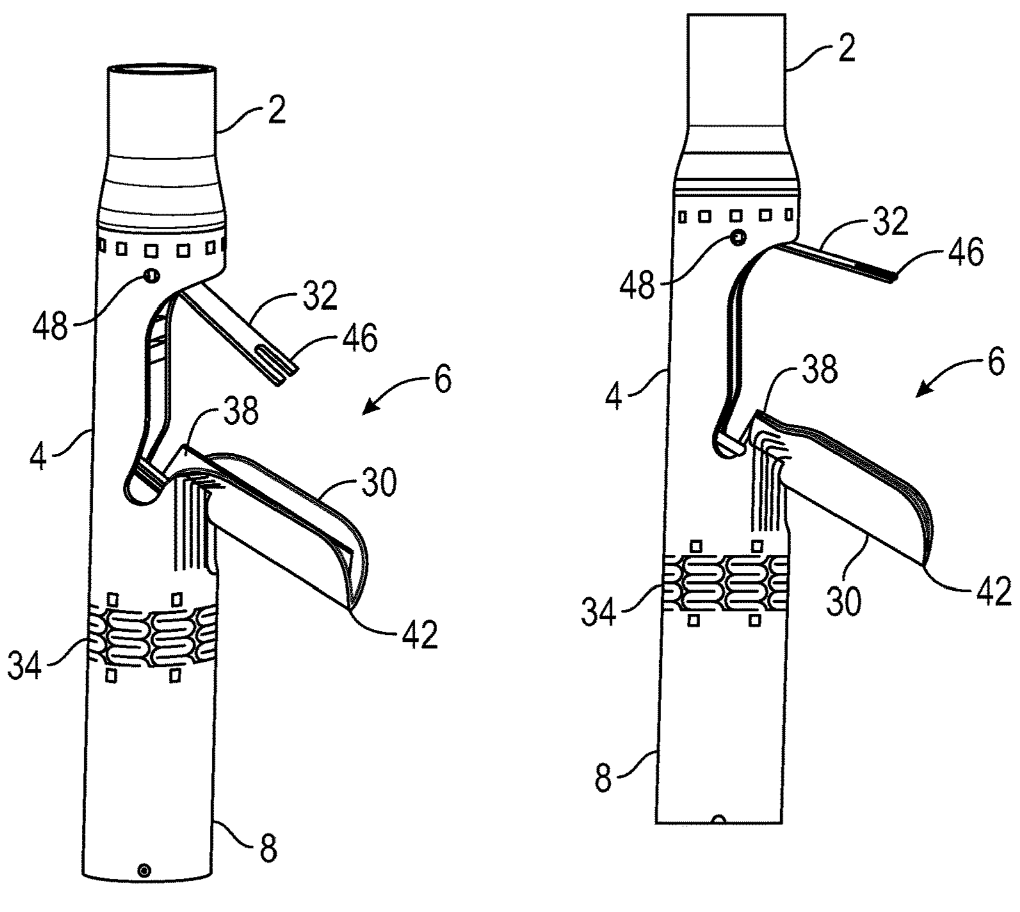
FIG. 4
FIG. 5
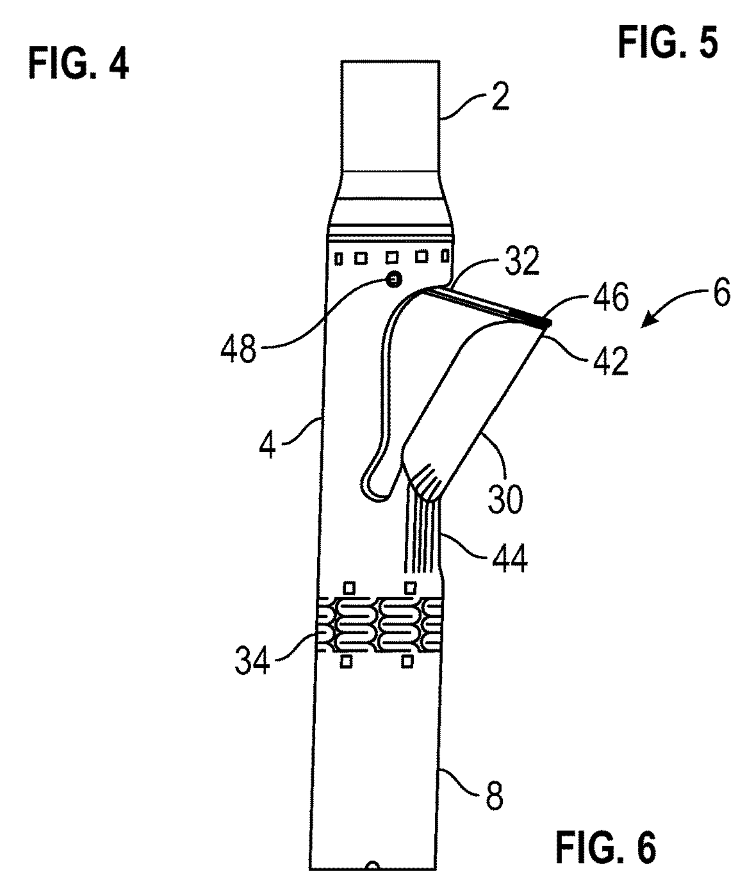
FIG. 6

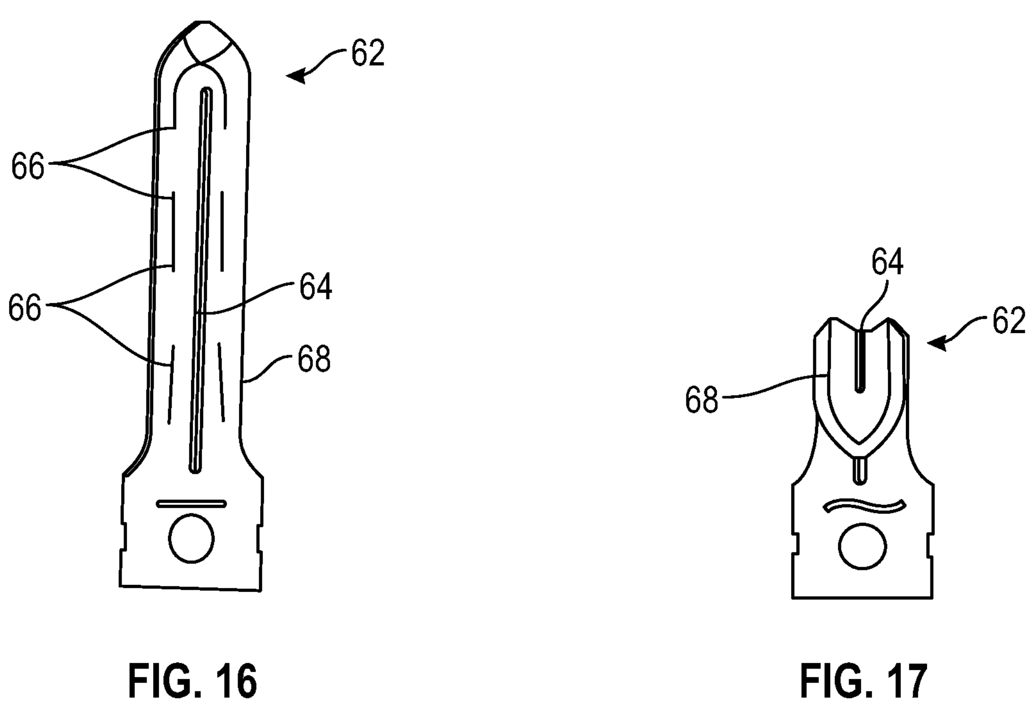
FIG. 16
FIG. 17
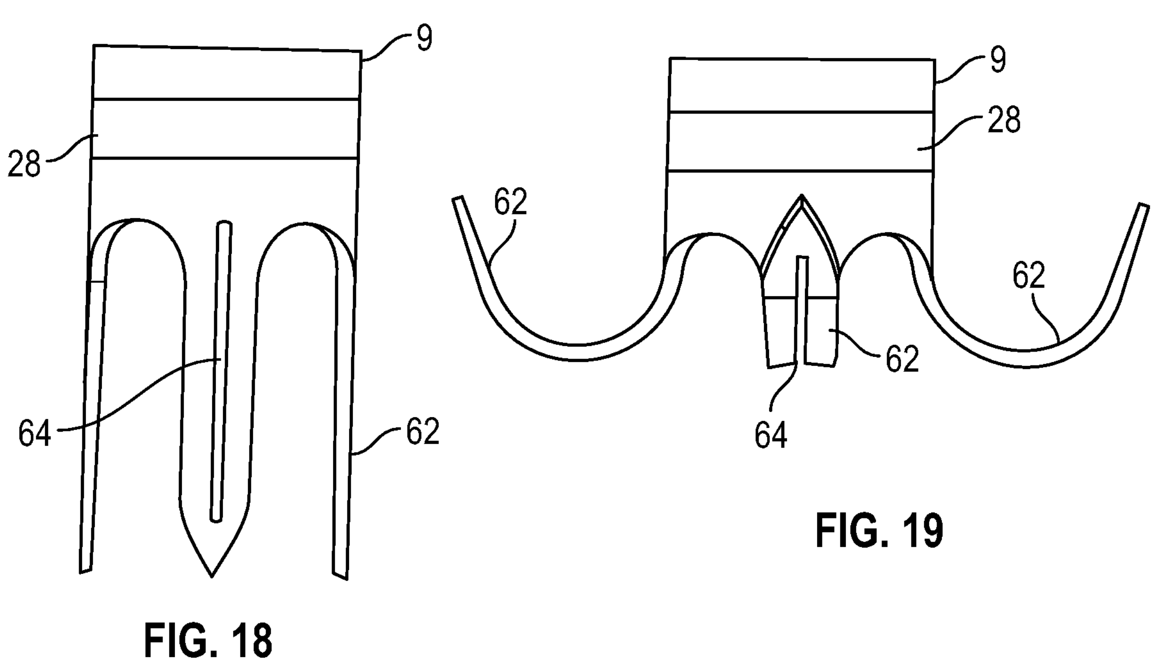
FIG. 18
FIG. 19

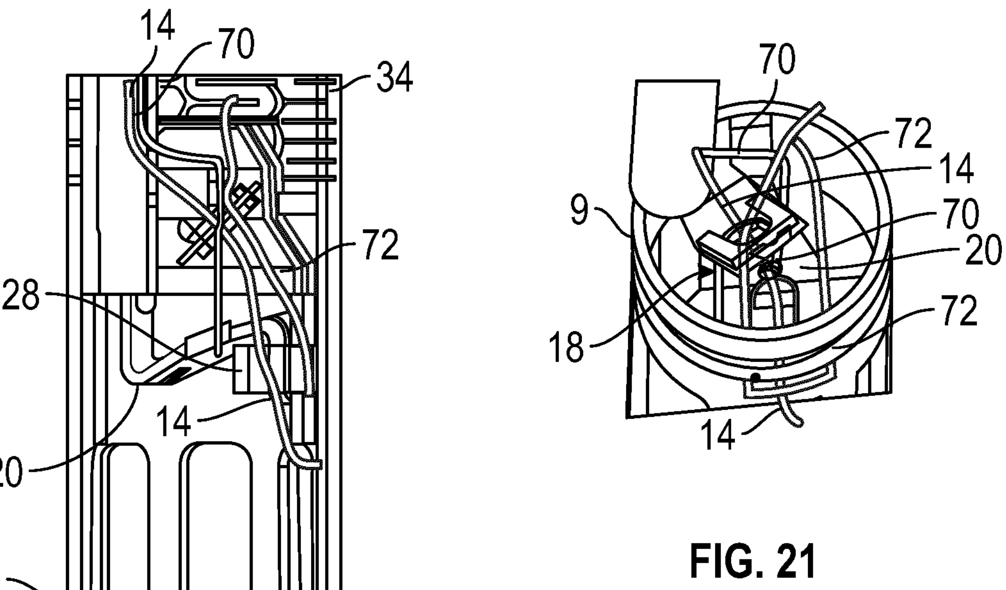
FIG. 21
FIG. 20
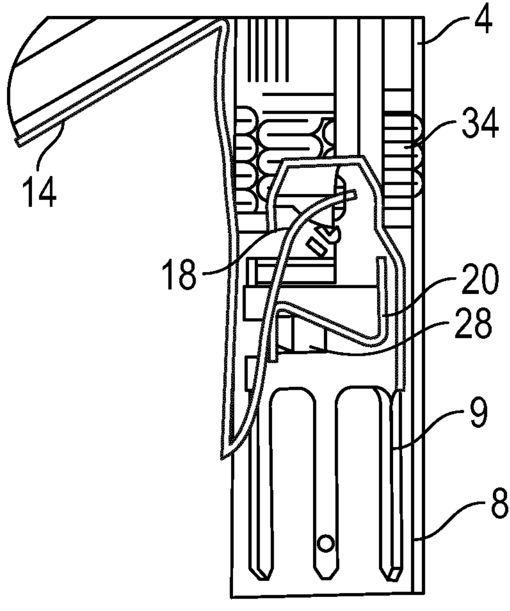
FIG. 22

14
21
97
106
92
94
110
96
28
91
95
62
9

14
97
110
21
96
92
94
95
91
28
106
9
62

106
108
21
120
28
9
62
92

124
8
126
8
124
126
8
124

108
106
9
62
28
106
110

160'
62
109
64
9

64
160
62
109
9

DEVICE FOR HEART REPAIR

CROSS-REFERENCE TO RELATED APPLICATIONS

This application is a national phase application under 35 U.S.C. § 371 of International Application No. PCT/EP2019/083170 filed 29 Nov. 2019, which claims priority to Great Britain Patent Applications No. 1819480.3 filed 29 Nov. 2018; 1819489.4 filed 29 Nov. 2018; 1819484.5 filed 29 Nov. 2018; 1819490.2 filed 29 Nov. 2018; 1820258.0 filed 12 Dec. 2018; 1820990.8 filed 21 Dec. 2018; 1904688.7 filed 3 Apr. 2019; 1907110.9 filed 20 May 2019; 1911817.3 filed 16 Aug. 2019; 1911812.4 filed 16 Aug. 2019; 1913057.4 filed 10 Sep. 2019; and 1913360.2 filed 16 Sep. 2019. The entire contents of each of the above-referenced disclosures is specifically incorporated by reference herein without disclaimer.

The present invention relates to various parts of a device for implanting an artificial chordae line in order to repair a heart valve, as well as to related methods. This disclosure also includes an anchor for implantation within body tissue, which may be used for heart repair.

The chordae tendineae are cord-like tendons that connect the papillary muscles to the tricuspid valve and the mitral valve in the heart. The valves consist of leaflets that open and close with the beating of the heart in order to control blood flow and blood pressure within the heart.

Mitral valve disease presents an important challenge to cardiac surgeons and cardiologists. Mitral regurgitation has become the leading pathophysiological condition of the mitral valve in the developed world. One of the most important causes of regurgitation is prolapse of one of the mitral leaflets. The pathological abnormality that requires repair is rupture or other degenerative changes of the chords, leaflet or other related structures. When the chord(s) remain intact, the mitral leaflets open and close synchronously and in a fashion that prevents leakage of the valve. The normal chords can rupture acutely causing acute decompensation, in the form of, heart failure. This usually results in an emergency condition requiring rapid intervention. Damage to the chord(s) can also occur more slowly including rupturing or elongation due to degenerative processes, causing the mitral valve to develop leaks or regurgitation.

Surgical repair of the mitral valve has become relatively standardized, using resection of the prolapsed leaflet and/or implantation of new, artificial chordae lines to control leaflet motion. In addition a mitral ring is frequently placed to shrink the size of the mitral valve annulus. Surgical replacement of ruptured or elongated chords is highly effective in eliminating or minimizing mitral valve regurgitation. The procedure is presently performed with open heart surgery techniques. This requires use of cardiopulmonary bypass and arresting of the heart. This surgical approach, although working well, is a highly invasive procedure which can cause serious complications, long hospital stays and substantial expense. Consequently a less invasive approach would be preferable.

Insertion of mitral leaflet chords has been done using a minimally invasive surgical approach entering the heart through its apex. The technique, was developed by the company Neochord Inc. and is described, for example, in WO 2012/167120, but still requires a surgical incision and the chords do not get inserted in the papillary muscles where they normally should be fixed.

WO 2008/101113 describes another example of a system for repair of the heart, including implantation of artificial chordae lines. In the described method an anchor can be attached to the papillary muscle and is coupled to the leaflet of the mitral valve by an artificial chordae line, a suture and a clip. The clip allows for adjustment of the length of the artificial chordae line. A complex multi-stage process is required to implant the papillary anchor and the suture and join them together. The papillary anchor is formed of a memory metal such as nitinol and has a 'flowered' shape with sharp 'petals' for hooking the anchor to body tissue. The flowered shape is flattened into a tube shape and held in a tube that is passed into the heart. The tube and anchor are then pressed against the papillary muscle and the anchor is pushed out of the tube so that the petals pierce the muscle and fold outward through the muscle to provide a secure coupling of the anchor to the muscle tissue. In a subsequent surgical procedure, an artificial chordae line may be attached to the anchor. Then in a further step, the suture is attached to the leaflet and this suture is joined to the chord by the clip. The suture is attached to the leaflet by locating a vacuum port near to the leaflet and pulling it into the vacuum port where it can be pierced.

It will be appreciated that this technique, whilst avoiding open heart surgery, still requires a sequence of relatively complex steps. The number of steps required increases the risk. Furthermore, the complexity of the device means that parts implanted within the body are at risk of coming loose and injuring the patient by embolization. In particular, the clip could come loose from the anchors. It is also thought that the use of a suture with an additional clip, as proposed, may not effectively repair the heart valve since it will not closely simulate a natural chord.

In an earlier patent application, WO2016/042022, the present applicant disclosed a catheter device for implanting an artificial chordae line to repair a heart valve. The catheter device of WO2016/042022 includes a mechanical gripper device for grasping the leaflet of the heart valve, with a leaflet anchor housed in the gripper. The leaflet anchor can be formed from a flexible material, such as nitinol, with a grapple hook shape in an unfolded configuration, and being able to deform elastically into the folded configuration, for example when constrained within a leaflet anchor channel in the gripper device. The hooks are straightened out when the leaflet anchor is in the folded configuration. When the leaflet is grasped by the gripper device then the leaflet anchor can be pushed out of the gripper to drive the hooks though the leaflet whilst they return elastically to the unfolded configuration, thereby securing the leaflet anchor in the leaflet.

The device described in WO2016/042022 also uses a papillary anchor with a broadly similar arrangement of foldable hooks. The papillary anchor is held within a tube of the catheter device in a folded configuration and can be pushed out of the tube with the hooks being driven through the papillary muscle whilst they return elastically to the unfolded configuration, thereby securing the papillary anchor to the muscle. The papillary anchor includes a locking ring acting as a locking mechanism for clamping an artificial chordae line when no force is applied. The locking ring maybe elastically deformed to release the line from the locking mechanism for adjustment of the length of the chordae line.

Whilst the device of WO2016/042022 provided a significant advance in this field it has been found that further refinement of the design may be advantageous. The present disclosure relates to new features building on the design of the device disclosed in WO2016/042022 in various respects.

In accordance with the present invention a catheter device as discussed in the sixth aspect, a method of use of a catheter device as discussed in the ninth aspect and a method of manufacture of an ejector unit as discussed in the thirteenth aspect are herein provided.

Viewed from a first aspect the invention provides a catheter device for repair of the heart by implanting an artificial chordae line, the catheter device comprising: a leaflet anchor for placement in a leaflet of a heart valve, wherein the leaflet anchor is arranged to be coupled to the artificial chordae line; and a leaflet anchor deployment mechanism for deploying the leaflet anchor to attach it to the leaflet of the heart, wherein the leaflet anchor deployment mechanism comprises a mechanical gripper device for grasping the leaflet of the heart valve, wherein the gripper device comprises a leaflet anchor tube for housing the leaflet anchor in a folded configuration; the gripper device and leaflet anchor being arranged such that when, in use, the gripper device grasps the leaflet, the leaflet anchor can be pushed out of the leaflet anchor tube to pierce the leaflet and form the leaflet anchor into an unfolded configuration so that hooked formations of the leaflet anchor can, in use, secure the leaflet anchor in the leaflet; wherein the mechanical gripper device includes a first gripper arm rotatably coupled to a main body of the catheter device so that the first gripper arm can rotate relative to the catheter device to move an outer end of the first gripper arm away from the main body of the catheter device and a second gripper arm rotatably and/or slideably coupled to the main body of the catheter device so that the second gripper arm can rotate and/or slide relative to the main body of the catheter device to move an outer end of the second gripper arm away from the main body of the catheter device; and wherein the first and second gripper arms are arranged so that they can move to come into contact with one another at a point spaced apart from the main body of the catheter device.

This arrangement can provide various advantages. For example, in the arrangement where the second gripper arm is rotatably coupled to the main body of the catheter device and/or where the second gripper arm can react to a sufficiently high force from the first gripper arm, then the use of two gripper arms allows for the leaflet to be gripped between the two arms at a point spaced apart from the main body, rather than only enabling the leaflet to be gripped between a single gripper arm and the main body, which is the arrangement described in WO2016/042022. The use of two gripper arms in this way can additionally or alternatively help stabilise a flailed leaflet, which is a leaflet segment without functioning chorda, that may flail into the atrium and be hard to catch with prior art devices. For example, the leaflet tends to move upwards which can make it difficult to catch the leaflet using a single gripper arm alone. Thus, in this regard, the second gripper arm may be considered as being a 'leaflet motion suppressor', as it may help to stabilise the flailing motion of the leaflet during a cardiac cycle. The use of a second gripper arm may also allow for a more horizontal gripping/contact surface (i.e. more perpendicular to the main body of the catheter device), which is beneficial both in terms of constraints on orientation of the main body, which is typically inserted from above the leaflet, and also has further advantages in relation to example embodiments in which the implantation of the leaflet anchor is carried out using the same device that implants a papillary anchor. In particular, the use of two gripper arms with a more perpendicular gripping location can facilitate the use of a device for performing the procedure of implanting both a leaflet anchor and a papillary anchor whilst the device remains in one place. It will be appreciated that the gripper arms may not necessarily be rigid structures, but may be flexible as required to achieve their desired operation.

In some examples, the use of two gripper arms allows for motion of the leaflet to be restrained between the two gripper arms at a point spaced apart from the main body. Thus, at (and near) the point(s) where the first gripper arm and the second gripper arm can contact one another then when the leaflet is present they will engage with the leaflet and restrict its movement. The leaflet tends to move upwards which can make it difficult to catch the leaflet using a single gripper arm alone. Thus, in this regard, the second gripper arm may be considered as being a 'leaflet motion suppressor', as it may help to stabilise the flailing motion of the leaflet during a cardiac cycle. Thus in this implementation, the second gripper arm may be slidably moved away from the main body of the catheter device to contact the top of the leaflet. The catheter device may be moved downwards such that the first gripper arm may then be rotatably moved away from the main body of the catheter device without contacting the leaflet or the second gripper arm, before being rotated back towards it. As the first gripper arm rotates back into the main body it then contacts the second gripper arm, which may for example be a flexible arm, restraining the leaflet between the two. The contact made by the first gripper arm against the second gripper arm may in this case be a slidable contact, allowing the first gripper arm to rotate back towards the main body whilst maintaining restraint of the leaflet. The first gripper arm then grasps the leaflet between itself and the main body of the catheter device. Hence as the first gripper arm is withdrawn back to grip the leaflet between the first gripper arm and the main body, as similarly described for the single gripper arm in WO2016/042022, the second gripper arm restrains the leaflet and prevents the leaflet from slipping out and thus the presence of the second gripper arm ensures the grasping of the leaflet in the first gripper arm. The use of a second gripper arm will also allow for a more horizontal gripping surface (i.e. more perpendicular to the main body of the catheter device), which is beneficial both in terms of constraints on orientation of the main body, which is typically inserted from above the leaflet, and also has further advantages in relation to example embodiments in which the implantation of the leaflet anchor is carried out using the same device that implants a papillary anchor. In particular, the use of two gripper arms with a more perpendicular contact location can facilitate the use of a device for performing the procedure of implanting both a leaflet anchor and a papillary anchor whilst the device remains in one place. It will be appreciated that the gripper arms may not necessarily be rigid structures, but may be flexible as required to achieve their desired operation.

The improved design may also allow large parts of the device to be produced from an elastic metal such as nitinol or stainless steel, and this in turn can allow for a production method that is reproducible and inexpensive. Alternatively, large parts of the device may be produced from a composite material, with choice parts formed from an elastic material such as nitinol or stainless steel as appropriate. The composite materials may comprise, for example, glass reinforced PEEK or carbon reinforced PEEK (CRF PEEK). Composite materials may have the advantage of improved imaging from ultrasound to allow monitoring during any procedure the catheter device is used for. Whilst composite materials may be not be as visible in x-ray imaging, radioactive markers or opaque contrast markers may be strategically located on the device to provide for such imaging. Composite materials may also be used for injection moulding of the components of the catheter device as required.

It will be appreciated that the leaflet anchor deployment mechanism of this aspect, as well as providing its own advantages, may also combine synergistically with the catheter devices of the aspects described below. Thus, it may be used to deploy the leaflet anchor in the device of the second aspect, for example with the leaflet anchor deployment mechanism placed in the proximal part of the two-part housing section. Alternatively or additionally it may be combined with the use of an ejector unit as disclosed in relation to the sixth aspect.

Capturing a leaflet with flail can be challenging, as it can move both "up" and "down" during a heartbeat. The gripper device of this aspect is equipped with an additional gripper arm to address this issue. The two gripper arms can both move relative to the main body of the catheter device. In some examples, the first gripper arm acts to enclose the second gripper arm, such that the first gripper arm must be rotated by a certain amount away from the main body of the catheter device before the second gripper arm can be freely rotated and/or slid within its entire range of movement. It may be that the second gripper arm can only be moved relative to the main body of the catheter device once the first gripper arm is opened to a certain degree.

The leaflet anchor tube may be housed within either the first gripper arm or the second gripper arm. The leaflet anchor is deployed by pushing it out of an opening at the end of the leaflet anchor tube, which is at the end of the respective gripper arm. In the example embodiments the leaflet anchor tube is within the first gripper arm, which may also enclose the second gripper arm as discussed above.

The two gripper arms may be operated individually to allow for independent movement. Alternatively, they may be linked in order that they move simultaneously similar to a "tweezers" mechanism. The use of two gripper arms can allow the upper gripper arm, which may be the second gripper arm, to make a "roof" for the leaflet, reducing the movement, and making the grasping easier especially when the leaflet is a complete flail. Another benefit is that the grasping action is more horizontal rather than vertical, i.e. more perpendicular to the main body of the catheter device than parallel to it.

In one example the first gripper arm may be arranged to be opened by rotation away from the main body, through 45 degrees or more, and preferably to an obtuse angle. The second gripper arm may be arranged to be enclosed by the first gripper arm when the first gripper arm is closed, and may be able to swing and/or slide outward from within the main body of the catheter device once the first gripper arm is open. Where the second gripper arm rotates then it may rotate with an opposite direction of rotation to the first gripper arm and may be arranged so that the rotation brings the end of the second gripper arm into a path of movement of the end of the first gripper arm. A centre of rotation for the first gripper arm may be spaced apart along the length of the main body of the catheter device compared to a centre of rotation of the second gripper arm. It should be noted that the centre of rotation may not be fixed as there may be some deformation of the device during the rotation process, for example the first gripper arm may rotate by bending of a flexible section of material, which can lead to movement in the centre of rotation depending on the degree of bending. In cases where the second gripper arm slides then it may slide to move its end outward from the main body of the catheter device and into the path of movement of the end of the first gripper arm.

The gripper arm(s) may be moved by pulling one or more wire(s), which may be connected to lever arms joined to the gripper arm(s). With the second gripper arm open (i,e, rotated or slid outward from the main body) with its end spaced apart from the main body, for example with the second gripper arm extending at an angle of between 45-90 degrees from the main body, then the first gripper arm may be rotated in the closing direction toward the end of the second gripper arm, such that the first gripper arm moves to contact part of the second gripper arm.

In some examples the gripper device may capture the leaflet, and/or restrain its movement, by engagement (contact) of the two gripper arms, which may be done by rotation of one or both arms. The second gripper arm may also be individually moved during the gripping action. The two gripper arms may move in order to engage a gripping surface of the second gripping arm with a gripping surface of the first gripper arm.

The gripper device may capture the leaflet by first restraining it between a contact point between the second gripper arm and the first gripper arm. The first gripper arm may then be rotated closed, i.e. towards the main body of the catheter device, such that the restrained leaflet is successfully grasped by the first gripper arm. The second gripper arm may remain fixedly in place during motion of the first gripper arm.

For the gripper arm that houses the leaflet anchor tube, which may be the first gripper arm, the gripping surface may be a gripping platform located around the opening of the leaflet anchor tube. Whilst the leaflet is gripped between the two gripper arms or a gripper arm and the main body of the catheter device, the leaflet anchor is placed, for example using any technique discussed above and then the gripping device is opened, for example by rotation of the first gripper arm away from the second gripper arm and/or the main body of the catheter device. Where the device of this aspect is combined with the device of the sixth aspect and hence an ejector unit is present, then the connection of the leaflet may be tested after the gripping device is opened to ensure proper placement of the leaflet anchor in the leaflet prior to release of the leaflet anchor from the ejector unit.

The second gripping arm may be actuated with two wires, allowing the physician to move it in two rotating or sliding directions to aid in the grasping process.

The second gripper arm, i.e. the leaflet motion suppressor, may be a flexible member and/or may comprise a wire. The wire may be formed of an elastic material such that it may be contained, housed, stored and/or sheathed within a lumen of the main body of the catheter device when not in use. The elastic material may be nitinol or stainless steel, for example. This advantageously gives a user of the device the decision of whether or not the use of the second gripper arm is desired during placement of the leaflet anchor.

The leaflet motion suppressor comprising an elastic wire may be in an elastically deformed state when stored within the lumen. However, when the leaflet motion suppressor is moved away from the main body of the catheter device the leaflet motion suppressor may return to an undeformed state. The leaflet motion suppressor may be slid out of the lumen to move its end away from the main body of the catheter device.

The leaflet motion suppressor may comprise a number of shapes and/or arrangements capable of suppressing flail of the leaflet, to ensure engagement of the leaflet between the first gripper arm and the second gripper arm, when the leaflet motion suppressor is in its undeformed state.

In one example the second gripper arm may be a looped nitinol wire that is pushed out of the proximal end of the device, by pushing the two proximal wire ends toward the distal end of the device, a looped wire extends out of the proximal end of the gripper housing. The loop in the wire may advantageously stabilise the leaflet motion suppressor as it engages the leaflet. The loop of wire may encompass a large surface area which assists with engagement of the leaflet.

The loop of wire may also prevent the leaflet motion suppressor from being withdrawn completely into the catheter device. That is, the loop of wire may engage with a feature of the lumen such as a pin, such that a distal end of the wire is always outside and/or flush with a main body of the catheter device. Thus for the leaflet motion suppressor comprising a wire, a portion of the wire and/or an end of the wire may be located outside of/flush to an outer surface of the proximal part of the main body of the catheter device.

In another example, the second gripper arm may be an open-ended and/or loose wire, i.e. a wire wherein at least one of the ends is located outside the main body of the catheter device when in the undeformed state. The wire being open-ended and not forming a loop may help prevent entanglement of the leaflet in the leaflet motion suppressor. In this arrangement, the leaflet motion suppressor may comprise a number of bends and/or curves parallel to the plane of the leaflet, which advantageously increases the surface area of engagement between the leaflet motion suppressor and the leaflet. To prevent the leaflet motion suppressor from being completely withdrawn into the catheter device, the wire may comprise a wire stopper at its end, the wire stopper being a feature such that the wire stopper is wider and/or larger than the lumen.

When the leaflet motion suppressor comprises a wire with at least one end of the wire configured to be outside the main body of the catheter device, the leaflet motion suppressor may undesirably pierce and/or damage the leaflet or surrounding tissue as the second gripper arm is slid out of and/or moved away from the main body of the catheter device. With the aim of preventing this disadvantageous effect, the bends and/or curves of the wire may be formed such that the end of the wire is configured to point away from the leaflet. For example, the end of the wire may curve away from a surface of the leaflet, or may point in a direction opposite to that which the second gripper arm is to be moved. Additionally and/or alternatively, the end of the wire may comprise a soft tip to decrease the chance of puncturing the surrounding tissue.

In one example, the undeformed shape of the leaflet may comprise a spiral, the spiral forming a large engagement surface between the leaflet and the second gripper arm. The spiral may also be formed such that the end of the wire located outside the main body of the catheter device is at the centre of the spiral. Advantageously, this decreases the likelihood that the end of the wire pierces and/or damages the surrounding tissue as the end of the wire is less exposed.

The lumen in which the leaflet motion suppressor is stored may comprise a channel, path and/or conduit running along a length of the catheter device parallel to a main axis of the catheter. However, where the lumen meets the mechanical gripper device the lumen may angle towards an outer surface of the main body of the catheter device such that the leaflet motion suppressor may slide out of the lumen to engage the leaflet. The lumen may be angled such that the leaflet motion suppressor leaves the lumen perpendicular to a surface of the main body of the catheter device.

The wire component of the leaflet motion suppressor may be an off-the-shelf wire, such as a guide wire, readily available for use in cardiac interventions. Accordingly, an operator of the catheter device can then choose a wire that they find appropriate for suppressing motion of the leaflet during an operation. In other words, different wires of an identical predefined size may be implemented with different stiffness and/or tip structure (i.e. bends, curves and/or loops) as desired. For example, if a first wire did not function as desired, a second wire having similar or different characteristics may be used. As such, the leaflet motion suppressor may not be stored within the lumen of the catheter device permanently, but may be selected from a storage device and inserted into a port of the catheter device during a particularly challenging procedure. This approach has the further advantage that it may use wire components for which regulatory approval has already been granted, and/or wire components that the user is familiar with from other types of cardiac interventions.

The first gripper arm may be actuated with a single wire or with multiple wires. Advantages can be obtained if a hinge mechanism for the first gripper arm is formed integrally with the material of the main body and rotates away from the main body by elastic deformation of that material. The first gripper arm as well as the hinge mechanism may be formed integrally with the material of the main body. Alternatively, the first gripper arm may include a separately formed arm section, such as a milled piece or a laser cut piece, with the separate arm section being attached to a hinge mechanism of the main body, for example by gluing or welding.

In a slightly different arrangement the second gripper arm may be attached to the base (somewhere close to the rotational "axis") of the first gripper arm. This second gripper arm may be an elastic material such as nitinol. In a default configuration the second gripper arm may follow the gripping surface (inner surface) of the first gripper arm with a slight pressure towards the gripping surface of the first gripper arm, with the pressure being induced by tension in the material of the second gripper arm. The arrangement can be compared to a "reversed" tweezer, where a force is needed to open it. The reversed tweezer follows the movement of the first gripper arm unless there is a force that pulls it open, the force could for example be in form of a pull wire, or wedge placed in between the first and second gripper arm.

In some examples, the main body of the catheter device may be formed from an elastic metal such as nitinol with a hinge being provided by an elastic joint formed in the elastic metal. In that case a single wire can be used to elastically deform the first gripper arm by bending an elastic joint with the main body to rotate the end of the first gripper arm away from the main body, with the first gripper arm returning elastically to its at rest position once no force is applied to the wire. An advantage of this is that the elastic force of the first gripper arm can hold it in place against the second gripper arm when the force is released from the wire, without the need for a separate wire to be pulled to keep the grip on the leaflet secure. A second wire may however be implemented as a backup if it may be needed.

In other examples, the main body of the catheter device may be formed from a composite material, such as carbon or glass reinforced PEEK. The first gripper arm may then be joined to the main body of the catheter device using a pin joint, the pin forming the axis of rotation of the first gripper arm. Similarly, when the second gripper arm comprises a sheet of elastic metal, the rotatable element of the arm may be formed by another pin joint located on the surface of the main body of the catheter device. The pin joint mentioned herein may be a revolute joint or a hinge joint, i.e. comprising intermeshing features with a pin or cylindrical member joining said members, the pin forming the axis of rotation for the joint. The motion of the second gripper arm may then be controlled by one or more pullwires, as described above. When the second gripper arm comprises a single wire as described above, the lumen may be formed through the composite material to allow passage of the leaflet motion suppressor in and out of the catheter device.

Alternatively or in addition the first gripper arm can be heat set in a "more than closed" configuration. This would allow the first gripper arm to grasp tissue towards the main body of the device as well as towards the second gripper arm.

To form both the first gripper arm and the hinge integrally with the main body of the catheter then the main body of the catheter may comprise an outer tube, with the first gripper arm being formed as an articulated section of the outer tube. Several forms of slits and/or patterns can be formed in the tubing in order to provide a weakened hinge section allowing for bending without plastic deformation of the first gripper arm.

In alternative arrangements a hinged gripper arm may be used. In that case the first gripper arm may be milled, actuation in that case could be done with a spring for closing, and wire for opening, or vice versa, or with two wires (one for opening and one for closing). A pulley cut in the device can be used to redirect the pulling force from the pull wire.

One or both gripping surface(s) may be arranged to hold the leaflet with friction. For example the gripping surface(s) may use a material with a high coefficient of friction and/or the gripping surface(s) may have a texture or surface profile for increasing friction, such as a ridged or saw-toothed profile. The end of the leaflet anchor tube typically opens into one of the gripping surfaces. The leaflet anchor tube may take the form of a generally cylindrical channel sized to be slightly larger than the leaflet anchor in its folded configuration.

The leaflet anchor may be formed from an elastic material and to be arranged so that it assumes the unfolded configuration when no force is applied, and to be able to deform elastically into the folded configuration, for example when constrained within the leaflet anchor tube. Further possible features of the leaflet anchor are discussed at various points below.

It is advantageous if the leaflet anchor can be placed into the leaflet from beneath, i.e. from the side where the papillary muscle is located. To facilitate the preferred placement of the leaflet anchor from beneath, the catheter device may be arranged so that the open end of the leaflet anchor tube is at a proximal end of the gripper device (the 'upper' end when in the heart in the above defined orientation) and the leaflet anchor can be pushed out of the channel moving from the distal end of the catheter device toward the proximal end. Thus, the end of the first gripper arm may also have the end of the leaflet anchor tube, and this may be arranged to direct the leaflet anchor in a direction extending toward the proximal end of the catheter device. In some embodiments the catheter device includes a U-shaped rod for deployment of the leaflet anchor, as discussed further below.

In some examples the second gripper arm can be cut out of the main body of the catheter device in a similar way to as the first gripper arm, for example cut from a piece of the main body at an opposite side of the main body to the first gripper arm. This second gripper arm could have cut features in its base, allowing for a tight bend being pulled out of the device, and may also be heat formed for increased stiffness.

In examples using a mechanical hinge for the first gripper arm the catheter device main body could be made of an elastic metal such as nitinol while the first gripper arm itself is milled from stainless steel otherwise formed separately. Alternatively, the main body may be milled with the gripper arm cut from elastic metal, or the entire device could be milled or made by additive manufacturing.

The leaflet anchor tube can be heat treated with a flattened section on its inner end that extends past the first gripper arm's "centre" of rotation. This can act as a lever for pulling the first gripper arm open.

The second gripper arm may be cut from sheet metal, such as nitinol, and placed within the main body of the catheter device in an elastically deformed state. This deformation may be purely to allow the arm to take a smaller profile for insertion into the main body, so that it will expand into a non-deformed state once it is within the main body. Alternatively, some elastic deformation may remain once the second gripper arm is within the main body, for example, so that it will retain itself in place via elastic forces and/or so that it may automatically deploy by unfolding elastically when the first gripper arm is opened. The second gripper arm may be formed with heat setting with for example a light curve or a convex curve to improve stiffness and or provide a gripping surface. Wave or barbed edges may be provided in order to enhance the gripping strength of the gripping device. In addition, or alternatively slits can be placed on the surface of the second gripper arm to provide different flexing properties. In some examples a hinge mechanism for the second gripper arm is formed in the main device by the use of two holes, with pins formed in the second gripper arm that fit into the holes. This may be assembled by inserting the second gripper arm with elastic deformation as discussed above, and by allowing the second gripper arm to fully or partially unfold into a position where the pins engage with the holes to make the hinge. Wires can be attached to the second gripper arm to move it up and down, or it could be spring loaded one way, and pulled the other way.

When the two armed gripper of this aspect is combined with the second aspect and its flexible joint, then in one example the two-part housing section of the second aspect is made from a single tubing section cut to a required shape, with the first gripper arm being provided in the proximal part of the two-part housing section, which forms the main body of the catheter device, and with the first gripper arm advantageously being cut from the same tubing section. In this way it becomes possible to create many features of the catheter device from a single tubing section, such as from laser cut nitinol. Alternatively the two-part housing section of the second aspect is made from two parts coupled with a hinge, as discussed above, and in this case the catheter device may be formed from a combination of materials, perhaps including composite materials.

Viewed from a second aspect the invention provides a catheter device for implanting a leaflet anchor and a papillary anchor into the heart as part of a procedure for implanting an artificial chordae line that extends between the leaflet anchor and the papillary anchor, the catheter device comprising:

a two-part housing section extending from a distal end of the catheter device along the length of the catheter device toward the proximal end of the catheter device, the two-part housing section being arranged to be placed between the papillary muscle and a leaflet of the heart during use of the catheter device, and the two-part housing section comprising a distal part at the distal end of the catheter device and a proximal part located on the proximal side of the distal part;

a leaflet anchor deployment mechanism at the proximal part of the housing section for deploying a leaflet anchor for attachment to the leaflet of the heart;

a papillary anchor deployment mechanism at the distal part of the housing section for deployment of a papillary anchor for attachment to the papillary muscle, wherein the papillary anchor deployment mechanism is arranged for deployment of the papillary anchor by moving it outward in the distal direction relative to the distal part; and a flexible joint located between the proximal part and the distal part of the two-part housing section, wherein the flexible joint allows a centreline of the distal part to be angled relative to a centreline of the proximal part.

The device of this aspect provides a new method to insert the papillary anchor that may allow the physician to implant the leaflet and papillary anchors without the need to move the device after first placing the leaflet anchor, or after locating the device ready to place the leaflet anchor/grasp the leaflet (with the papillary anchor being placed first in the latter situation). In contrast to the device described in WO2016/042022 the catheter does not necessarily need to be moved to a different orientation or position within the heart before the papillary anchor is placed. Instead the flexible joint may allow for the distal part to be angled toward the papillary muscle area while the remainder of the catheter device is not moving. The flexibility of the joint, can also allow for the distal end of the distal part to push more evenly against the papillary muscle, i.e. to ensure that it presses against the body tissue more evenly across the whole cross-section of the distal end. In turn this ensures effective implantation of the papillary anchor, since it can engage with the body tissue around the whole cross-section.

This device hence reduces the risk of entanglement as well as minimising the time needed for the implanting procedure. In WO2016/042022 a method to place the anchor is described but the design of the papillary anchor deployment mechanism and its housing needs greater care to ensure that all of the anchor pins were well engaged with the body tissue. It should be noted here that in this document the term "pins" is used interchangeably with the term "hooks" and the same elements of the anchor is described in each case.

Optionally, the flexible joint may also be extendable. Thus, there may be a flexible and extendable joint between the proximal part and the distal part of the two-part housing section. The flexible and extendable joint may allow the distal part to be moved away from the proximal part via extension of the joint to thereby extend the distal end of the catheter device further into the heart. In this way the device can be extended to move the distal part of the housing section along with the papillary anchor in a direction toward the papillary muscle area while the remainder of the catheter device is not moving. The resilience of the flexible (and extendable) joint can act to avoid excessive force on the body tissue, reducing the risk of trauma during implantation, as well as aiding in ensuring an even pressing force with the extending and flexing mechanisms working in combination.

The papillary anchor may consist of a number of pins that are arranged to form hooks in the body tissue as the anchor moves out of the distal part of the housing section into a deployed configuration. In some examples a papillary anchor of similar design to that of WO2016/042022 could be used. In other examples the papillary anchor may have further features as discussed below, such as slits along the pins. The proposed device of the second aspect might also be used with other types of anchors that need to be placed at a distance, such as a screw anchor or a barbed anchor.

As explained above, by adding a flexible joint between the two parts of the housing section a more reliable deployment and lower chance of entanglement can be achieved. The flexibility of the joint also helps the device travel through bends in the catheter as it is split into two shorter straight parts that can flex relative to one another, rather than being one long rigid section. The flexible joint allows a centreline of the distal part to be angled relative to a centreline of the proximal part, and these centrelines may be aligned with a centreline of the catheter when the device is at rest. It will be appreciated that the device will have a prismatic form, typically cylindrical, and the centrelines may hence be along the centre of the cross-section of the prism. During use of the device the centreline of the proximal part of the housing section may remain aligned with a centreline of adjacent parts of the catheter that support the housing section, whereas the centreline of the distal part may be angled differently.

The optional feature of an extendable joint also allows the distal part to be moved away from the proximal part to thereby extend the distal end of the catheter device further into the body/heart, and thus it has a telescopic effect that changes the overall length of the two-part housing section. Where a flexible and extendable joint is used this may have two separate mechanisms to provide the required flexibility and extendibility. Thus, there may be a mechanism arranged for bending between the two parts, and a separate mechanism for extension via some form of telescopic effect. The telescopic effect might in this case be provided by a sliding sleeve arrangement, by foldable or hinged structures, and/or by elastically collapsible structures. In other examples, including the example embodiment illustrated herein, the flexible and extendable joint may have a single "flextendable" part providing both the flexing and extending functions. This may for example be a foldable and/or elastically collapsible structure, such as a bellows arrangement (as with flextendable drinking straws) or a structure with one or more collapsible coil and/or wave shapes, such as coil springs or a set of parallel meandering paths.

The two-part housing section may be formed from two tubular sections in any suitable material, i.e. a medically appropriate material. Stainless steel or nitinol may be used. In the alternative, composite materials such as carbon-fibre or glass-fibre reinforced PEEK may be used. The catheter device may be formed via a combination of such materials with the materials for different parts of the device being selected dependent on the required characteristics of those parts. A material that allows Ultrasound to pass through and at the same time have sufficient strength is preferred, Carbon reinforced PEEK meets these demands well, and would also allow Injection moulding of the components which lowers manufacturing cost. Fibre reinforced plastic are normally not visible on X-ray, so strategically placed radiopaque markers in all components may be used to determine device component(s) position and orientation on X-ray relative to each other, as complementary information to ultrasound imaging.

In some example embodiments a flextendable element is formed by providing collapsible forms into the walls of a tube made of a flexible and elastic material, such as nitinol or another shape memory metal. Laser cutting may be used to provide the required forms. The extendable and flexible joint can be cut with any suitable pattern to achieve the required functionality. For example, it may be formed as a regular (e.g. helical) spring. The extendable and flexible joint may be cut with asymmetry to achieve desired flex patterns and asymmetric forces during contact of the distal end with the wall of the heart. A thin walled silicone element is a possible alternative to a tube cut into collapsible forms. For example, a thin walled silicone tube that can be stretched many times its original length. In that case the silicon tube part may be connected to the gripper section and papillary anchor section via suitable support brackets.

The flexible and extendable joint can be extended during the procedure for insertion of the papillary anchor, as discussed further below. It can also be extended independently or be under compressive-tension prior to insertion and then be released (making the device longer, pushing the heart wall).

It is also possible to use the flexible and extendable feature individually, i.e. not in direct conjunction with the placement of the leaflet anchor. Thus, the procedure could be split into two stages, one for attaching sutures to the leaflet, and one for placing the papillary anchor. When the steps are done individually there may be advantages from using a telescopic tube to provide all or a part of the extendable function, as the device can be made shorter with that approach.

The joint may have mechanical shielding internally and/or externally to prevent wires, chordaes or tissue from getting pinched. This may be in form of a flexible membrane that stretches with the extendable joint, for example a thin sleeve that sits outside the joint. The membrane may be a silicone membrane which is fixed onto the outside of the unit above and below the joint. For example it may be fixed with adhesive. Alternatively a flexible layer of silicone (or other flexible material) could be over moulded onto the flexible joint to reduce pinch risk during movement of the joint. Fabric covering techniques similar to what is done to cover oesophageal stents or stent grafts may be applied to the joint.

In some examples using a flexible and extendable joint the joint may be covered by a tube section that extends all the way to the distal end of the catheter device when the flexible and extendable joint is compressed. This may for example be a thin walled nitinol tube. This allows the extendable joint to be completely covered during its entire travelling length. The covering tube may reduce the amount of flex in the device, therefore a further flexible section may be added just above where the covering tube is attached to the device, for example by cutting a pattern. The covering tube may be welded or glued onto the device body.

The delivery handles used by the operator to control the device may be coupled in such a way that the artificial chordae line(s) are extended when the lower section of the device is extended, in order to hold the chordae in proper tension independent on how much the lower section of the device is extended. Additionally or alternatively, a constant tension device such as a constant force spring may be disposed in the delivery handles to achieve proper tensioning of the chordae and thus remove any slack in the chordae line(s). The removal of slack from the chordae by keeping the line(s) in tension may prevent entanglement of the chordae between itself and any other components in the device.

The flexible and extendable joint can be formed in a default extended, compressed or somewhere in-between "spring configuration", to allow different means for movement/functionality. It could also be heat set partly stretched, which can allow for reduced use of material.

The leaflet anchor and/or the leaflet anchor deployment mechanism may be similar to that of WO2016/042022. Alternatively or additionally the leaflet anchor and the leaflet anchor deployment mechanism may have features as discussed below.

The papillary anchor is housed within the distal part of the housing section before its deployment. The papillary anchor may have a similar cross-section as the distal part of the housing section. For example, both may have a tubular form when the anchor is held in the distal part. As noted above the anchor may have a folded and an unfolded configuration allowing pins of the anchor to form into hooks within the body tissue during deployment of the papillary anchor. The papillary anchor deployment mechanism may take a similar form to that of WO2016/042022, and/or it may have further or alternative features as discussed below.

In one example the papillary anchor deployment mechanism includes a first wire or rod for pushing the papillary anchor in the distal direction relative to the distal part of the two-part housing section. There may additionally be a second wire or rod for releasing the papillary anchor from the papillary anchor deployment mechanism in order to disengage the papillary anchor from the catheter device after it is implanted in the body tissue, i.e. the tissue of the papillary muscle and/or tissue adjacent to the papillary muscle.

The papillary anchor may have a chordae line attached to it, and may include a locking mechanism, such as a locking ring as in WO2016/042022 and as discussed below, the locking mechanism being for clamping the chordae line when no force is applied to the locking mechanism. The locking ring may be able to be elastically deformed to release the line from the locking mechanism for adjustment of the length of the chordae line. The papillary anchor deployment mechanism may include a locking ring holder for holding the locking ring in its elastically deformed position, with the papillary anchor deployment mechanism being arranged to selectively withdraw the locking ring holder from the locking ring so that the chordae line can be locked in place after deployment of the papillary anchor and after any required adjustment of the length of the chordae line. This locking ring holder may have a Z-shape as discussed below.

The flexible joint may include a hinge element, for example with the distal part of the two-part housing section coupled to the proximal part via a pivoting mechanism or via an elastically deformable element. For example, the two parts of the housing section may be composite or metal parts coupled together by the hinge element.

In some examples the flexible joint is controllable via one or more wires, such as nitinol or stainless steel wires. There may be a wire allowing for control of the angle of the flexible joint by pushing and/or pulling. There may be three wires that are distributed in a support section in the housing section and/or attached to the flexible joint, for example to achieve a complex movement, such as where the joint is also extendable. These wires may be arranged so that when one or more wires is pushed or pulled then this will control movement of the distal part of the housing section. For example they might change the angle or extension of a flexible and extendable joint. The three wires may be arranged to be used by pushing or releasing in order to extend the device to retrieve a placed papillary anchor while still holding the leaflet in the gripper. The wires may also be arranged to be used to angle the distal part to be more perpendicular to the heart wall, for a more optimal placement of the papillary anchor. In some examples the hinge element is controllable via one or more hinge pullwires.

The hinge pullwire(s) may be of the form of the one or more wires described above. The hinge pullwire(s) configured to control the hinge element may be arranged to sit inside and/or pass through the front of the catheter device (wherein 'front' refers to the side of the catheter device shaft where the leaflet anchor deployment mechanism may be located). The hinge pullwire(s) configured to control the hinge element may also be arranged such that they are radially offset from a central axis of the catheter device, i.e. such that they are proximate a wall of the catheter device rather than a central axis of the catheter device.

When the hinge pullwire(s) configured to control the hinge element are arranged as described above, the hinge pullwire(s) may act as a deflection wire, i.e. the hinge pullwire(s) may be configured such that when the distal part of the two-part housing section is angled relative to the proximal part of the two-part housing section through the use of the hinge pullwire(s), the hinge pullwire(s) may deflect a device shaft of the catheter device in the same direction that the hinge element of the flexible joint is angled. This may have the effect of increasing the force acting on the wall of the heart during deployment of the papillary anchor from the catheter device. The actuation of the hinge element and the deflection of the device shaft may be sequential or simultaneous during operation of the hinge pullwire. For example, during operation of the hinge pullwire the device shaft may deflect at the same time the hinge element bends, or during the operation of the pullwire the hinge element may bend first and the device shaft may deflect second. Additionally, when the hinge pullwire(s) is actuated the device shaft of the catheter device may be steered in a target direction. This beneficially assists in ensuring that the distal part of the two-part housing section is perpendicular to a target wall of the heart during papillary anchor deployment.

In some examples the flexible (and optionally extendable) joint is cut with laser from an elastic tube (for example a nitinol tube), that also acts as the structural component of the entire catheter device, such that the tube also forms the distal part and proximal part of the two-part housing section. Different types of patterns can be applied to the tube edge towards the tissue to achieve different friction and/or potential "hooking" to keep the device stable during implantation, one example is a wave pattern edge or a flange with increased surface towards the tissue. To avoid pinching of the new chordae a sheath to cover the suture inside the joint can be implemented, wherein the suture sheath can be retracted/opened once the placement of the anchor is confirmed.

An example of the use of the catheter device of the second aspect may include the following steps: (1) the device is first placed in near proximity to final placement; (2) the flexible joint is angled to move the distal part toward the papillary muscle and the wires/rods along with the papillary anchor within the distal part move with it, for example due to friction between the papillary anchor (or a papillary anchor push tube) and the internal surface of the distal part of the housing section; (3) the distal end of the distal part meets the body tissue, and as force is applied the counterforce from the body tissue eventually surpasses the forces holding the papillary anchor in place, at this point tissue is pushed flat below the base of the device giving a maximal chance of placing all pins correctly in tissue, and force can be applied to the anchor so that the ends of the pins then move beyond the distal end of the distal part to meet the body tissue, this may be done via additional force on the anchor from rods or wires, or advantageously it may be done through a pre-tension on the anchor that is held by friction with the distal part until the forces from the body tissue on the distal part changes the balance of forces with the friction sufficiently so that the papillary anchor ejects (similar to a paper stapler); (4) the papillary anchor pins fold out and form into the hook shape of the unconstrained papillary anchor to thereby engage with the body tissue, at which point the connection can be pull tested by operator, and/or visually confirmed on x-ray and/or ultrasound; (5) if the connection is not satisfactory, the papillary anchor can be pulled back into the device and re-placed to attempt an improved coupling of the anchor with the body tissue. The same device may also implant the leaflet anchor, which can be done after implantation of the papillary anchor, or optionally prior to implantation of the papillary anchor. During the implantation of the papillary anchor the leaflet anchor deployment mechanism may be used to grip the leaflet, with or without deployment of the leaflet anchor.

It will be understood that the operation of the catheter device of the second aspect to implant the papillary anchor may be compared to a paper stapler, since force on the device end (when being pushed) will drive the papillary anchor out of the end and into the material adjacent the end similar to a stapler. In a typical example, once the device is in position and the leaflet is secured (for example in a gripper as in WO2016/042022, or as discussed below) then the papillary anchor can be placed, if placement of papillary anchor is approved, the leaflet anchor can be placed, if not then the leaflet might be detached and papillary anchor retrieved to be placed again. The flexible joint in the centre of the device also improves movement through the catheter, especially through arcs, as it can more easily go through curves as two shorter components connected with a flexible joint.

In some examples the actuation of the leaflet anchor can be connected to the papillary anchor deployment, meaning that the leaflet and papillary anchor may be at least partly deployed at the same time. This can make the procedure easier and/or faster.

Viewed from a third aspect the invention provides an anchor system comprising an anchor for implantation in body tissue to hold a line, the anchor comprising a number of hooks for engagement with the body tissue and having a folded configuration and an unfolded configuration, wherein the anchor is made of an elastic material such that it can be elastically deformed into the folded configuration by application of a constraining force, and will return to the unfolded configuration when no constraining force is applied, wherein the end of each of the hooks comprises a tip, and wherein the tips are formed to curve towards a central axis of the anchor when the anchor is in the folded configuration.

As it will be appreciated, for the hooks to engage with the body tissue the tip of each hook must be able to pierce the target body tissue. The end of the tip is therefore generally sharp and/or pointed. By requiring that the tips of the hooks are curved towards a central axis of the anchor when the anchor is in the folded configuration, i.e. that the very ends of the tips are spaced inwardly of some other part of the hooks, then the ends of the tips advantageously do not contact an inner surface of a container device providing the constraining force to elastically deform the anchor. For example, if the container device constraining the anchor to be in the folded configuration was a tubular device, the tips would be curved away from the inner surface of the tubular device such that the ends of the tips do not contact the inner surface. Instead, a smoother portion of the hooks will lie tangential to the inner surface and be the contact point between the hooks of the anchor and the container device. Thus, in the folded configuration the outermost portions of the anchor may be portions of the hooks spaced apart from the ends of the tips of the hooks, with the tip ends being located inward of those outermost portions and extending toward the central axis of the anchor. The tips of each of the hooks therefore are not able to scratch and/or scrape the inner walls of the container device constraining the anchor. This prevents damage to the container device, as well as avoiding the risk of shavings of the container tube material from being created, which may be undesirably deposited in the region of the target body tissue. Although a small deposition of material may seem negligible, the shavings may cause hemorrhaging and/or may cause an embolism that could result in a stroke.

The anchor may be made of an elastic metal, for example, nitinol or stainless steel, while the container device may be made of a composite material, such as a material comprising a matrix with reinforcing fibres or particles, for example, carbon reinforced (CRF) PEEK. It will be appreciated that the metal of the anchor could easily damage the composite material of the container device.

The anchor system may include the container device along with the anchor. Thus, the anchor system may comprise a container device holding the anchor in the folded configuration, wherein the tips of the anchor curve inward away from the container device. The container device may provide a constraint around an outer circumference of the folded configuration of the anchor and it may be a tubular container device as discussed above, for example a circular tube.

An additional advantage that arises by having the tips curve towards a central axis of the anchor when the anchor is in the folded configuration is that less force is required to eject the anchor from a container device during implantation in body tissue. By having a smooth point of contact between the anchor and an inner surface of the container device, the coefficient of friction between the anchor and said device is reduced. Thus less force is required to eject the anchor during implantation.

The curving of the tips towards the central axis of the anchor when the anchor is in the folded configuration may be described as at least one of, for example, a reverse curvature, an opposite curvature, or a sigmoid curvature. In other words, in the folded configuration the hooks may include a first curve portion extending towards the central axis of the anchor. The hooks and the tips may then curve away from the central axis of the anchor in a second curve portion, before the tip is formed to curve back towards the central axis of the anchor in a third curve portion. Thus the curvature of the hooks may be such that they have at least one point of inflection.

Advantageously, the curvature of the anchor assists in pulling the anchor into the body tissue during implantation and thus reduces the force required to push the anchor during implantation. As the anchor unfolds from its folded configuration to its unfolded configuration, the curvature of the anchor provides a 'springback' force, wherein the curvature of the hooks of the anchor assists in pulling the anchor through the body tissue. This advantageous effect is not exhibited by anchors having hooks which do not curve back towards a central axis of the anchor when in a folded configuration.

Anchors having hooks which do not curve back towards a central axis when in a folded configuration tend to immediately bend back into their unfolded configuration without penetrating any particular distance into the tissue, unless a large amount of axial force is applied to the anchor during implantation. However, anchors having hooks where the tips are formed to curve towards a central axis will tend to penetrate a larger distance into the body tissue before the tips begin to curve outward from the central axis as they move into their unfolded configuration. Thus a reduced axial force is required to be applied to the anchor from the container device to cause the initial penetration of the anchor, and in some cases this may be no force with the unfolding of the anchor acting to draw it into the tissue so long as a distal end of the container device is in contact with the surface of the body tissue. The springback force of the anchor resulting from the inward curvature of the tips facilitates a trajectory of the hooks of the anchor that cause the anchor to move along a deeper curve into the tissue, thereby causing the pulling effect as described.

When the anchor is in the unfolded configuration the hooks may extend away from the central axis of the anchor in a grappling hook type shape. Thus, the anchor may be configured such that when moving from the folded to the unfolded configuration the tips move outwardly away from the central axis of the anchor. In the unfolded configuration the hooks may have a curvature with at least one point of inflection, for example the direction of curvature of the hook may reverse at the tip. Thus, the unfolded configuration of the hooks may have a first curved portion with a first direction of curvature extending along the majority of the length of the hook, followed by a second curved portion with an opposite direction of curvature at the tip of the hook. This form can be used to ensure that when folded into the folded configuration the tips will curve inward toward the central axis as discussed above.

The curvature of the hooks of the anchor in its unfolded configuration as described above advantageously increases the planar extent of the anchor and thus increases the surface area covered by the anchor when unfolded. As the anchor covers a larger surface area of tissue once implanted, the force of the anchor which acts on the tissue is equally spread over a larger area. This reduces the strain on the body tissue the anchor is implanted in. This is particularly advantageous in the implantation of the anchor into lower quality or weaker body tissue.

The anchor may comprise a body portion from which the hooks extend. For example the body portion may include a tubular wall, with the hooks extending from the tubular wall such as from an end thereof. Thus, with the curve described above in the folded configuration the first curve portion may extend from the tubular wall, followed by the other curve portion(s) extending further from the tubular wall. In example embodiments the hooks extend from the body portion with a smooth curvature in both the unfolded and the folded configurations. In that case, there is no step change in the curvature at the point where the hooks join to the body portion (e.g. the tubular wall) or close to that point. The hooks may extend from the body portion with an initial curve having a tangent aligned with the axial extent of the body portion in both of the unfolded and the folded configurations. The curvature of the hooks may include no step change at all, so that it is always a continuous curve with no sharp corners.

The curvature of the tips may result in the end of each hook being configured to be perpendicular to the surface of the body tissue in the folded configuration, i.e. when the anchor is implanted in the body tissue the ends of the tips may be pressed into the body tissue to initially pierce the body tissue in a direction that is perpendicular to the surface of the body tissue. Typically this will involve at least the distal portions of the tips being parallel with a longitudinal axis of the anchor and/or parallel to a direction of movement of the anchor as it is implanted. Advantageously, by having the ends of the hooks perpendicular to the body tissue less force is required to implant the anchor in the body tissue. This is because there is a higher conversion of the force pushing the anchor into the tissue being transferred to ends of the tips, where initial implantation will occur. Moreover, by requiring that the ends of the hooks be perpendicular to the body tissue that the anchor is to be implanted in, the aligning of the anchor with the body tissue will be easier.

Similarly, the curvature of the tips may result in the tip of each hook being configured to be at an angle to the surface of the body tissue in the folded configuration, i.e. when the anchor is implanted in the body tissue the ends of the tips may be pressed into the body tissue to initially pierce the body tissue in a direction that is angled inwards to the central axis of the anchor/acute to the surface of the body tissue. Thus, the tips may curve toward the central axis and at least the end portions of the tips may extend diagonally toward the central axis, when in the folded configuration. The angle of the curvature of the tips may be any of any value in the range of 0 to 30 degrees to the normal of the surface of the body tissue that the anchor is to be implanted in. In various embodiments the range of values the curvature of the tips could take may be 0 to 5 degrees, 0 to 10 degrees, 0 to 15 degrees, 0 to 20 degrees, 0 to 25 degrees or 5 to 15 degrees. Advantageously, by having the tips of the anchor slightly angled to the body tissue less axial force is required to fully implant the anchor in the body tissue. The force may be applied to the anchor by the anchor container tube, the anchor container tube comprising a number of wires and/or rods for applying the axial force. This is because the springback force provided by the hooks of the anchor assists in pulling the anchor into the body tissue. The springback force exhibited by the hooks of the anchor is increased depending on how inwardly curved the tips of the anchor are when initially implanted into the body tissue.

Thus, it will be appreciated that a consideration of the angle of the tips to a surface of the body tissue the anchor is to be implanted in may be made to reduce the force required to implant the anchor fully in the body tissue.

The tips of the hooks may include a tapering section extending to a pointed end for piercing the body tissue. The tips may also include a widening section prior to the tapering section, with the widening section being wider than a preceding portion of the hooks. The shape of the tips of each hook may be that of a teardrop, a leaf, and/or a petal. That is, the tips may comprise a generally ovate shape comprising a pointed end for engaging the body tissue. The shape of the tip may be such that the widest portion of the tip is wider than that the width of a preceding portion of the hook, with the point being of a narrower width than that the width of the hook.

The shape of the tip being such that the tip is generally wider than the rest of the hook may advantageously assist in strengthening the engagement of the anchor with the body tissue. When tissue regrowth occurs around the implanted anchor, the tissue may regrow around the hook which extends through the body tissue. As the widest part of the tips of each hook are wider than that the width of the preceding portion the hook, more force is required to remove an implanted anchor after tissue regrowth has occurred as the shape of the tip itself forms a further anchoring feature.

It will be appreciated that the anchor of this aspect may be used as a leaflet anchor or as a papillary anchor.

The anchor may further include that the hooks are formed with openings along their length. By adding openings in the anchor hooks a larger width hook can be used thereby increasing the holding strength while still allowing significant deformation between the folded and unfolded configuration without any plastic deformation. The increased surface area of the larger width hook also aids in spreading the distribution of forces. The openings may also enhance healing by allowing tissue to growing in between the slits, making a more reliable connection between the anchor and the tissue over time, rather than the tissue forming a “sock” that may be pulled out more easily, as would be the case with a solid hook.

Advantages arise if the anchor can releasably hold a line such as a chordae line, and therefore the anchor may comprise a locking mechanism for clamping the line when no force is applied, and being able to be elastically deformed to release the line from the locking mechanism for adjustment of the length of the line. This may use a locking ring as discussed below.

In some examples the openings in the hooks include multiple holes (such as multiple holes of with a diameter of about 0.2-0.4 mm), with these openings connected with a suture, wherein a single length of suture passes through several of the multiple holes, or all of the multiple holes. The suture may be knotted at each hole. The suture may for example be a Dyneema suture (or other similar suture, such as Dacron). Elastic materials such as nitinol can be prone to fatigue fracturing during high cyclic loads, including the cyclic loads that will arise from a beating heart. By the use of a suture through multiple holes it is possible to add a failsafe to the anchor pins. If the hooks of the anchor break then the anchor is still kept together by the suture, which reduces risk for embolism while also providing extra time for ingrowth of tissue. Thus, even if an anchor breaks at an early stage then it will not embolise, and it will still be able to hold some force, as the expanded anchor will be too large to be pulled through its entry hole even if one or more hooks suffer a fracture. The use of a suture in this way will also make more “openings” for tissue to grow through. The multiple holes may be circular holes made in addition to other openings in the hooks, such as being made in addition to slits as discussed below.

As an alternative to the use of a suture threaded through the openings the anchor may include an overmolding, which may be provided about the entire anchor excluding the sharp tips of the hooks could be possible. A suitable material for such an overmoulding is ePTFE. Another alternative is to use a woven fabric pouch that encloses the anchor. Both of these solutions would keep the anchor from embolising if there is a fracture in the anchor. The use of ePTFE also gives the added benefit of tissue ingrowth.

The anchor may be formed from a tube that is cut to provide tines extending from one end of the tube, with these tines then being curved and heat set to form the hooks and tips. Openings can be cut into the tines before or after they are curved, but typically before in order that there is only one cutting stage. An added benefit of the use of openings in relation to this construction is that small diameter tubing becomes more pliable with an opening in the centre, since the arc of the tube is divided into two smaller arcs. As a result a wider section of a narrow tube can be safely utilized for making the tines which again gives additional strength. As a result of the increased holding force and increased pliability the anchor hooks are subjected to less fatigue load which in turn makes the implant last longer.

The openings may be formed as a series of holes, or as slits extending along the length of the tines to thereby extend along the curves of the hooks. A benefit of the use of slits is that each hook consists of two "legs" meaning that a fracture in one of the "legs" does not mean it will embolise, and the anchor will still be held in place by the other leg. At the same time the new "V" shape leg will highly likely grow into tissue more effectively than a straight "broken" hook without any slit or other openings, further reducing the danger of embolism.

The openings may include several smaller slits in line or have different types of pattern (zig-zag, barbed or wave pattern are examples). Along the length of the hooks, small holes with different patterns may be made, either instead of slits or in addition to slits. This can provide additional holding force, when tissue grows through the holes. It can also allow for a suture to be threaded through the hooks for added safety in the event of a fracture as discussed above. The slits may also be extended beyond the ends of the hooks where they join into the base of the anchor, which may be a tube shaped part as discussed above, thereby making the base more flexible as well. In some examples the slits may be cut as a single laser track. Circular openings can be added to the ends of such a cut to prevent high strain points.

In one example the anchor is cut from tubing made of an elastic metal, such as nitinol or stainless steel. Laser cutting may be used. This can involve cutting tines as discussed above, which can be heat set into curves. The anchor may be heat treated and/or electropolished. Chamfered edges may be introduced to the anchor on certain parts before the anchor is electropolished. The openings could contain a barbed or wave profile along edges of the openings, e.g. along edges of slits. Where slits are used the slotted hooks can be heat set in a configuration where they have increased distance when deployed. A barbed profile can then be concealed when the pins are straight (barbs are facing towards one another). With this example, when the anchor comes to a non-constrained configuration then the slits move apart and the barb profile is engaged.

In various aspects the invention extends to the use of the catheter devices and the anchors described above, and in particular to the use of those devices during a procedure for implanting an artificial chordae line into the heart. Further, the invention extends to the manufacture of the catheter devices and the anchors described above, including the various method steps discussed above such as laser cutting from tubes. For any of the anchors, or other laser cut parts discussed herein chamfered edges may be introduced before the laser cut part (e.g. anchor) is electropolished. The features of the third aspect and other optional features discussed above may be combined with the other aspects discussed above and below, with the anchors of those other aspects hence having hooks formed in accordance with the third aspect.

Viewed from a fourth aspect the invention provides a catheter device for implanting an anchor into body tissue to attach a line to the body tissue, the catheter device comprising:

a housing section extending from a distal end of the catheter device along the length of the catheter device toward the proximal end of the catheter device, the housing section comprising a distal part at the distal end of the catheter device and a proximal part located on the proximal side of the distal part;

an anchor deployment mechanism at the distal part of the housing section for deployment of the anchor for attachment of the anchor to the body tissue, wherein the anchor deployment mechanism is arranged for deployment of the anchor from a stowed position of the anchor by moving it outward in the distal direction relative to the distal part;

the anchor, which is held in its stowed position by the anchor deployment mechanism in the distal part prior to deployment, wherein the anchor is for implantation in the body tissue to hold a line, the anchor comprising a number of hooks for engagement with the body tissue and having a folded position and an unfolded position, wherein the anchor is made of an elastic material such that the hooks can be elastically deformed into the folded position by application of a constraining force, and will return to the unfolded position when no constraining force is applied, and wherein the hooks are held in the folded position whilst the anchor is in the stowed position within the distal part;

wherein the distal part of the housing has a non-circular shape for engagement with a corresponding non-circular form of the anchor and/or the anchor deployment mechanism, such that when the anchor is held in the distal part movement of the anchor is restrained with respect to rotation of the anchor about a longitudinal axis of the distal part due to engagement between the non-circular shape and the non-circular form.

With this arrangement the interaction of the non-circular shape of the distal part with the non-circular form of the anchor or anchor deployment mechanism ensures that the anchor has a required orientation whilst it is within the distal part. Rotation of the anchor is restrained and advantageously may be prevented, at least with reference to forces of a magnitude that the anchor and catheter device may be exposed to during normal use. Typically the restraint is provided by interlocking of the non-circular form in the non-circular shape, with a design tolerance in accordance with the appropriate manufacturing techniques, materials and design principles. The non-circular elements may take any shape that is not circular. Some options are discussed below. The non-circular nature of the shape/form may be achieved by modifying a circular form, such as by adapting it to be a keyed joint wherein the key or keyway contributes to the non-circular part of the shape. The catheter device may be for implanting the anchor into the heart and the anchor may be a papillary anchor for implantation into the papillary muscle, with the line for example being an artificial chordae line, such as a line used to repair the heart in the case of failing chordae tendineae. The restraint of rotation may hence be designed to resist forces that may seek to undesirably rotate the anchor during such use of the catheter device in the heart, or forces that arise when retrieving a delivered anchor, to find the correct orientation of the anchor prior to retraction. Further features of a catheter device for implantation of anchors into the heart are discussed below and it will be appreciated that the catheter device of the fourth aspect may be combined with the further features as set forth below.

The non-circular shape may be a shape formed within the interior of the distal part around a recess for housing the anchor and anchor deployment mechanism, with the anchor in the stowed position. The non-circular shape may include a funneled shape at the distal end thereof. This can allow for guided engagement of the anchor and anchor deployment mechanism. For example, the non-circular shape may widen gradually as it approaches the distal end of the distal part. The outer shape of the distal part may be a different shape, for example it may be a tubular shape with a similar form to outer parts of the remainder of the catheter device such as a circular tube. Advantageously, with the use of a different outer shape compared to the inner, non-circular shape, the wall of the distal part may vary in thickness. Alternatively or additionally the non-circular shape within the interior of the distal part may be placed eccentrically, i.e. off-centre, in order to create a varying thickness of the wall of the distal part. Thicker sections of the wall may be able to better accommodate other features of the catheter device, such as a chordae channel. By taking advantage of the varying thickness in this way then such features can be added without increasing the overall width/diameter of the catheter device. Thus, in some examples a thicker section of the wall of the distal part includes a chordae channel. The chordae channel may be a slit along the length of the distal part, which can usefully also have the function of increasing elasticity of the distal part allowing it to flex as it receives the anchor and the anchor deployment mechanism.

The anchor may include a locking mechanism with an elastically deformable locking segment as discussed further below. Alternatively, the locking mechanism may take another form, such as via parts that move in a rotational or linear sense in order to trap or restrain movement of the line, such as by an interference fit. The locking mechanism may be for locking the line in place after deployment of the anchor. The anchor deployment mechanism may be arranged to hold the locking segment in a deformed position when the anchor is stowed within the distal part, and advantageously the locking segment may adopt a non-circular form when it is in the deformed position, with this non-circular form engaging with a part of the non-circular shape of the distal part of the catheter device. Thus, this part of the non-circular shape of the distal part of the catheter device may be arranged to engage with the anchor having the deformed locking segment, wherein whilst the anchor is within the distal part the respective non-circular elements are in engagement with each other to thereby restrain rotation of the anchor within the distal part. In one example the locking segment is tubular when it is not deformed, and may align with a tubular wall of the anchor, with deformation of the locking segment moving it out of alignment with the tubular wall of the anchor and hence forming the non-circular form for engagement with the relevant part of the non-circular shape of the distal part. The anchor may have a circular tubular wall, with the deformed locking segment having a non-circular form with an ovoid shape where parts of the locking segment protrude outward beyond the tubular walls of the anchor. In that case the distal part of the catheter segment may have a corresponding ovoid cross-section, or some other non-circular cross-section for complementary fit with a cross-section of the anchor with the deformed locking segment. The distal part may hence include a first tubular recess with this non-circular cross section, where the first tubular recess is formed contiguous with a second tubular recess to house the part of the anchor wall that is located at the proximal side of the locking segment. The second tubular recess may hence have circular tubular form arranged to fit concentrically around the anchor wall proximal of the locking segment. Further optional features of a locking mechanism of the anchor are discussed below.

The anchor and/or a distal end of the distal part may be arranged to deform elastically during engagement of the anchor with the distal part in order to allow for guided engagement. Thus, the engagement of the anchor may be done with the ability to handle some misalignment by elastic flexing of the anchor and/or the distal end. The anchor may be inherently flexible due to its formation from an elastic material. The distal end may be adapted to allow for some degree of flexing, such as by the use of a slit extending from the tip along the length of the distal end in the proximal direction.

The anchor deployment mechanism may comprise an adjustment housing that holds the anchor during deployment and facilitates adjustment of a line attached to the anchor. The adjustment housing may also include a cutter for cutting of the line once the anchor has been successfully deployed in a desired location, with the line adjusted to a suitable length. In some examples an outer part of the adjustment housing has a non-circular form and a part of the non-circular shape of the distal part of the catheter device may be arranged to engage with the outer part of the adjustment housing with the respective non-circular elements in engagement with each other to thereby restrain rotation of the adjustment housing and hence assist in keeping the anchor from rotating due to attachment of the anchor to the adjustment housing whilst the anchor is within the distal part. The outer part of the adjustment housing may have a non-circular form at a proximal end thereof, i.e. opposite a distal end of the adjustment housing that couples with the anchor, with the distal part of the catheter device having a shape for receiving this non-circular form. In this case the proximal end of the adjustment housing may advantageously have a tapering shape, such as via curved, chamfered or bevelled edges, in order to allow for smooth and guided engagement of the proximal end with the corresponding part of the non-circular form for the distal part.

A shaft which may house the cutter (and a wire to operate the cutter) and the adjustment housing can be built with two lumens: one chordae (i.e. line) lumen and one cutter wire lumen. The construction may be reinforced with braid around the chordae lumen. The braid may comprise a laser cut hypotube, which increases tensile and compression strength of the shaft. The laser cut hypotube may be welded directly onto a head of the cutter. This ensures a strong bond between the cutter and the laser cut hypotube, which allows for more reliable retrieval of the papillary anchor if adjustment and/or redeployment of the anchor is required. A braided composite tubing may be disposed outside the laser cut hypotube to form the wire lumens. A Kevlar wire or a wire of a similar material may be disposed along the length of the shaft to increase the tensile strength of the shaft. The components and tubing disposed in the shaft may be embedded in a soft polymer, including but not limited to Pebax (e.g. by Pebax reflow), to allow for sufficient flexibility of the shaft. The composite tubing may also be anchored in the distal end to prevent the tubing from being torn out of the soft polymer during actuation of the cutter wire. The composite tubing may be anchored in the distal end with, for example, a flat ribbon coil, a stainless steel hypotube ring, or a collar.

The anchor and the adjustment housing may be arranged to engage with each other in a required orientation with relative rotation prevented. In this context, as above, the rotation is restrained in a twisting direction along the axis of a catheter device, i.e. the aim is to correctly orientate the anchor with respect to rotation about the longitudinal axis of the catheter device. It is however an advantage to allow for some relative rotation during engagement of the anchor with the adjustment housing in order to ensure the correct alignment without risk of jamming. Thus, the anchor and the adjustment housing may each have circular parts for concentric engagement with each other including a keyed joint to ensure correct alignment during the concentric arrangement. Thus, one of the anchor and the adjustment housing may include a key feature, with the other including a keyway for receiving the key feature. A funneled/tapering shape at the start of the keyway may be used to allow for some misalignment and guided rotation before the key feature engages with the keyway.

The distal part may have a non-circular shape that is arranged to engage with both of a non-circular form of the anchor, such as the deformed locking segment as discussed above, and a non-circular form of the adjustment housing, such as the outer part discussed above. Thus, the non-circular shape of the distal part may be a complex shape with a first part for engagement with the anchor and a second part for engagement with the adjustment housing. This can have added advantages compared to the use of each element individually since both of the two engagements contribute to restraining rotation of the anchor within the distal part. The two engagements combined can also have a further advantage through the different characteristics of the parts involved, such as a different degree of stiffness of the anchor compared to the adjustment housing, with the anchor being more easily elastically deformed; and/or a greater degree of flexibility during mating of the non-circular shape and the non-circular form, for example via a larger difference in dimensions where the non-circular form of the distal part fits around the anchor compared to where the non-circular form of the distal part fits around the adjustment housing and/or greater flexibility for the distal end of the distal part, such as through the use of a slit as mentioned above.

In some examples the anchor is formed from an elastic material with a relatively flexible configuration, such as the anchors described further below, and it is more easily elastically deformed than the adjustment housing, which may include solid parts with a less flexible configuration and/or may be formed from a less elastic material. For example, the anchor may have relatively thin walls formed of a flexible metal such as nitinol and the adjustment housing may be a solid shape and/or have thicker walls formed of a stiffer material such as stainless steel, a polymeric material, or a composite material (e.g. CRF PEEK). Thus, during the re-engagement of the anchor with the distal part the engagement of the non-circular form of the anchor with the relevant part of the non-circular shape of the distal part may be done with elastic deformation of the anchor and/or the distal end of the distal part in order to cope with a relatively high degree of rotational misalignment, whereas the re-engagement of the adjustment housing with the distal part the engagement of the non-circular form of the adjustment housing with the relevant part of the non-circular shape of the distal part.

It can be required to move the anchor back from the unfolded configuration to the folded, stowed, configuration during use, for example if an initial deployment does not give a sufficiently secure connection between the anchor and the body tissue. The catheter device may be arranged to facilitate re-engagement of the anchor and anchor deployment mechanism with the distal part by allowing for first a re-engagement of the anchor with the distal part to correct for relatively large rotational misalignment via the elasticity of the non-circular form of the anchor and/or of the distal part of the housing, and second to have a re-engagement of the outer part of the adjustment housing with the distal part to apply a greater restraint against rotation of the anchor within the distal part due to the more rigid form of the adjustment housing. The first part of the non-circular shape of the distal part of the catheter device may extend by a first distance in the distal direction from a fully stowed location of the anchor toward the distal end of the device. The second part of the non-circular shape of the distal part of the catheter device may extend by a second distance in the distal direction from a fully stowed location of the adjustment housing toward the distal end of the device. To facilitate the above two-stage re-engagement process the first distance may be larger than the second distance, with the first part hence being larger than the second distance by a third distance. In an example arrangement the first distance may be in the range 4-8 mm, whereas the second distance may be in the range 2-5 mm.

Thus, the anchor may engage elastically with the distal part over the third distance, with this then providing some correction to the alignment of the rotational orientation of the anchor before the adjustment housing engages with the second part of the distal part over the second distance. Whilst the adjustment housing engages with the second part of the distal part over the second distance the anchor progresses further along the first distance, remaining in engagement with the first part of the non-circular shape of the distal part.

The adjustment housing may form an anchor holder that connects to the anchor whilst it is stowed and during deployment and releases the anchor after successful deployment of the anchor. An outer part of the anchor holder may have a non-circular form and this may provide the above discussed non-circular form of the adjustment housing for engagement with the distal part. The anchor holder may be provided in two parts that interlock with relative rotation between these two parts being prevented by respective non-circular shapes, which may include flat surfaces for correct alignment. The two parts of the anchor holder may comprise a piston for engagement with the anchor and a piston housing for holding the piston, with the piston able to be actuated for sliding movement relative to the piston housing.

The piston may include a piston wedge for engagement with a deformable element of the anchor, which advantageously is a locking segment as mentioned above. The piston wedge may be a wedge shaped section at the distal end of the piston. The wedge-shaped section advantageously assists in engaging the locking segment and equally disengaging the locking segment due to its shape. The piston wedge may be arranged to be pushed between the locking segment and the wall of the anchor to elastically deform the locking segment, advantageously forming the non-circular form of the locking segment as well as opening the locking segment to allow for adjustment of the line. In that case, when the anchor is in the stowed position the piston wedge is engaged with the locking segment. The piston wedge may be a two-legged fork with an opening allowing for the line to pass between the two legs (tines) of the fork.

The piston wedge may be engaged with the locking segment without being in contact with any other wall of the papillary anchor. Thus, the anchor holder and the anchor may be arranged such that when the piston wedge is engaged then it is spaced apart from the wall of the anchor. By advantageously requiring that the piston wedge is in contact with the locking segment of the anchor alone, and not any other wall of the anchor, the piston wedge experiences less friction from the anchor. As such, during deployment of the anchor from the catheter device, the anchor may deploy without the piston wedge moving with the anchor to thus ensuring the locking of the locking segment. The placement of the piston in the anchor holder acts as a cantilever, which prevents the piston wedge from being pulled towards the wall of the anchor due to the elastic force of the locking segment. The piston and hence the piston wedge may be made of a suitably rigid material, such that the piston wedge is not bent out of shape by the reaction force due to the cantilever action of the piston and the force exerted on the piston wedge by the locking segment acting in opposite directions.

The piston may include the cutter of the adjustment housing, with this cutter being arranged to cut the line when the piston is withdrawn from the anchor. The cutter on the piston may be a cutting surface arranged to interact with a surface of the piston housing to cut the line, such as via a shearing action. Thus, where a piston wedge is used then the withdrawal of the piston may allow the line to be locked in place at the anchor as the locking segment returns to its undeformed position and clamps the line to the anchor wall, whilst the line is simultaneously cut by the cutter. In this way the piston aids in an adjustment and cutting procedure once the anchor is correctly placed and the length of the line is as required.

An internal cam may be provided for aiding in holding the anchor locking segment in an open position. The internal cam may have an unexpanded configuration where the cam fits inside the locking segment in the undeformed state of the locking segment, and an expanded configuration where the cam fits inside the locking segment in the deformed state, i.e. the non-circular form discussed above. The cam may have an opening at its centre that is wider in the expanded configuration than in the unexpanded configuration. The piston may be provided with a cam wedge for urging the opening of the cam to the wider state and hence expanding the cam. The cam wedge may be provided in addition to the piston wedge discussed above, so that a single piston has a fork like form at its distal end, with at least one tine of the fork providing the cam wedge and at least one tine of the fork providing the piston wedge. The cam may be arranged aid opening of locking segment and it may also act to fix the anchor to the adjustment catheter, where present. The cam may be held in place by a cam holder on the adjustment housing.

The catheter device may include a mechanism for control of movement of the adjustment housing relative to the distal part, for example to push the adjustment housing and the anchor outward from the distal part in the distal direction to deploy the anchor. This mechanism may include an adjustment catheter located within the housing of the catheter device, where the adjustment catheter can be moved forward or backward along the length of the catheter device in order to advance or retreat the adjustment housing. Wires and/or rods may be used to control movement of the adjustment housing, with manual or computer controlled movement via control system arranged to be placed outside of the body.

The catheter device may include a mechanism for control of movement of the piston relative to the piston housing. This may include wires and/or rods of suitable type. The mechanism may be arranged to slide the piston outward from the piston housing in order to move the anchor away from the piston housing. The mechanism may be further arranged to draw the piston back into the piston housing to either disengage the piston from the anchor or to draw the anchor back toward the piston housing along with the piston. It will be appreciated that to complete the deployment of the anchor after the line has been suitably placed and adjusted then the piston should withdraw from the anchor to disengage therefore, such as by removing the wedge from the locking segment, where present. However, if it is determined that the anchor is not placed correctly then the user may decide to draw the anchor back toward the piston housing in order to then pull the anchor along with the adjustment housing back into the distal part to withdraw the anchor from the body tissue and fold the hooks back into the folded, stowed position.

To prevent the cutter from exceeding its desired range of motion, the cutter may be equipped with two stopping features disposed at an upper and lower end of the cutter. To prevent the cutter from moving further than its upper position in the housing, a cutter wire may be threaded through the housing and/or the cutter to stop the cutter in an upper position. Even if the cutter wire were to break, the cutter and a wire attached to the cutter operating it cannot escape from an upwards end of the housing as both are contained within the housing. To prevent the cutter from moving further than its lower position in the housing, a cam or the internal cam may function as the lower position stopping feature.

The adjustment housing may include a latch for engagement with the housing section of the catheter device in order to prevent movement of the adjustment housing relative to the catheter device, and this may be for providing a secure state where the anchor cannot be released. Such a secure state can be beneficial whilst the catheter device is being steered to the deployment position, such as being steered through a blood vessel to reach the heart as in the examples below. The latch may be pivoted about an axis extending along the longitudinal axis of the catheter device in order to allow it to swing into and out of engagement with the housing section, for example with engagement into a recess or slot formed in the housing section. A wire or rod may be included for actuation of the latch, such as a wire that blocks movement of the latch to keep the secure state until the wire is removed. The latch may be sprung and biased toward a disengaged position, so that when the wire is removed and the latch is released it moves under the influence of a spring force into the disengaged position.

In some examples, the anchor is provided with a locking mechanism that clamps the chord when no force is applied, and that can be elastically deformed to release the chord for adjustment of the length of the chord during implantation thereof. As noted above, the locking mechanism may comprise a resiliently deformable locking segment. The locking segment may be formed in a wall of the anchor and divided from the wall by one or more slit(s). The anchor may be arranged so that when no forced is applied then the slits are closed with no gap or a relatively narrow gap in order to clamp the line, whereas when a suitable force is applied to the locking segment and/or wall then the locking segment and/or the wall will elastically deform to widen the opening provided by the slit(s) so that the line is released. The anchor may have a tubular body section, in which case the locking segment may be formed in the wall of the tube. The locking segment may be a band with parallel slits on two sides, such that the band can be pulled out of plane with the wall by application of a force in order to open up the slits. Advantageously, this movement of the locking segment may create the non-circular form for the anchor. Such a locking segment can be held open by sliding a holder into the slit(s), such as the piston discussed above.

The housing section may be formed from one or more tubular sections in any suitable material, i.e. a medically appropriate material. Stainless steel or nitinol may be used. Polymeric materials are also an option. In the alternative, composite materials such as carbon-fibre or glass-fibre reinforced PEEK may be used. The catheter device may be formed via a combination of such materials with the materials for different parts of the device being selected dependent on the required characteristics of those parts. A material that allows ultrasound to pass through and at the same time have sufficient strength is preferred, carbon reinforced PEEK meets these demands well, and would also allow injection moulding of the components which lowers manufacturing cost. Fibre reinforced plastics are normally not visible on X-ray, so strategically placed radiopaque markers in all components may be used to determine device component(s) position and orientation on X-ray relative to each other, as complementary information to ultrasound imaging.

As mentioned above the catheter device may be for implanting the anchor into the heart and the anchor may be a papillary anchor for implantation into the papillary muscle, with the line for example being an artificial chordae line. The catheter device may also be arranged for implanting a leaflet anchor along with the papillary anchor into the heart as part of a procedure for implanting an artificial chordae line that extends between the leaflet anchor and the papillary anchor. Thus, the catheter device may further include the leaflet anchor and a leaflet anchor deployment mechanism.

Thus, the housing section may be a two-part housing section, the two-part housing section being arranged to be placed between the papillary muscle and a leaflet of the heart during use of the catheter device, and the two-part housing section comprising a distal part at the distal end of the catheter device and a proximal part located on the proximal side of the distal part; wherein the distal part holds the papillary anchor deployment mechanism, i.e. the anchor and adjustment housing as discussed above, and the proximal part holds the leaflet anchor deployment mechanism.

The leaflet anchor and/or the leaflet anchor deployment mechanism may be similar to that of WO2016/042022. Alternatively or additionally the leaflet anchor and the leaflet anchor deployment mechanism may have features as discussed below.

An example of the use of the catheter device of the fourth aspect may include the following steps: (1) the device is first placed in near proximity to final placement; (2) the distal part is moved toward the body tissue that is to receive the anchor; (3) the distal end of the distal part meets the body tissue, and as force is applied the counterforce from the body tissue eventually surpasses the forces holding the anchor in place, at this point tissue is pushed flat below the base of the device giving a maximal chance of placing all hooks of the anchor correctly in tissue, and force can be applied to the anchor so that the ends of the hooks then move beyond the distal end of the distal part to meet the body tissue, this may be done via additional force on the anchor and/or the anchor deployment mechanism from rods or wires, or advantageously it may be done through a pre-tension on the anchor that is held by friction with the distal part until the forces from the body tissue on the distal part changes the balance of forces with the friction sufficiently so that the anchor ejects (similar to a paper stapler); (4) the anchor hooks fold out and form into the hook shape of the unconstrained anchor to thereby engage with the body tissue, at which point the connection can be pull tested by operator, and/or visually confirmed on x-ray and/or ultrasound; (5) if the connection is not satisfactory, the anchor can be pulled back into the device and re-placed to attempt an improved coupling of the anchor with the body tissue.

Viewed from a fifth aspect, the invention provides a method of use of the catheter device of the fourth aspect for implanting an anchor into body tissue, the method comprising: deployment of the anchor into the body tissue using the anchor deployment mechanism. The method may advantageously include testing the connection of the anchor before disengagement of the anchor from the anchor deployment mechanism and from the catheter device. In the case of an unsatisfactory deployment of the anchor the method may include withdrawing the anchor from the body tissue and moving the anchor along with the anchor deployment mechanism back into the distal part, with the non-circular shape of the distal part coming into engagement with a corresponding non-circular form of the anchor and/or the anchor deployment mechanism in order that the anchor is in the correct orientation once it is back in its stowed configuration within the distal part. This method may include use of a device with any of the other features discussed below in connection with the other device and method aspects of the present disclosure.

Viewed from a sixth aspect the invention provides a catheter device for implanting a leaflet anchor during a procedure for implanting an artificial chordae line into the heart, the catheter device comprising: a leaflet anchor for attachment to the leaflet of the heart; and a leaflet anchor deployment mechanism for deploying the leaflet anchor; wherein the leaflet anchor deployment mechanism allows for retraction and repositioning of the leaflet anchor after deployment of the anchor into the leaflet via an ejector unit having a grasping device with a first configuration arranged to permit deployment of the leaflet anchor into the leaflet without disengagement of the leaflet anchor from the ejector unit, and a second configuration in which the leaflet anchor is reversibly released from the ejector unit; wherein in the first configuration the grasping device of the ejector unit grasps a proximal end of the leaflet anchor, whilst a distal end of the leaflet anchor is unimpeded by the grasping device to enable it to be implanted in the leaflet; and wherein in the second configuration the grasping device of the ejector unit is disengaged from the leaflet anchor.

The leaflet anchor may be retracted with a retraction tube/catheter, by pulling the chordae so the leaflet anchor folds inside the retraction tube. The retraction tube may be placed on top of a chordae only attached to the leaflet (with device removed) or a leaflet anchor placed in a poor location (partly engaged, free floating, entangled etc.). The retraction tube may be a deflectable shaft, with or without a flexible section on the tip (that allows the tip to find the leaflet anchor base, to allow retraction). Alternatively the retraction shaft may be a flexible tube that is arranged to engage with the base of the leaflet anchor. In either configuration a marker band in the tip is needed to confirm that the retraction tube is at the base of the leaflet anchor, prior to applying tension to the chordae, to prevent any unwanted damage to the implant or native tissue.

Another alternative to retract the leaflet anchor when it is free floating (not attached to anything) is to tension the chordae until the leaflet anchor can be folded inside the papillary anchor housing, either in the distal end or through an opening in the papillary anchor housing wall.

As will be seen from review of WO2016/042022, in this earlier proposal the leaflet anchor is pushed out once the gripper of the leaflet anchor deployment mechanism holds the leaflet and after being pushed out the leaflet anchor cannot be retrieved with the same mechanism. Whilst it is possible to retrieve the leaflet anchor with the device of WO2016/042022, there is only one relatively complex way described to do this, and it involves a separate retrieval catheter. With the catheter device of the sixth aspect, in order to give the physician additional control, an "ejector unit" is introduced that allows for the leaflet anchor deployment mechanism to deploy and also retrieve the leaflet anchor.

It will be appreciated that the features of the device of the sixth aspect may be combined with those of the second aspect, thereby achieving the advantage of each. Moreover, there is synergy in this combination since the ability to remove and replace the leaflet combines with the benefits of the ability to keep the catheter device in place at the leaflet whilst the papillary anchor is inserted via use of the flexible and optionally extendable joint. This allows for the surgeon maximum flexibility in terms of insertion of the two anchors and checking of the connections before any significant motion of the device is needed away from its position at the leaflet anchor. The device may also be moved from the leaflet anchor placement position to accommodate papillary anchoring position or the other way around.

The telescopic shaft that holds the device may be fitted with 4 pullwires, so that the distal tip can move in order to locate correct valve position for placing the anchor(s).

The leaflet anchor may be formed from a flexible material with a hooked shape in an unfolded configuration, and being able to deform elastically into a folded configuration, for example when constrained by the leaflet anchor deployment mechanism. The material of the leaflet anchor may be nitinol. The shape of the leaflet anchor may include hooks that are straightened out when the leaflet anchor is in the folded configuration. The hooked shape of the unfolded configuration may be a grapple hook shape, for example. The leaflet anchor may have a similar form to that of WO2016/042022 and/or may have features as described below. In example embodiments, the leaflet anchor and leaflet anchor deployment mechanism may be arranged such that the when the leaflet anchor is pushed out of the leaflet anchor deployment mechanism then this can drive the hooks though the leaflet whilst the hooks return elastically to the unfolded configuration, thereby securing the leaflet anchor in the leaflet.

In example devices the chordae sits inside a groove in the device, after the leaflet anchor is placed, and applying tension (shortening) of the chordae may be used in order to release the chordae from the groove it sits in. Removing slack in the system can reduce the chance of the chordae wrapping around the device, creating complication. An example of a device to reduce slack may be some sort of constant tension device, such as a constant force spring. The constant tension device may be disposed in a delivery handle of the device.

The ejector unit may be placed within the leaflet anchor deployment mechanism inboard of the leaflet anchor. With this arrangement, when the ejector unit and leaflet anchor are within the leaflet anchor deployment mechanism then the ejector unit holds the leaflet anchor with the grasping device in the first configuration. The leaflet anchor deployment mechanism can deploy the anchor to implant it in the leaflet. In example embodiments, the grasping device may be arranged to remain in the first configuration during this deployment, with the ejector unit being arranged so that it moves to the second configuration only after the leaflet anchor is implanted. With the leaflet anchor implanted the grasping device can be used to test the connection of the anchor to the leaflet, by a force being applied to the leaflet anchor from the ejector unit whilst the grasping device is in the first configuration. Another way to test the connection is to assess leaflet movement compared to the blood flow, with the leaflet attached to the leaflet anchor and thereby held to the catheter device, i.e. before the leaflet anchor is released. If the leaflet anchor is well-engaged then the movement of the leaflet will be more restricted than if it is not well-engaged. Subsequently, with the ejector unit moved into the second configuration, the grasping device of the ejector unit opens and at this point the physician may further test the connection of the anchor to the leaflet, for example via tension applied to the chordae line. If the physician is not satisfied (for example, if there is too much movement of the anchor and/or not enough resistance to force on the line) then the leaflet anchor can be retracted and placed in another location. If the grasping device did not change from the first configuration during the test then the latter procedure may be carried out by reversing the deployment of the ejector unit and leaflet anchor, for example by drawing those parts back into the leaflet anchor deployment mechanism. If the second configuration was used before it was determined that the connection of the anchor was not adequate then to retract the anchor the ejector unit is first moved back to the first configuration so that the grasping device reengages with the leaflet anchor, and then after that the deployment of the ejector unit and leaflet anchor is reversed, for example by drawing those parts back into the leaflet anchor deployment mechanism.

The use of the device of the sixth aspect reduces the risk of a badly connected leaflet anchor requiring the procedure to be aborted and started over, and this reduced risk has clear benefits for the efficiency of the procedure as well as for the health of the patient. In addition the retractable feature may allow the physicians to load and reload the catheter device with leaflet anchors more easily. A reloading operation can be necessary if multiple chordae lines are needed to be placed in a single surgical procedure. The method steps during assembly of the device will also be improved.

In some examples, both of the leaflet anchor and the ejector unit are housed inside a leaflet anchor tube of the leaflet anchor deployment mechanism prior to deployment, with the ejector unit further inside the leaflet anchor deployment mechanism than the anchor. The leaflet anchor tube may have a shape that is complementary to the shape of the leaflet anchor, i.e. with a similar cross-sectional shape. In some examples both of the leaflet anchor and the tube both have a circular cross-section with the leaflet anchor in the deformed configuration and placed into the tube. As discussed above the leaflet anchor may unfold into a hooked shape, in which case it may comprise hooks extending from a tubular body section. The ejector unit may also have a shape that is complementary to the shape of the leaflet anchor, i.e. with a similar cross-sectional shape, and this may hence also be a circular cross-section.

The leaflet anchor tube has an opening that can be directed toward the leaflet. This opening may not be at a distal end of the catheter device as a whole. In fact the opening of the leaflet anchor tube may advantageously be directed toward the proximal end of the catheter device, in order that the leaflet anchor may easily be inserted through the leaflet from the bottom of the leaflet, as is required for effective implantation of an artificial chordae line that extends from the leaflet anchor to a papillary anchor at the papillary muscle. The leaflet anchor tube may be within a gripper arrangement as disclosed in WO2016/042022 and/or may have features as described below. Thus, the leaflet anchor deployment mechanism may include a gripper for gripping the leaflet during deployment of the leaflet anchor. It can provide advantages if the catheter device combines the proposed ejector unit of this aspect with a gripper that is different to WO2016/042022 as discussed below, i.e. wherein the leaflet anchor is deployed with the gripper at an angle to the main body of the catheter device.

With arrangements using a leaflet anchor tube, the leaflet anchor may be arranged to be deployed by advancing both the leaflet anchor and the ejector unit along the tube, with the leaflet anchor having pins at its distal end that form into the hooks of a hooked shape as the pins leave the opening of the leaflet anchor tube. This can be done whilst the leaflet is gripped in a gripper of the leaflet anchor deployment mechanism as discussed above. As noted above, once the leaflet anchor is implanted then the connection can be tested in relation to position and holding strength. If needed then the leaflet anchor can be pulled back into the leaflet anchor tube to release it from the leaflet. If the connection of the anchor is acceptable then the ejector unit may be advanced further in order that the leaflet anchor is released.

Thus, in some examples, the change from the first configuration to the second configuration may be actuated by movement of the ejector unit along the leaflet anchor tube, for example by permitting the grasping device to open when it reaches a certain position in the tube. In one example the ejector unit has a constrained configuration as the first configuration, and a non-constrained configuration as the second configuration. In the first configuration the ejector unit holds the leaflet anchor with the grasping device, which may for example comprise two or more grappling hooks arranged to engage with the leaflet anchor at their ends. In one possible arrangement the grappling hooks have ends that engage with holes formed in the leaflet anchor, preferably a proximal end of the leaflet anchor with respect to the distal direction along the leaflet anchor tube. The grasping device may engage and disengage from the leaflet anchor via a radial movement relative to the leaflet anchor tube. Thus the constrained, first, configuration may involve walls of the leaflet anchor tube preventing an outward radial movement of the grasping device (such as of the grappling hooks) in order to force the ejector unit to remain engaged with the leaflet anchor. In the non-constrained, second, configuration grasping device releases the leaflet anchor, for example via the grappling hooks moving apart. The transition from the first configuration to the second configuration may occur by movement of the ejector unit to a point at which a constraint from the walls of the leaflet anchor tube is removed, so that the grasping device opens, for example by an outward radial movement of the grappling hooks. This may be due to a movement of parts of the ejector unit out of the leaflet anchor tube, i.e. out of the opening at the tube's distal end, or it may arise by movement of parts of the ejector unit to align with cut-outs in the walls of the leaflet anchor tube.

The movement of the leaflet anchor and ejector unit within the leaflet anchor deployment mechanism, for example along the leaflet anchor tube described above, can be actuated by wires and/or rods. A wire may be provided for pulling the ejector unit for retraction of the ejector unit. Retraction of the ejector unit may be required either after a successful implantation of the leaflet anchor or as part of a retraction of the leaflet anchor to allow it to be re-implanted. Since the leaflet anchor tube may be directed toward the proximal end of the catheter device, as discussed above, such that the retraction of the ejector unit requires a pulling force toward the distal end of the device, then the wire for retraction may pass around a pulley or the like. A rod may be used for deployment of the leaflet anchor, i.e. for moving the ejector unit together with the leaflet anchor along the leaflet anchor tube toward the opening at the tube's distal end. To allow for a pushing force directed toward the proximal end of the catheter device then the rod may be a U-rod. This may be arranged as described in WO2016/042022. A rod for deployment may also be capable of applying a pulling force for retraction and hence a rod may be used alone. Alternatively, the rod may be used for deployment with a wire as discussed above being used for retraction. In another alternative the ejector unit can be moved by two wires and pulleys providing for movement in both directions. The U-rod may be produced form a heat set or bent wire. With one or more bend(s) to make the U shape and the shape that pushes on the leaflet anchor.

A groove may be provided in a wall of the leaflet anchor tube for guiding the ejector unit. The groove may ensure that the ejector unit remains a single orientation relative to the tube while it is moved up and down. The groove may alternatively or additionally set maximum limits on the range of movement of the ejector unit, and thus may prevent it from going too far in either direction, out of or into the leaflet anchor tube. The ejector unit may be provided with a guide pin for engagement with the groove. Advantageously, a narrowing in the groove may be provided to act as an indicator to let the operator know when the ejector unit has reached a certain position. The size of the guide pin and the width of the narrowing may be set so that engagement of the pin with the narrowing in the groove will require an increased force before further movement can be made, thus providing tactile feedback to the operating physician.

In one example a force feedback mechanism, such as the narrowing, is provided in order to signify that the leaflet anchor has been moved to the deployed position, but that the ejector unit is still in the first configuration so that the anchor is still retractable. In this case, once the ejector unit is pushed further (e.g., so that the guide pin is beyond the narrow section) then the ejector unit may move to the second configuration so that the leaflet anchor will be released from the ejector unit. Thus, in one example constrained parts of the ejector unit, such as the grappling hooks discussed above, may be released from their constraint once there is movement beyond a point of actuation of the force feedback mechanism, such as when the guide pin passes the narrowing in the example above. Alternatively or additionally there may be feedback mechanisms in the operation handles of the catheter device that can indicate the position of the ejector unit, for example by varying forces or by visual indicators. In an alternative to a guide pin and narrowing groove system another form of force feedback mechanism may act on the guide pin, for example a "shear-pin" suture that breaks at a given point with a given load.

The leaflet anchor deployment mechanism may include a line pusher for directing a line out of and away from the leaflet anchor deployment mechanism during deployment of the leaflet anchor. When the device is in use there may be a line attached to the leaflet anchor. The line may be provided to form the artificial chordae line after the leaflet anchor is implanted, or to allow the artificial chordae line to be attached to the leaflet anchor. The line may be a suture such as a Goretex ePTFE suture. The line pusher advantageously directs the line away from the leaflet anchor deployment mechanism so that it can be more readily accessed for later manipulation, such as for tightening the line or for pulling on the implanted leaflet anchor for testing of the connection. The line pusher may be actuated during the action of deployment of the leaflet anchor, and in some examples it is actuated when the leaflet anchor is released from the ejector unit. Thus, the line pusher may be released when the ejector unit withdraws away from the implanted leaflet anchor. The line pusher may transition from a constrained state to a non-constrained state in a similar way to the grappling hooks described above, and thus it may move radially outward to push the line out, with this radially outward movement being permitted and the line pusher released once a constraint is removed. The constraint may be from the leaflet anchor, and thus the constraint may be removed, when the ejector unit is pulled back into the leaflet anchor deployment mechanism. In that case the line pusher may be an arm that extends axially forward from the ejector unit toward the leaflet anchor, and radially outward of the leaflet anchor tube when the arm is at rest with no forces applied. Prior to deployment of the leaflet anchor the arm of the line pusher is bent elastically to place its distal end within the leaflet anchor, so that it is constrained and cannot move to its radially outward position until the leaflet anchor and the ejector unit move apart. In some examples, as the ejector unit continues to withdraw into the leaflet anchor deployment mechanism the line pusher may remain in its unconstrained state with the line pusher as well as the line being pushed out of a slit in the leaflet anchor deployment mechanism, such as a slit along the leaflet anchor tube.

The catheter device of the sixth aspect may further be provided with a papillary anchor and papillary anchor deployment mechanism for deployment of a papillary anchor for attachment to the papillary muscle. The papillary anchor deployment mechanism may be arranged for deployment of the papillary anchor by moving it outward in the distal direction relative to the distal part. The papillary anchor deployment mechanism may be arranged within a two-part housing section as discussed above with reference to the second aspect, in which case the leaflet deployment mechanism may be in the proximal part of the two-part housing section. Alternatively, the papillary anchor deployment mechanism may be similar to that described in WO2016/042022. In some examples the actuation of the leaflet anchor may be connected to the papillary anchor deployment, meaning that the leaflet and papillary anchor may be arranged to be at least party deployed at the same time, for example being actuated by a single control wire or rod. This can make the procedure easier and/or faster.

The papillary anchor deployment mechanism may include a lock that prevents the papillary anchor from ejecting too early, which may happen if the outer shaft that holds the device is compressed, while the inner papillary anchor deployment shaft is stretch or keeps it original length while the outer shaft is shortened, pushing the papillary anchor out of its housing. The lock may be a flip out tab that holds the anchor adjustment and ejector mechanism in place, the tab may be operated with a torque, push or pull wire or a suture. The actuation wire/suture may be routed through the gripper housing and supported there or supported in the papillary housing, alternatively anchored in the anchor deployment mechanism itself. In a second configuration the locking mechanism may sit inside the papillary anchor deployment mechanism and be actuated by a wire that goes inside the adjustment catheter. As noted above, wire(s) and/or a rod can be used to deploy and/or retract the ejector unit. In another variation the ejector unit may be moved via a sliding sheath that engages with a lug on the ejector unit. This sheath may fit around the leaflet anchor tube. The sheath may be a partial tube, such as a three quarter tube, that goes around the leaflet anchor tubing. Such an arrangement may also be called “sledge”, or a “linear motion bearing”. The sheath when moved will push on the lug of the ejector unit. The sheath may be actuated by one or more wire(s) or rod(s), which may be connected with a rotational joint to the sheath. For example, there may be one or more wires that can be pulled or pushed by the operator. Nitinol wires may be used. When pulled or pushed the sheath translates along the outside of the leaflet anchor tube, for example to move towards the opening of the tube and push the ejector unit via the lug. The lug may be the guide pin in the groove as discussed above.

The ejector unit and/or the leaflet anchor may be produced from an elastic metal, such as nitinol. The ejector unit and/or the leaflet anchor may be laser cut, heat set and electropolished metal tubing. The guide pin and/or lug, where present may be welded into place after assembly, such as by laser welding. The grappling hooks of the ejector unit may be heat set or laser welded in place, and they may have any suitable shape for engagement with the leaflet anchor. The leaflet anchor tube may be attached to the leaflet anchor deployment mechanism, such as attachment to the gripper, by welding, soldering or gluing, or it could be cut from a solid piece via subtractive manufacturing. Additive manufacturing techniques might also be used. Additional tubes may also be provided next to the leaflet anchor tube, for example to provide fluid flow or for covering wires. At the end of the leaflet anchor tube there may be a gripper tip that extends laterally around the leaflet anchor tube to form a gripping platform that fits with an opposing gripper element of the leaflet anchor deployment mechanism. The gripping platform may be formed by filling an end of the gripper with resin. The leaflet anchor tube may have a lever arm attached, such as a heat set (or squashed) flat section or a bent section, wherein the lever arm stretches past a rotation axis (the rotation axis may move during the gripper arms movement) of the gripper to attach wires used to open and/or close the gripper.

The leaflet anchor tube may be laser-welded to a gripper tube section, inside the chordae slit. Further features of possible gripper arrangements may be similar to those disclosed in WO2016/042022 and/or may be as set out below.

Viewed from a seventh aspect present invention provides an anchor for implantation in body tissue to hold a line, the anchor comprising a number of hooks for engagement with the body tissue and having a folded position and an unfolded position, wherein the anchor is made of an elastic material such that it can be elastically deformed into the folded position by application of a constraining force, and will return to the unfolded position when no constraining force is applied, and wherein the hooks are formed with openings along their length.

It will be appreciated that the anchor of this aspect may be used as a leaflet anchor or as a papillary anchor. By adding openings in the anchor hooks a larger width hook can be used thereby increasing the holding strength while still allowing significant deformation between the folded and unfolded position without any plastic deformation. The increased surface area of the larger width hook also aids in spreading the distribution of forces. The openings may also enhance healing by allowing tissue to growing in between the slits, making a more reliable connection between the anchor and the tissue over time, rather than the tissue forming a “sock” that may be pulled out more easily, as would be the case with a solid hook.

It will be appreciated that the anchor of this aspect, as well as providing its own advantages, may also combine synergistically with the catheter devices of the aspects described above. Thus, anchors having hooks with openings may be used for the leaflet anchor and/or the papillary anchor of the above aspects.

Advantages arise if this anchor can releasably hold a line such as a chordae line, and therefore the anchor may further comprise a locking mechanism for clamping the line when no force is applied, and being able to be elastically deformed to release the line from the locking mechanism for adjustment of the length of the line. This may use a locking ring as discussed below.

In some examples the openings in the hooks include multiple holes (such as multiple holes of with a diameter of about 0.2-0.4 mm), with these openings connected with a suture, wherein a single length of suture passes through several of the multiple holes, or all of the multiple holes. The suture may be knotted at each hole. The suture may for example be a Dyneema suture (or other similar suture, such as Dacron). Elastic materials such as nitinol can be prone to fatigue fracturing during high cyclic loads, including the cyclic loads that will arise from a beating heart. By the use of a suture through multiple holes it is possible to add a failsafe to the anchor pins. If the hooks of the anchor break then the anchor is still kept together by the suture, which reduces risk for embolism while also providing extra time for ingrowth of tissue. Thus, even if an anchor breaks at an early stage then it will not embolise, and it will still be able to hold some force, as the expanded anchor will be too large to be pulled through its entry hole even if one or more hooks suffer a fracture. The use of a suture in this way will also make more "openings" for tissue to grow through. The multiple holes may be circular holes made in addition to other openings in the hooks, such as being made in addition to slits as discussed below.

As an alternative to the use of a suture threaded through the openings the anchor may include an overmolding, which may be provided about the entire anchor excluding the sharp tips of the hooks could be possible. A suitable material for such an overmoulding is ePTFE. Another alternative is to use a woven fabric pouch that encloses the anchor. Both of these solutions would keep the anchor from embolising if there is a fracture in the anchor. The use of ePTFE also gives the added benefit of tissue ingrowth.

The anchor may be formed from a tube that is cut to provide tines extending from one end of the tube, with these tines then being curved and heat set to form the hooks. Openings can be cut into the tines before or after they are curved, but typically before in order that there is only one cutting stage. An added benefit of the use of openings in relation to this construction is that small diameter tubing becomes more pliable with an opening in the centre, since the arc of the tube is divided into two smaller arcs. As a result a wider section of a narrow tube can be safely utilized for making the tines which again gives additional strength. As a result of the increased holding force and increased pliability the anchor hooks are subjected to less fatigue load which in turn makes the implant last longer.

The openings may be formed as a series of holes, or as slits extending along the length of the tines to thereby extend along the curves of the hooks. A benefit of the use of slits is that each hook consists of two "legs" meaning that a fracture in one of the "legs" does not mean it will embolise, and the anchor will still be held in place by the other leg. At the same time the new "V" shape leg will highly likely grow into tissue more effectively than a straight "broken" hook without any slit or other openings, further reducing the danger of embolism.

The openings may include several smaller slits in line or have different types of pattern (zig-zag, barbed or wave pattern are examples). Along the length of the hooks, small holes with different patterns may be made, either instead of slits or in addition to slits. This can provide additional holding force, when tissue grows through the holes. It can also allow for a suture to be threaded through the hooks for added safety in the event of a fracture as discussed above. The slits may also be extended beyond the ends of the hooks where they join into the base of the anchor, which may be a tube shaped part as discussed above, thereby making the base more flexible as well. In some examples the slits may be cut as a single laser track. Circular openings can be added to the ends of such a cut to prevent high strain points.

In one example the anchor is cut from tubing made of an elastic metal, such as nitinol. Laser cutting may be used. This can involve cutting tines as discussed above, which can be heat set into curves. The anchor may be heat treated and/or electropolished. Chamfered edges may be introduced to the anchor on certain parts before the anchor is electropolished. The openings could contain a barbed or wave profile along edges of the openings, e.g. along edges of slits. Where slits are used the slotted hooks can be heat set in a configuration where they have increased distance when deployed. A barbed profile can then be concealed when the pins are straight (barbs are facing towards one another). With this example, when the anchor comes to a non-constrained configuration then the slits move apart and the barb profile is engaged.

In various aspects the invention extends to the use of the catheter devices and the anchors described above, and in particular to the use of those devices during a procedure for implanting an artificial chordae line into the heart. Further, the invention extends to the manufacture of the catheter devices and the anchors described above, including the various method steps discussed above such as laser cutting from tubes. For any of the anchors, or other laser cut parts discussed herein chamfered edges may be introduced before the laser cut part (e.g. anchor) is electropolished.

Viewed from a eighth aspect, the invention provides a method of use of the catheter device of the second aspect for implanting both of a leaflet anchor and a papillary anchor into the heart during a procedure for implanting an artificial chordae line that extends between the leaflet anchor and the papillary anchor, wherein the method comprises: deployment of the leaflet anchor into the leaflet using the leaflet anchor deployment mechanism; angling the flexible joint in order to bring the papillary anchor deployment mechanism into close proximity with the papillary muscle (optionally, alternatively or additionally, extending the joint if it is extendable); and deployment of the papillary anchor into the papillary muscle using the papillary anchor deployment mechanism. This method may include use of a device with any of the other features discussed above with reference to any of the various device aspects, and/or method features as discussed below. The method may include testing the connection of the leaflet anchor prior to deployment of the papillary anchor, such as via testing as discussed above.

Viewed from a ninth aspect, the invention provides a method of use of the catheter device of the sixth aspect for implanting a leaflet anchor into the heart during a procedure for implanting an artificial chordae line, the method comprising: deployment of the leaflet anchor into the leaflet using the leaflet anchor deployment mechanism with the ejector unit initially remaining in its first configuration; and later movement of the ejector unit into the second configuration to thereby release the leaflet anchor. The method may advantageously include testing the connection of the leaflet anchor before moving the ejector unit from the first configuration to the second configuration, such as via testing as discussed above. The method may include, if the connection of the leaflet anchor is found to be inadequate, keeping the ejector unit in the first configuration, withdrawing the leaflet anchor into the leaflet anchor deployment mechanism using the ejector unit and later re-deploying the leaflet anchor using the leaflet anchor deployment mechanism before testing the connection again. This can be repeated until an adequate connection is achieved, at which point the ejector unit should be moved from to the second configuration to release the leaflet anchor. This method may include use of a device with any of the other features discussed above with reference to any of the various device aspects, and/or method features as discussed in relation to the second or eighth aspect above, or the other aspects below.

Viewed from a tenth aspect, the invention provides a method of use of the catheter device of the first aspect for repair of the heart by implanting an artificial chordae line, the method comprising: moving the second gripper arm away from the main body of the catheter device; moving the first gripper arm away from the main body of the catheter device; at least one of: rotating the first gripper arm to bring it into contact with the second gripper arm to thereby grasp the leaflet at a point spaced apart from the main body of the catheter device; rotating the first gripper arm to bring it into contact with the second gripper arm to thereby restrain the leaflet before rotating the gripper arm to grasp the leaflet between the first gripper arm and the main body of the catheter device; and pushing the leaflet anchor out of the leaflet anchor tube to pierce the leaflet and form the leaflet anchor into an unfolded configuration so that hooked formations of the leaflet anchor secure the leaflet anchor in the leaflet. This method may include use of a device with any of the other features discussed above with reference to any of the various device aspects, and/or method features as discussed in the method aspects herein.

Viewed from an eleventh aspect the invention provides a method of use of the anchor of the seventh aspect for affixing an artificial chordae line to the heart, the method comprising using an anchor deployment device to implant the anchor into the tissue of the heart. The anchor may be used as a papillary anchor with the method hence including the use of a papillary anchor deployment mechanism. Alternatively, the anchor may be used as a leaflet anchor with the method hence including the use of a leaflet anchor deployment mechanism. This method may include use of a device with any of the other features discussed above with reference to any of the various device aspects, and/or method features as discussed in the method aspects herein. The method may include testing the connection of the anchor to the tissue of the heart, such as via testing as discussed above.

Viewed from a twelfth aspect the invention provides a method of manufacture of the catheter device of the second aspect, the method comprising forming the flexible and optionally extendable joint via cutting of an elastic metal tube. Optionally the same elastic metal tube is also used to form the distal and proximal parts of the two-part body section, which are hence integrally formed with the flexible joint. A nitinol tube may be used and/or the cutting step may use laser cutting. The laser cut tube may be electropolished after cutting in order to remove any sharp edges.

It is considered to offer particular benefits to be able to form the device of the second aspect using the method of the twelfth aspect, although it should be noted that other manufacturing methods may be used as discussed above. The method of the twelfth aspect may include providing the catheter device with any of the features discussed above with reference to the various device aspects.

Viewed from a thirteenth aspect the invention provides a method of manufacture of the ejector unit for the catheter device of the sixth aspect, the method comprising: forming tines into an elastic metal tube via cutting; and deforming the end of the tines with heat setting in order to form a hooked configuration. The ejector unit may be provided with features as discussed above in connection with optional features of the sixth aspect. The manufacturing method may include providing a catheter device as in the sixth aspect and inserting the ejector unit into the catheter device along with a leaflet anchor. A nitinol tube may be used and/or the cutting step may use laser cutting. The laser cut tube may be electropolished after cutting in order to remove any sharp edges.

Viewed from a fourteenth aspect the invention provides a method of manufacture of the catheter device of the first aspect, the method comprising forming a hinge of the first gripper arm integrally with the main body of the catheter device via cutting of an elastic metal tube. The method may optionally include forming the entirety of the first gripper arm, including the hinge, integrally with the main body. It is considered to offer particular benefits to be able to form the device of the first aspect in this way, although it should be noted that other manufacturing methods may be used as discussed above. A nitinol tube may be used and/or the cutting step may use laser cutting. The laser cut tube may be electropolished after cutting in order to remove any sharp edges. The method of the twelfth aspect may include providing the catheter device with any of the features discussed above with reference to the various device aspects. This method may be combined with the method of the twelfth aspect in order to form a single unitary body section with the hinge of the first gripper arm (and optionally also the remainder of the first gripper arm) formed in the same integral section as the two-part housing section with the distal part and proximal part connected by the flexible joint.

Viewed from a fifteenth aspect the invention provides a method of manufacture of the anchor of the seventh aspect, the method comprising: forming tines into an elastic metal tube via cutting; forming openings in the tines; and deforming the tines into hooked forms and heat setting them to form the hooks with openings. The anchor may be provided with features as discussed above in connection with optional features of the seventh aspect. It is considered to offer particular benefits to be able to form the anchor of the seventh aspect in this way, although it should be noted that other manufacturing methods may be used as discussed above. A nitinol tube may be used and/or the cutting step may use laser cutting. The laser cut tube may be electropolished after cutting in order to remove any sharp edges.

In any of the aspects discussed above, the leaflet anchor may be formed from an elastic material and to be arranged so that it assumes an unfolded configuration when no force is applied, and to be able to deform elastically into a folded configuration, for example when constrained within the leaflet anchor tube. The leaflet anchor may be made of a shape memory material, for example a shape memory metal. Nitinol may be used for the leaflet anchor. In some example embodiments the leaflet anchor is made from a laser cut nitinol tube. The anchor may be subject to electropolishing after laser cutting in order to remove undesirably rough or sharp edges. The edges may be chamfered before electropolishing in order to introduce greater curvature, e.g. where sutures or wires may bear against the edges when the anchor is in use.

One exemplary form for the leaflet anchor of any of the above aspects is a grapple hook shape, when it is in the unfolded configuration. The leaflet anchor may hence comprise a straight central shaft with a number of hooks spaced apart radially around the shaft. When in the folded configuration the hooks would be straightened out. The leaflet anchor may conveniently be manufactured by cutting a tube to form sharpened tines at one end, which are then bent into the hooks, with the other end of the tube forming the shaft. The shaft may have a diameter that is relatively small compared to the radial extent of the hooks in the unfolded configuration. For example the shaft may have a diameter of 30% or less of the maximum radial extent of the hooks, for example 20% or less. In one example the shaft is 1-2 mm in diameter and the hooks extend over a diameter of about 5-25 mm. If a shape memory material such as nitinol is used then the tines may be bent and heat set into the grappling hook shape after laser cutting of the nitinol tube.

The leaflet anchor may be provided with one or more sheaths of biocompatible material around the hooks, for example a sheath of ePFTE. This material may be placed around the majority of the hooks leaving the ends of the hooks free so as not to impede piercing of body tissue. A single sheath may be used to provide a covering for two hooks by means of cut outs allowing the sheath to extend across the centre of the anchor and be threaded onto two hooks at two sides of the anchor. Such a sheath might be a tube with an opening, or multiple openings, along one side of the tube where it bridges the centre of the anchor, thus allowing the two hooks to be threaded into the opening(s) at two sides of the centre. A method of manufacture of such a hook with a sheath may comprise inserting the hooks of the anchor into one or more sheaths, e.g. by threading the hook into an ePTFE tube or tubes. An added benefit with this approach is that the artificial chordae line may be threaded around the sheath, locking it in place in the centre of the anchor. This is not possible if the hooks are threaded with individual tubes and/or sheaths, and it allows for easier routine of the line.

Viewed from a sixteenth aspect, the invention provides an anchor for implantation in body tissue to hold a line, the anchor comprising: an elastic material formed to have an unfolded configuration for placement within the body tissue, and a folded configuration for use prior to deployment of the anchor and arranged to permit placement of the anchor into an anchor tube prior to deployment; wherein the anchor is arranged to be elastically deformed into the folded configuration by application of a constraining force, and will return to the unfolded configuration when no constraining force is applied; wherein when the anchor is in the unfolded configuration the anchor has an elongate configuration comprising two anchor pins extending in opposite directions with one either side of a centre of the anchor, whilst when the anchor is in the folded configuration the two pins both extend in the same direction; and wherein ends of the pins are arranged to pierce the body tissue.

It has been found that in some instances some types of body tissue, such as the leaflet(s) of the heart, do not heal as effectively as other types of body tissue, such as the heart wall. Thus, it is beneficial in some instances to provide an anchor designed to result in minimal injury to the body. Such an atraumatic anchor can provide advantages, especially if the form of the anchor allows the body tissue to easily grow around it. The elongate form of the proposed anchor can allow for minimal damage to thin body tissues such as the leaflet, whilst also allowing for close contact with the tissue after implantation so that tissue can grow around the anchor. Close contact and growth of tissue around the anchor means that rotation and translation of the anchor is prevented once it is implanted. When used as a leaflet anchor the ends of the anchor pins can pierce the leaflet during implantation and pass through the leaflet, and when the anchor assumes the unfolded configuration the elongate form will be threaded through the leaflet with outer parts of the two pins on one side of the leaflet, and the centre of the anchor as well as central parts of the two pins on the opposite side of the leaflet. This allows for minimal trauma to the leaflet with a relatively large surface area of the pin placed against the surfaces of the leaflet after implantation. In addition the anchor may have a thin profile, which is more ideal for implantation into a thin body such as a leaflet.

It will be appreciated that the anchor of this aspect may be used as a leaflet anchor or for other forms of tissue, such as for a papillary anchor, although in the examples herein it is used as a leaflet anchor as discussed below. The anchor may be included within an anchor deployment mechanism, which in turn may be a part of a catheter device. In particular, the anchor may be provided within a leaflet anchor deployment mechanism, such as in a catheter device for placement of an artificial chordae line into the heart, including catheter devices of the type discussed above with reference to the various device aspects. Thus, the anchor tube may be the leaflet anchor deployment tube of the devices discussed above.

The unfolded configuration is an elongate configuration comprising two anchor pins extending in opposite directions with one either side of a centre of the anchor, and the elongate form may be a generally straight shape. In the folded configuration the two pins both extend in the same direction and in some examples the folded configuration has a U-shape. The ends of the pins are arranged to pierce the body tissue and thus the ends may be sharp sections, with a pointed shape and/or sharpened edges.

In one example the anchor is formed from an elongate plate with a curve across its width. The elongate plate may for example have a length to width ratio of at least 5:1, for example a length to width ratio of between 5:1 and 15:1. Typically the length of the anchor (in the unfolded configuration) may be 5-10 mm. The curvature across the width is used to increase the stiffness of the anchor and hence to increase the force with which the anchor pushes back toward the unfolded configuration. Once the anchor is folded the curvature becomes flat, which means that further folding needs only a relatively small force. The original curvature impacts on the amount of elastic strain in the anchor material when it is flat, which in turn affects the elastic forces that urge the anchor to return to the unfolded configuration. A typical curvature might be in the range 1-5 mm radius for a thickness of the plate in the range 0.05 to 0.5 mm. To obtain a curved plate the anchor may be formed from a flat plate that is deformed and heat set. Alternatively a curved plate could be provided as a section cut from a tube of the required curvature. The latter approach can involve fewer manufacturing steps since pre-existing tubular sections can be used to provide the required curvature.

In an alternative example, the anchor is formed from a tubular body with a weakened section at the centre of its length to allow for elastic bending of the tube. In this case the ends of the pins may be provided by diagonal cuts across the tube, leaving sharp tips similar to those on hollow needles. The weakened section at the centre of the tube length can be provided by cutting one or more openings into the tube. With this example the ratio of the length to the diameter of the tubular body might be at least 5:1, for example a length to width ratio of between 5:1 and 15:1. Typically the length of the anchor (in the unfolded configuration) may be 5-10 mm. The thickness of walls of the tube may be 0.05-0.5 mm.

The anchor may be formed of an elastic metal, for example a shape memory metal such as Nitinol.

The anchor may include cut-outs or edges with shapes used to change the bending properties and/or to enhance tissue growth and/or prevent horizontal movement once placed. For example, slits, holes, barbs, recesses or ridges may be used. There may be features present to prevent side-ways or rotational movement of the anchor after it has been implanted. Thus, ridges or other features as listed above might be provided along the length of the anchor pins in order to inhibit sideways movement of the pins when in contact with body tissue. There may be openings in the pins with features as discussed above in connection with the openings in the hooks of the anchors of the sixth aspect. Such openings may be formed as discussed above in relation to the method of manufacturing the anchors of the seventh aspect.

The anchor may have a coating or covering for promoting growth in the body tissue, and in particular for improved ingrowth in heart tissue. The coating or covering may cover the main part of the anchor but leave the ends of the pins exposed. One example material for such a coating or covering is ePTFE. Another possibility is Dacron. Other biocompatible materials may be used. The anchor may be covered in a sheath of biocompatible material, such as an ePTFE sheath, this could be assembled by threading the anchor through a tube of material with the anchor in the unfolded configuration. A fabric or woven material may be used. ePTFE has excellent ingrowth in heart tissue, and is well proven in cardiac surgery. An anchor covered with ePTFE is likely to grow into the leaflet further increasing the holding strength and in addition reducing the chance of embolization.

Where a sheath of material is used this may be sutured to the anchor, for example by threading suture through holes in the sheath and the anchor. This may help to prevent the cover to be inverted or pulled into a "lump", as well as reducing chance of embolization if the anchor fractures, since the sheath and suturing will hold parts of a broken anchor together.

There may be an artificial chordae line attached to the anchor. The line may be glued, knotted or threaded multiple times through the anchor to be attached, the line may also be attached in two locations with a loop or similar to distribute forces, and prevent horizontal movement if pulled at an angle. One or more injection moulded part(s) may be used to reduce wear between the line and the metal parts of the anchor in the attachment point(s) of the artificial chordae line. The benefit of using two attachment points with injection moulded protection around the line entry point is that the line entry points may prevents horizontal movement of the anchor once placed.

As noted above, the anchor may be included within an anchor deployment mechanism, which in turn may be a part of a catheter device. In one example, this is a catheter device for implanting an anchor during a procedure for implanting an artificial chordae line into the heart, the catheter device comprising: the anchor, an anchor deployment mechanism for deploying the anchor, and an ejector unit for releasably grasping the anchor. The ejector unit may releasably attach to the anchor at the centre of the anchor. In some examples the anchor deployment mechanism allows for retraction and repositioning of the anchor after deployment of the anchor into the body tissue via the ejector unit, wherein the ejector unit has a grasping device with a first configuration arranged to permit deployment of the anchor into the body tissue without disengagement of the anchor from the ejector unit, and a second configuration in which the anchor is reversibly released from the ejector unit; wherein in the first configuration the grasping device of the ejector unit grasps the centre of the anchor, whilst the pins of the anchor are unimpeded by the grasping device to enable it to be implanted in the body tissue; and wherein in the second configuration the grasping device of the ejector unit is disengaged from the anchor.

It will be appreciated that the ejector unit of this example can take a form similar to the ejector unit described above in relation to the fourth aspect. Thus, the structure and function of the ejector unit may be as discussed above, and the ejector unit as well as the deployment mechanism may interact as discussed above. The deployment mechanism may include an anchor tube as with the leaflet anchor tube described above. The anchor may be a leaflet anchor.

The anchor may be provided with tabs or recesses either side of the width of the anchor at its centre in order to allow for the grasping device of the ejector unit to better engage with the anchor, for example via corresponding hooks or openings to engage with tabs or hooks to engage with recesses.

Viewed from a seventeenth aspect, the invention provides a method for manufacture of an anchor according to the sixteenth aspect, the method comprising: forming the anchor from an elastic material, with the anchor in the unfolded configuration. The method may include forming the anchor as a curved plate or from a tubular body as discussed above. When the anchor is formed from a curved plate then the method may comprise cutting the curved plate out from a tube of the same radius as the required curve. This is has been found to provide a straightforward way to manufacture the required curved profile for the anchor. Alternatively, the anchor may be cut from a flat sheet and then heat set to a curved shape. The method may include providing a sheath of biocompatible material around the elastic material of the anchor, for example a sheath of ePFTE. The method may comprise inserting the pins of the anchor into a sheath, e.g. threading the anchor into an ePTFE tube. This may be done by passing one end of a first pin through the sheath and drawing the elongate form of the anchor through the sheath. The sheath may enclose the centre of the anchor and the majority or entirety of the two pins, leaving the ends of the pins exposed. Alternatively, the sheath may enclose the majority of the two pins, with the ends of the pins exposed and with an opening at the centre to allow for bending of the anchor with lesser restriction from the sheath. This shape of sheath is similar to that discussed above for a grapple hook shaped anchor.

Viewed from an eighteenth aspect, the invention provides a method of use of the anchor of the sixteenth aspect for affixing an artificial chordae line to the heart, the method comprising using an anchor deployment device to implant the anchor into the tissue of the heart. The anchor may be used as a papillary anchor with the method hence including the use of a papillary anchor deployment mechanism. Alternatively, the anchor may be used as a leaflet anchor with the method hence including the use of a leaflet anchor deployment mechanism. This method may include use of a device with any of the other features discussed above with reference to any of the various device aspects, and/or method features as discussed above in the other method aspects. The method may include testing the connection of the anchor to the tissue of the heart, such as via testing as discussed above.

In relation to any of the aspects discussed above, it is advantageous if the leaflet anchor can be placed into the leaflet from beneath, i.e. from the side where the papillary muscle is located, so that the new artificial chordae line may pull the leaflet downward. However, the most convenient route to access the heart involves the catheter entering from above the leaflet. To facilitate the placement of the leaflet anchor from beneath, the catheter device of any of the above aspects may be arranged so that the open end of a leaflet anchor tube is at a proximal end of the gripper device (the 'upper' end when in the heart in the above defined orientation) and the leaflet anchor can be pushed out of the tube moving from the distal end of the catheter device toward the proximal end. The catheter device may include a U-shaped rod for deployment of the leaflet anchor. This may be a U-shaped piece at the end of a wire that is used to actuate the leaflet anchor. Alternatively it may be a U-shaped rod attached to a separate wire at one end of the U-shape. In either arrangement the free end of the U-shape abuts the end of the leaflet anchor and is arranged to push the anchor toward the proximal end of the catheter device when the wire is pulled. The U-shaped rod should be sufficiently stiff to hold its shape when pulled with force applied to the anchor. A ball may be placed at the free end of the U-shaped rod to allow it to best engage with the leaflet anchor (or with the ejector unit, where present). In this way the leaflet can be pierced from beneath.

When the leaflet anchor tube is in the gripper arm, such as the first gripper arm, then the U-shaped rod may extend into the gripper arm. In this case the U-shaped rod needs to be sufficiently elastic to bend when the gripper arm is opened and closed. The U-shaped rod may have a flexible section, for example a section of narrowed cross-section, for aiding the bending motion. The U-shaped rod may also or alternatively be made of a suitably elastic material, which could be nitinol. Advantageously, the elasticity of the U-shaped rod may act as a spring to return the gripper arm to the closed position.

Alternatively the U-rod wire may be made so that no bending is necessary while the gripper opens, if the end of the U-rod is small enough to not touch the walls of the leaflet anchor tube while the gripper rotates, it does not have to bend while the gripper opens. This advantageously allows for a greater operation angle not limited by a requirement for allowing for the U-rod to deflect.

The catheter device of any of the above aspects may include an artificial chordae line attached to the leaflet anchor. A hole or eye may be provided in the leaflet anchor for attachment of the artificial chordae line. In some example embodiments the chord is joined in the catheter device to a wire that enables it to be pulled or pushed. The use of such a wire allows for shortening and lengthening adjustments to the chord. The artificial chordae line may be a Gore-Tex® suture or other appropriate biocompatible material, such as a thin nitinol wire, an ultra-high-molecular-weight polyethylene (UHMWPE) wire, or a composite wire comprising a tough core such as nitinol or high strength suture and an outer coating such as PTFE or ePTFE. The artificial chordae line may comprise an ePTFE suture tube, which may be threaded with a Dyneema core. This Dyneema core may be the same suture that is threaded through the leaflet anchor as mentioned above. The ePTFE-Dyneema tube construction of the artificial chorda line may in addition be coupled to a wire (preferably nitinol) in the opposite end of the leaflet anchor, for example by threading the nitinol wire into the ePTFE tube together with the Dyneema core. The ePTFE tube and the Dyneema wire can then be attached by crimping, gluing or similar methods onto the nitinol wire to allow adjustment of the new artificial chordae line with minimal friction. Such adjustment may be done through an adjustment catheter. In some example embodiments the catheter device also holds a papillary anchor for attachment to the papillary muscle. The artificial chordae line may extend from the leaflet anchor to the papillary anchor. In some embodiments the artificial chordae line joins the two anchors together directly, with no intervening clip as in WO 2008/101113. This means that the artificial chordae line can more closely emulate the natural chords, and so the repair to the heart is more effective.

The adjustment catheter may have stainless steel wire within in its walls, to allow it to exert a pulling force strong enough to retract the papillary anchor. The adjustment catheter may further have one or more small lumens in the wall that allows for actuation of the adjustment and cutting mechanism. Stainless steel tipping may be attached in one or both end of the shaft, and this can be mechanically bonded by for example welding, knots, glue or material reflow to the shaft itself and the stainless steel wires inside the walls of the shaft, alternatively the stainless steel wires in the wall of the shaft may be looped around a feature in the stainless steel tipping (which may be connected to or may form a part of the adjustment housing such as the piston housing of an anchor holder of the type discussed above). The stainless steel tipping may be laser welded to the papillary anchor cutting and adjustment mechanism.

With any of the above aspects the papillary anchor may be formed from an elastic material and may be arranged so that it assumes an unfolded position when no force is applied, and to be able to deform elastically into a folded position, for example when constrained within a papillary anchor housing of the catheter device. The device may be arranged so that the papillary anchor can be pushed out of the papillary anchor housing in order to pierce the papillary muscle with the hooks and to securely engage the anchor with the muscle as the hooks curl into the unfolded position. The papillary anchor may be made of a shape memory material, for example a shape memory metal. Nitinol is a preferred material for the papillary anchor. In one preferred embodiment the papillary anchor is made from a laser cut nitinol tube.

The papillary anchor may include a number of hooks for piercing and engaging with the tissue of the papillary muscle. A grappling hook shape is possible, similar to the leaflet anchor, but the preferred design for the papillary anchor uses a slightly wider tube section relative to the extent of the hooks. Thus in some example embodiments the papillary anchor includes a tube section with a number of hooks extending from one end of the tube, wherein the hooks extend across a diameter that is less than three times the diameter of the tube, for example about twice the diameter of the tube.

Similarly to the leaflet anchor, the papillary anchor may conveniently be manufactured by cutting a tube to form sharpened tines at one end, which are then bent into the hooks, with the other end of the tube forming the body of the anchor. If a shape memory material such as nitinol is used then the tines may be bent and heat set into the hook shape after laser cutting of the nitinol tube. The anchor may be subject to electropolishing after laser cutting in order to remove undesirably rough or sharp edges.

In any of the above aspects and optional features the papillary anchor, where present, may be provided with a mechanism for releasably clamping the artificial chordae line. In one example, the papillary anchor is provided with a locking mechanism that clamps the chord when no force is applied, and that can be elastically deformed to release the chord for adjustment of the length of the chord during implantation thereof. This means that after the leaflet anchor and the papillary anchor are implanted then the new chord can be tensioned appropriately, whilst monitoring heart function, to ensure that the repair is effective, and then the chord can be clamped by releasing the force on the anchor.

After implantation, since the locking mechanism clamps the chord when no force is applied, then the chord will be held between the leaflet and the papillary muscle with the right tension. The papillary anchor may be laser cut before being electropolished. The introduction of chamfers to the edges of the anchor may reduce friction of the chordae line bearing against its edges during adjustment of its length.

The locking mechanism may comprise a resiliently deformable locking segment formed in a wall of the anchor and divided from the wall by one or more slit(s). The anchor may be arranged so that when no forced is applied then the slits are closed with no gap or a relatively narrow gap in order to clamp the line, whereas when a suitable force is applied to the locking segment and/or wall then the locking segment and/or the wall will elastically deform to widen the opening provided by the slit(s) so that the line is released. The anchor may have a tubular body section, in which case the locking segment may be formed in the wall of the tube. The locking segment may be a band with parallel slits on two sides, such that the band can be pulled out of plane with the wall by application of a force in order to open up the slits.

Such a locking segment can be held open by sliding a holder into the slit(s). The anchor may be used in a system comprising an anchor housing for holding the anchor in the unfolded position prior to implantation, a holder for holding the locking mechanism open, a line, and the anchor attached to the line. The holder may comprise a Z-shaped fork with prongs for insertion into the slit(s). The use of a Z-shaped fork can allow for the path of the suture within the anchor housing to have a suitable curve.

The use of electropolishing to mitigate the risk of fraying and/or cutting, and to provide an anchor able to clamp firmly without cutting is considered important. For the papillary anchor, friction over the edges of the anchor experienced by an artificial chordae line having its length adjusted may be reduced due to laser cutting chamfering the edges before electropolishing. Thus, for methods comprising laser cutting a tube, and for devices including a laser cut tube element such as a laser cut anchor, then electropolishing is advantageously used after the laser cutting.

Certain example embodiments of the invention will now be described by way of example only and with reference to the accompanying drawings in which:

FIGS. 2 to 6 show the action of a mechanical gripping mechanism using two gripper arms;

FIGS. 16 and 17 show an example of a hook for an anchor which is threaded with a suture;

FIGS. 18 and 19 show the folded and unfolded configuration of an example of a papillary anchor;

FIG. 20 is a cross-section through a lower (distal) part of the main body of the catheter device showing how the main parts fit inside a papillary anchor deployment mechanism;

FIG. 21 shows an example arrangement for the routing of the artificial chordae line and other lines within the papillary anchor deployment mechanism of FIG. 20;

FIG. 22 is a cross-section of an example with the papillary anchor deployment mechanism of FIG. 20 and a gripping mechanism as in FIGS. 2 to 6, including one possible routing of the artificial chordae line between the papillary anchor and the first gripper arm;

FIG. 49A shows an anchor having tips that extend outward in a folded position, while FIG. 49B shows an anchor having tips that extend inward in a folded position;

FIG. 50A shows the anchor of FIG. 49A in an unfolded position, while

FIG. 52A shows the two-arm gripper device, with the two gripper arms in an open configuration, while

Figure 1:
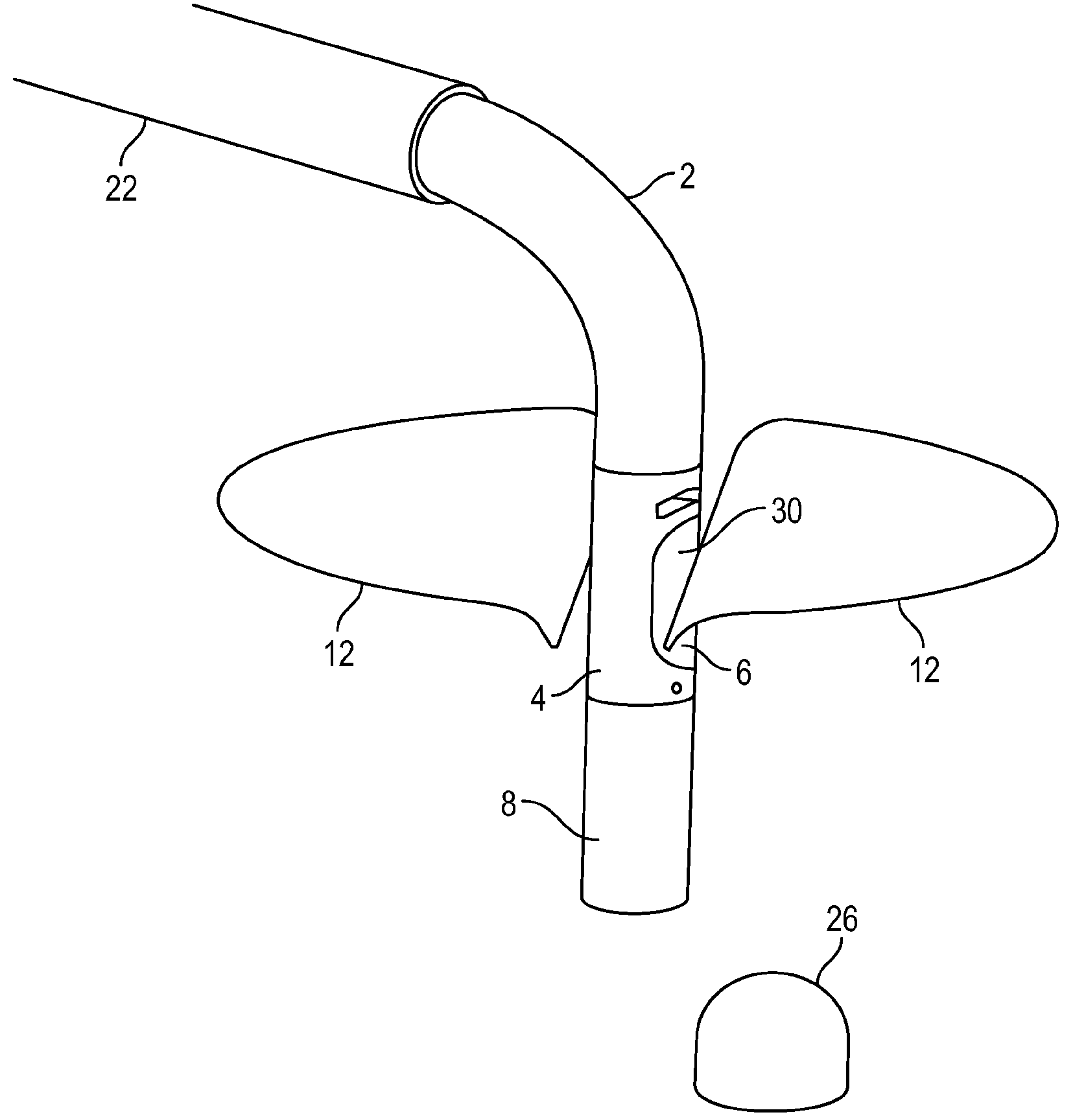
FIG. 1 illustrates the procedure for insertion of a catheter device through a mitral valve.

The catheter devices presented here are proposed for non-surgical (endovascular) insertion of mitral chords to address mitral regurgitation caused by prolapse of a leaflet 12 of the valve. The Figures show different forms of catheter device 2 for this purpose, but it will be understood that the general principles are the same for each device in terms of implantation of a leaflet anchor 10 and a papillary anchor 9 in order to insert one or more artificial chordae lines 14 into the heart. The artificial chordae line(s) 14 are fixed to the prolapsing leaflet 12 and to the papillary muscle 26, thereby recreating a normal anatomy. A single catheter device 2 is used to place both a leaflet anchor 10 and a papillary anchor 9. The length of the chord 14 can be adjusted, again using the same catheter device 2, to eliminate the mitral regurgitation. Thus, the new device enables a single minimally invasive endovascular procedure to be used to repair the mitral valve, providing significant advantages compared to earlier systems requiring more invasive procedures and/or multiple operations.

It should be noted that although an endovascular approach is preferred and the device is hence capable of using this approach, the device could of course be used in different procedures, including more invasive procedures. Many of the advantages will remain, and it could be beneficial to use this device in situations where a more invasive procedure is merited. In addition, it is contemplated that, as discussed above, aspects of the design of the papillary anchor 9 could be used for an anchor for other purposes and this disclosure is not intended to be limited in this regard.

The catheter device 2 described in the following can be used to insert mitral chords through the venous system, starting in the femoral vein in the groin. A catheter is advanced to the right atrium. Approach to the left atrium is then gained by a so-called transseptal puncture whereafter a larger guidance catheter is advanced into the left atrium. The catheter device 2 for the heart repair is then introduced through the guiding catheter and into the left atrium.

X-ray and ultrasound guidance is used to position the device and, as explained in more detail below, the mitral leaflet 12 is grabbed and a new artificial chordae line 14 is attached using a self-expandable leaflet anchor 10. The artificial chordae line 14 is then attached to the papillary muscle 26, using a, papillary anchor 9. Advantageously, the catheter device shown in FIGS. 2 to 6, 14 and 20 to 22 can be used to place the papillary anchor 9 whilst the leaflet 12 is still being grasped by the device. The chord length can now be adjusted to eliminate any mitral regurgitation. Excess chord is then cut and all catheters are withdrawn. Echo and Doppler imaging is used to perform the procedure and monitor the result. The successful use of this endovascular technique will drastically reduce the invasiveness, complications and cost of mitral valve repair.

Figure 31:
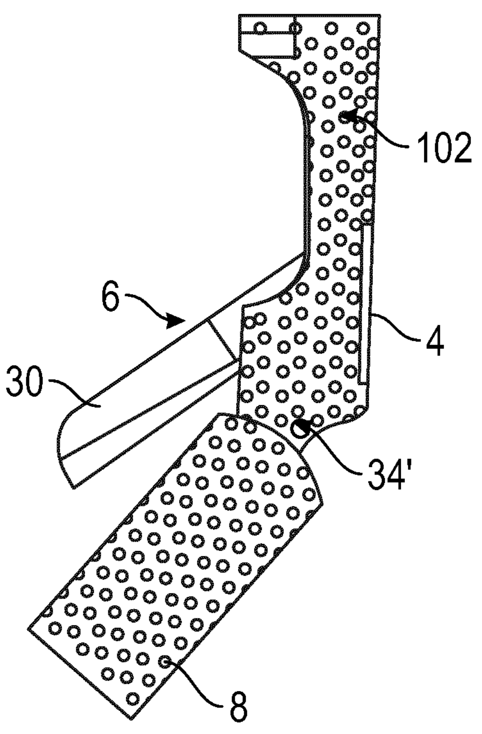
FIG. 31 is a side view of another example of a two-part housing section for the catheter device.
Figure 32:
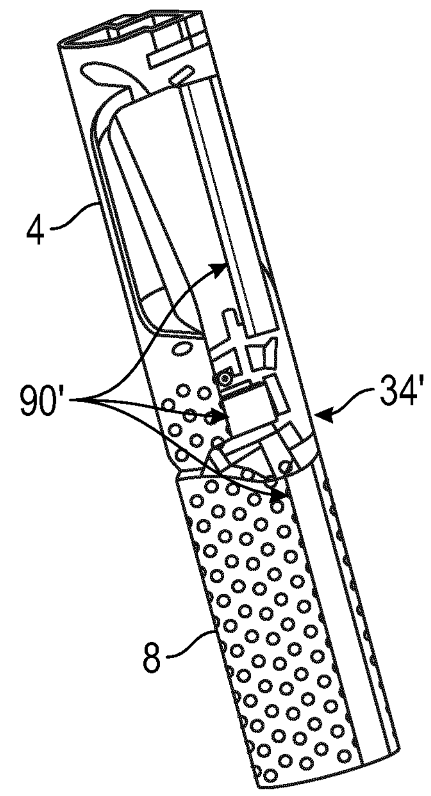
FIG. 32 shows the two-part housing section of FIG. 32 in a different view.

More detail on the structure and function of the device is set out below with reference to the Figures. The procedure of using one form of the device can be summarised as follows:

1) The femoral vein is entered using standard Seldinger technique and the guiding catheter introduced.
2) The guiding catheter is advanced to the right atrium under x-ray guidance.
3) The left atrium is entered after penetration of the atrial septum, guided by x-ray and transesophageal echo.
4) Correct position of the entrance site in the left atrium is verified to assure proper alignment for insertion of the guiding and treatment catheters. The entrance hole in the atrial septum is dilated and the guiding catheter is advanced into the left atrium.
5) A treatment catheter device 2 is advanced through the guiding catheter and positioned in the left atrium above the mitral valve.
6) The prolapsing segment of the mitral leaflet 12 is located with ultrasound and the treatment catheter device 2 is advanced into the left ventricle placing a gripper 6 of the treatment catheter device 2 in position to grip the prolapsing segment. Advantageously, this may use a gripper 6 with two gripping arms 30, 32 as discussed in more detail below with reference to FIGS. 2 to 6.
7) The prolapsing segment is gripped and after assuring correct position the leaflet anchor 10 is pushed through the leaflet 12 allowing it to open and fix the leaflet 12.
8) The connection of the leaflet anchor 10 may be tested whilst it remains attached to the catheter device 2 via an ejector unit 36 as discussed further below with reference to FIGS. 8 to 12, and if the connection is sufficient then the distal end of catheter is advanced further into the left ventricle, advantageously using a flexible and extendable joint 34 as shown in FIGS. 2 to 6 and 14, or using a flexible joint as shown in FIGS. 31 and 32 to angle the joint without extension, until the distal end makes contact with the papillary muscle 26 or surrounding tissue.
9) The papillary anchor 9 is pushed into the papillary muscle 26 area and out of its housing 8 thereby letting the papillary anchor 9 open inside the papillary muscle 26.
10) If the gripper 6 is still grasping the leaflet 12 then it is released, such as by releasing the leaflet anchor 12 from the ejector unit 36 as discussed below with reference to FIGS. 8 to 12.
11) The length of the artificial chordae line 14 is adjusted until mitral regurgitation is eliminated.
12) The catheter device 2 is pulled back from the papillary anchor 9, and elimination of mitral regurgitation is again confirmed by echocardiography.
13) The position of the artificial chordae line 14 is locked at the papillary anchor 9.
14) The excess chordae line 14 is cut.
15) Additional artificial chordae lines may be placed if necessary.
16) The catheter device is fully withdrawn and removed from the vascular system.

FIG. 1 shows guide catheter 22 that has been used to steer a catheter device 2 to a required position within the heart adjacent extending through the mitral valve and hence being between two leaflets 12. The catheter device 2 is composed of four different main parts; a steerable catheter, a gripper housing 4, a gripper device 6 and a papillary anchor housing 8, which holds a papillary anchor 9. Advantageously the gripper housing 4 and the papillary anchor housing 8 may form a proximal part 4 and a distal part 8 of a two part housing section with a central flexible and extendable joint 34 as shown in FIGS. 2 to 6, 14 and 20 to 22. Thus, it should be understood that the procedure shown in FIG. 1 (and likewise in FIGS. 7, 13 and 15) may use this arrangement for the gripper housing (proximal part) 4 and papillary anchor housing (distal part) 8. The steerable catheter could be replaced with an alternative arrangement using a steerable sheath about a steerable catheter and flexible tubing within the steerable catheter.

Figure 2:
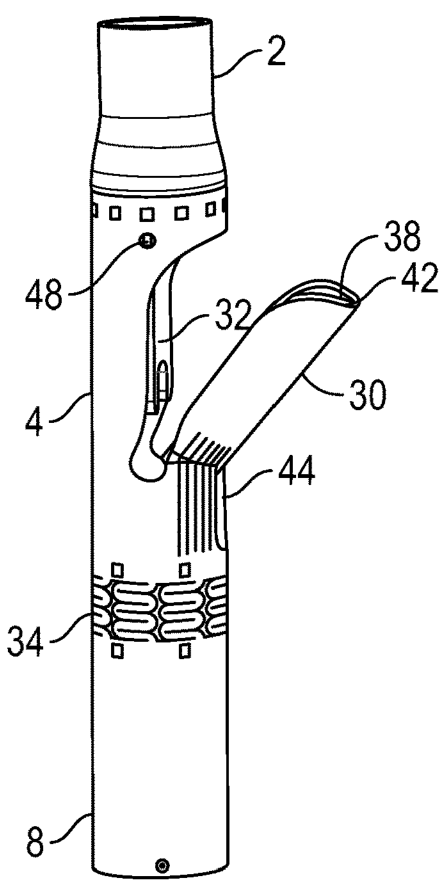
Figure 3:
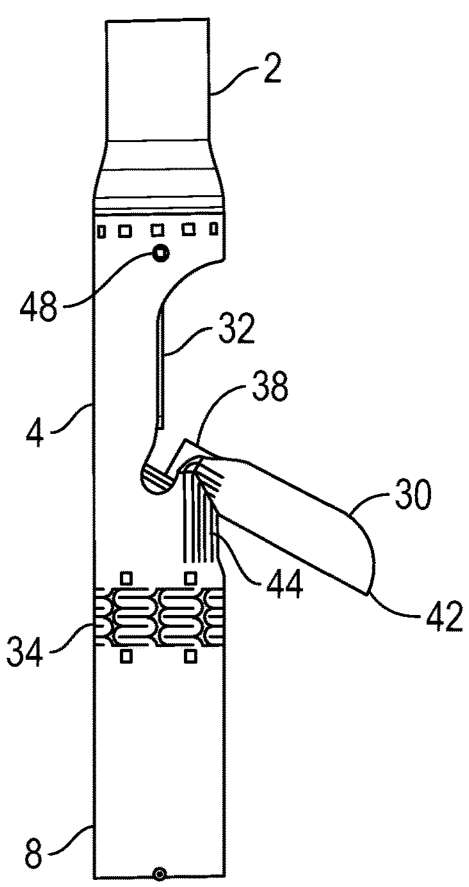
Figure 7:
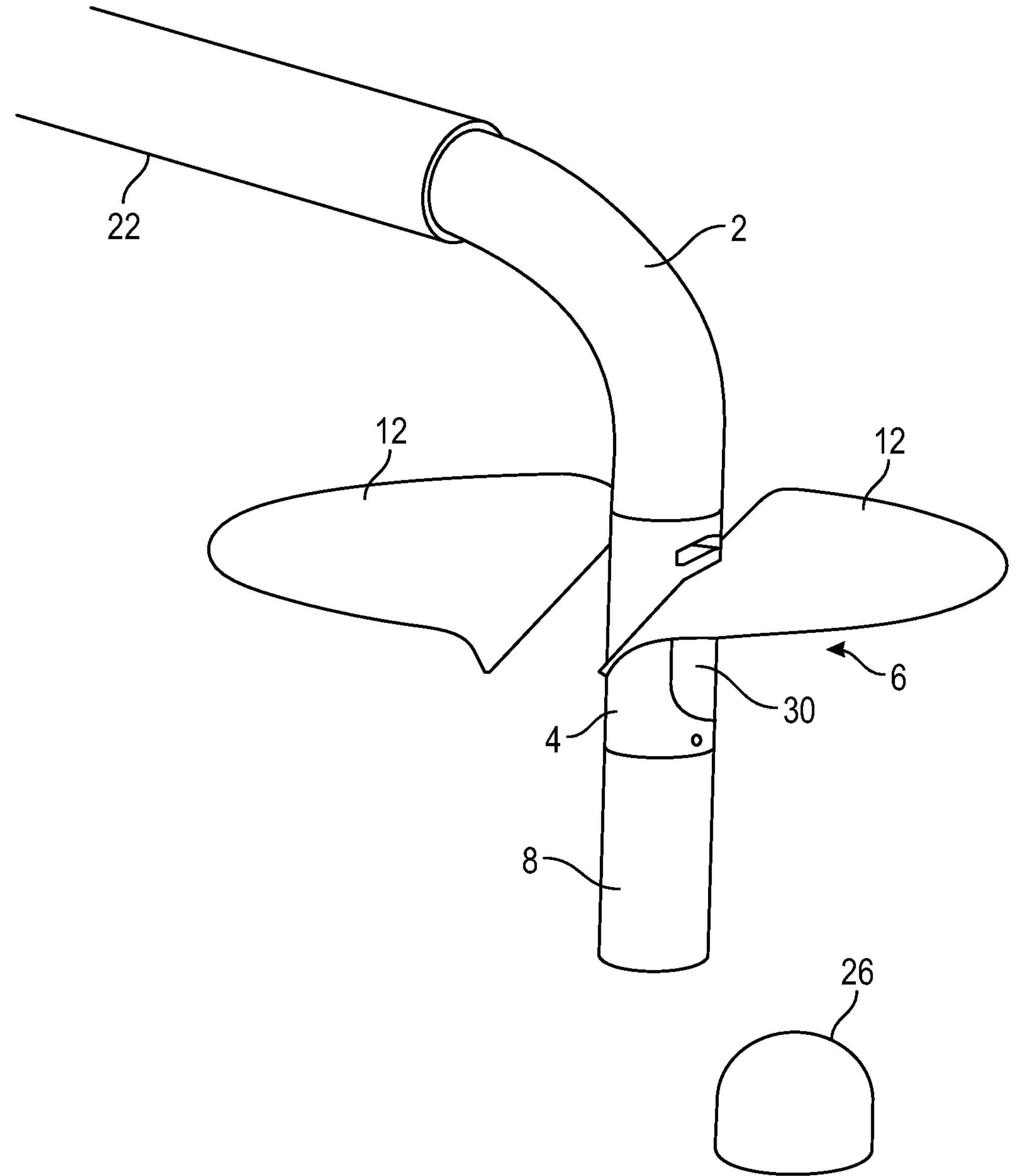
FIG. 7 illustrates gripping of a leaflet of the mitral valve with one gripper arm.

FIG. 1 shows a front view of one example catheter device with the gripper device 6 closed. The gripper device 6 of some arrangements uses a single gripper arm 30 that grips the leaflet 12 against the gripper housing part 4 as shown in FIG. 7. In other arrangements the gripper device 6 uses two gripper arms 30, 32 as shown in FIGS. 2 to 6 in order to allow the leaflet 12 to be grasped between the two gripper arms 30, 32 at a point spaced apart from the main body of the catheter device. The gripper device 6 is a part of a leaflet anchor deployment mechanism for deploying the leaflet anchor 10 to attach it to the leaflet 12 of the heart. The gripper device 6 includes a leaflet anchor tube 38 for housing the leaflet anchor 10 in a folded configuration prior to deployment. In the example embodiments the leaflet anchor tube 38 is in the (first) gripper arm 30, as seen in FIGS. 2 and 4, for example. When the gripper device 6 grasps the leaflet 12, the leaflet anchor 10 can be pushed out of the leaflet anchor tube 38 to pierce the leaflet 12 and form the leaflet anchor 10 into an unfolded configuration so that hooked formations 40 of the leaflet anchor 10 secure it in the leaflet 12.

The leaflet anchor 10 is connected to an artificial chordae line 14, which can sit inside a narrow channel that goes along the surface of the first gripper arm 30 (as shown in FIGS. 8 to 12, for example) and via the papillary anchor housing 8 to the papillary anchor 9 (as shown in FIGS. 20 to 22, for example). The channel can be slightly smaller than the diameter of the new artificial chordae line 14 and/or have a thin shielding structure (not shown). This makes the artificial chordae line 14 sit in place due to a friction fit. The new artificial chordae line 14 goes into the papillary anchor housing 8 and through a papillary anchor locking section, through a locking and cutting piece 18, and through Z shaped fork 20. These parts are described in further detail below with reference to FIGS. 20 to 22. The new artificial chordae line 14 can be attached to a wire which passes back along the catheter all the way to the outside (to make the adjustment smoother). The wire allows for a shortening of the chord during the procedure, by pulling, or a lengthening of the chord, since the wire can be pushed through the catheter.

The two-part housing section, with the gripper housing (proximal part) 4 and papillary anchor housing (distal part) 8 might be approximately 6-7 mm in diameter, and approximately 30 mm in length.

FIGS. 2 to 6 show steps in movement of the gripper mechanism 6 in an example with two gripper arms 30, 32 as discussed above. This gripper mechanism 6 is a part of a housing section that also includes a flexible and extendable joint allowing the papillary anchor housing 8 (distal part) to be moved toward the papillary muscle 26 after the leaflet 12 has been grabbed by the gripper mechanism 6. In this example, in order to grasp the leaflet 12, the first gripper arm 30 is rotated to move its end 42 away from the main body of the catheter device, with this rotation being enabled via a weakened area 44 of the tubular form of the main body. It can be seen that the leaflet anchor tube 38 sits inside the first gripper arm 30, with the end of the leaflet anchor tube 38 having an opening at the end 42 of the first gripper arm 30. With the first gripper arm 30 open, the second gripper arm 32 is free to rotate to move its end 46 outward of the main body. In this example the second gripper arm 32 rotates around a hinge formed by pins 48 placed in holes in the proximal part 4 of the two-part housing section, but it will be appreciated that a similar final placement of its end 46 may be achieved via a sliding movement. With the second gripper arm 32 folded outward the first gripper arm 30 can close so that the two ends 42, 46 come into contact at a point spaced apart from the main body of the device. This allows the leaflet 12 to be grasped. With the leaflet 12 in place the leaflet anchor 10 can be moved out of the leaflet anchor tube 38 to implant it, such as via a mechanism with an ejector unit 36 as described below in relation to FIGS. 8 to 12, with the final positioning of the leaflet anchor 10 being similar to that shown in FIG. 13.

FIG. 7 shows an alternative form of gripper mechanism 6 that grasps the leaflet 12 with a single gripper arm that holds it against the gripper housing 4. This could also use the ejector unit 36 mechanism of FIGS. 8 to 12.

A ridged surface on the gripper arm(s) 30, 32 may be provided to help it grip the leaflet 12. 3D ultrasound and/or other available sources can be used to confirm that the gripper mechanism 6 has grasped the correct part of the leaflet 12.

Figure 13:
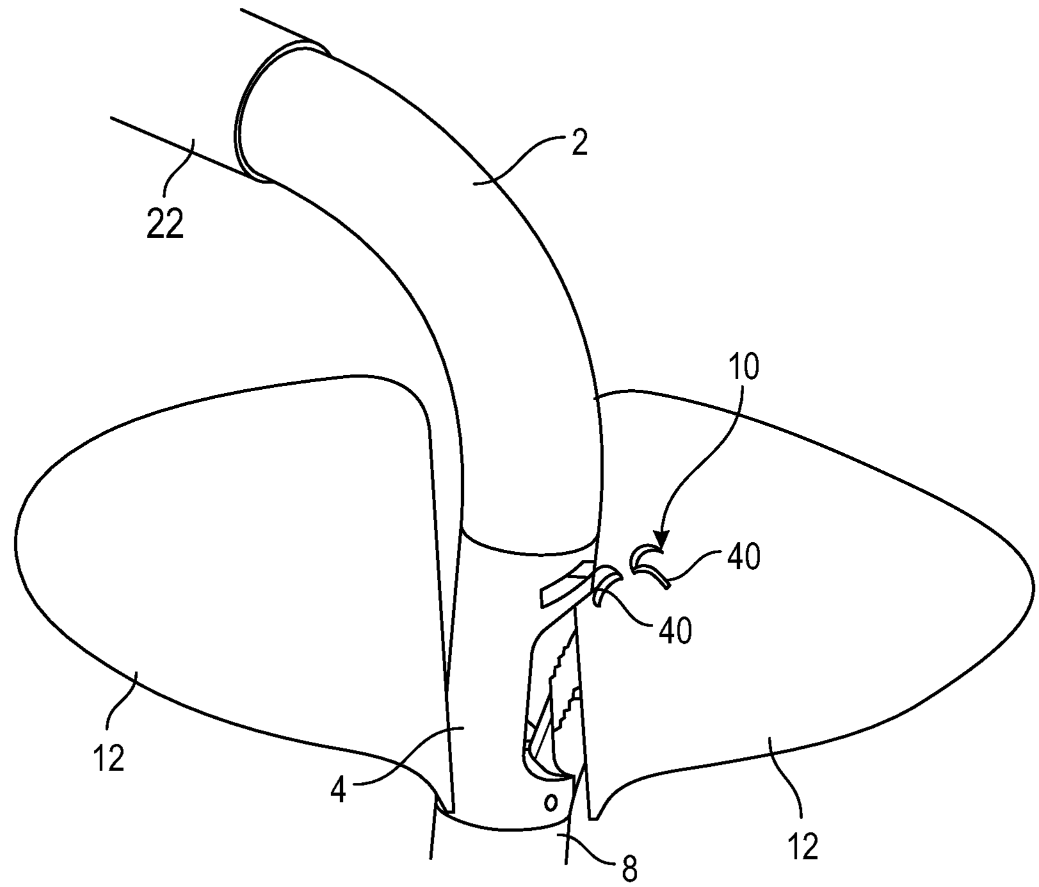
FIG. 13 shows a close up view of the valve during placement of a leaflet anchor, which is coupled to an artificial chordae line.

The gripper mechanism 6 can be opened and closed as many times as needed to grasp the right part of the leaflet 12. The opening and closing may be facilitated by a system allowing for one wire to pull the gripper mechanism 6 open, and one to pull it closed. Different arrangements of wires and/or rods may be used to control the example with two gripper arms 30, 32, as discussed above. Once the position of the gripper mechanism 6 is confirmed then the leaflet anchor 10 can be pushed out of the end of the leaflet anchor tube 38, such as by pulling a wire in the other end of the catheter. FIG. 13 shows a close up view of the leaflet anchor 10 placed in the leaflet 12 with the hooked formations 40 engaging with the leaflet 12.

Figure 8:
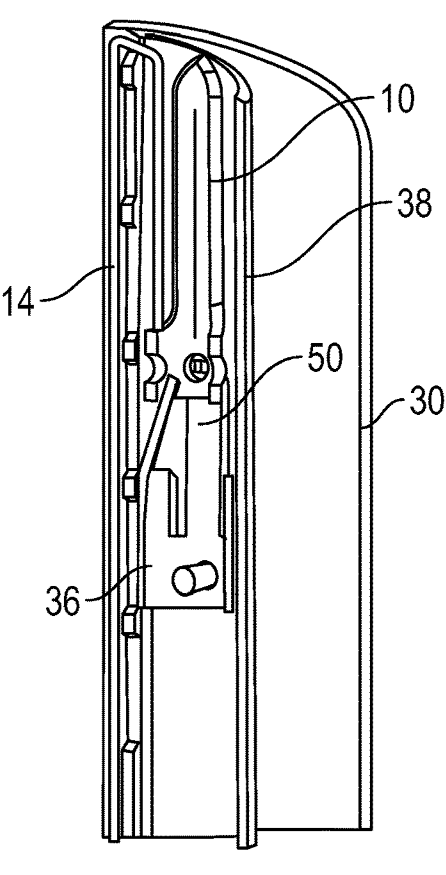
FIGS. 8 to 12 show deployment of a leaflet anchor in a device using an ejector device.
Figure 9:
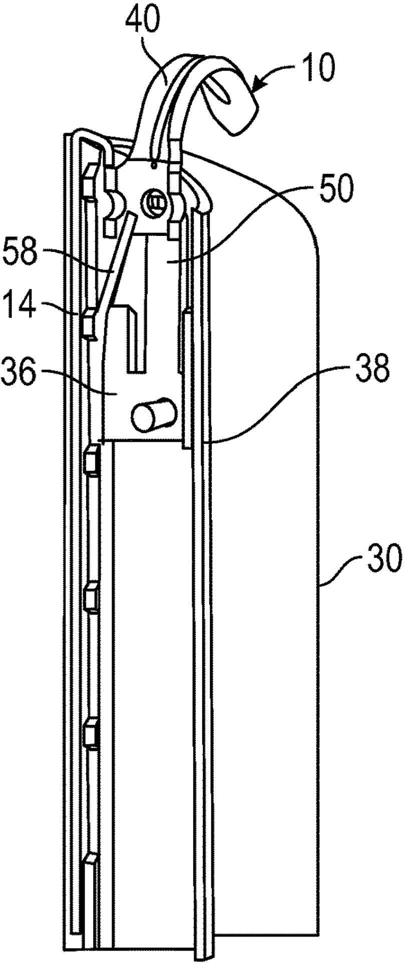
Figures 10, 11, 12:
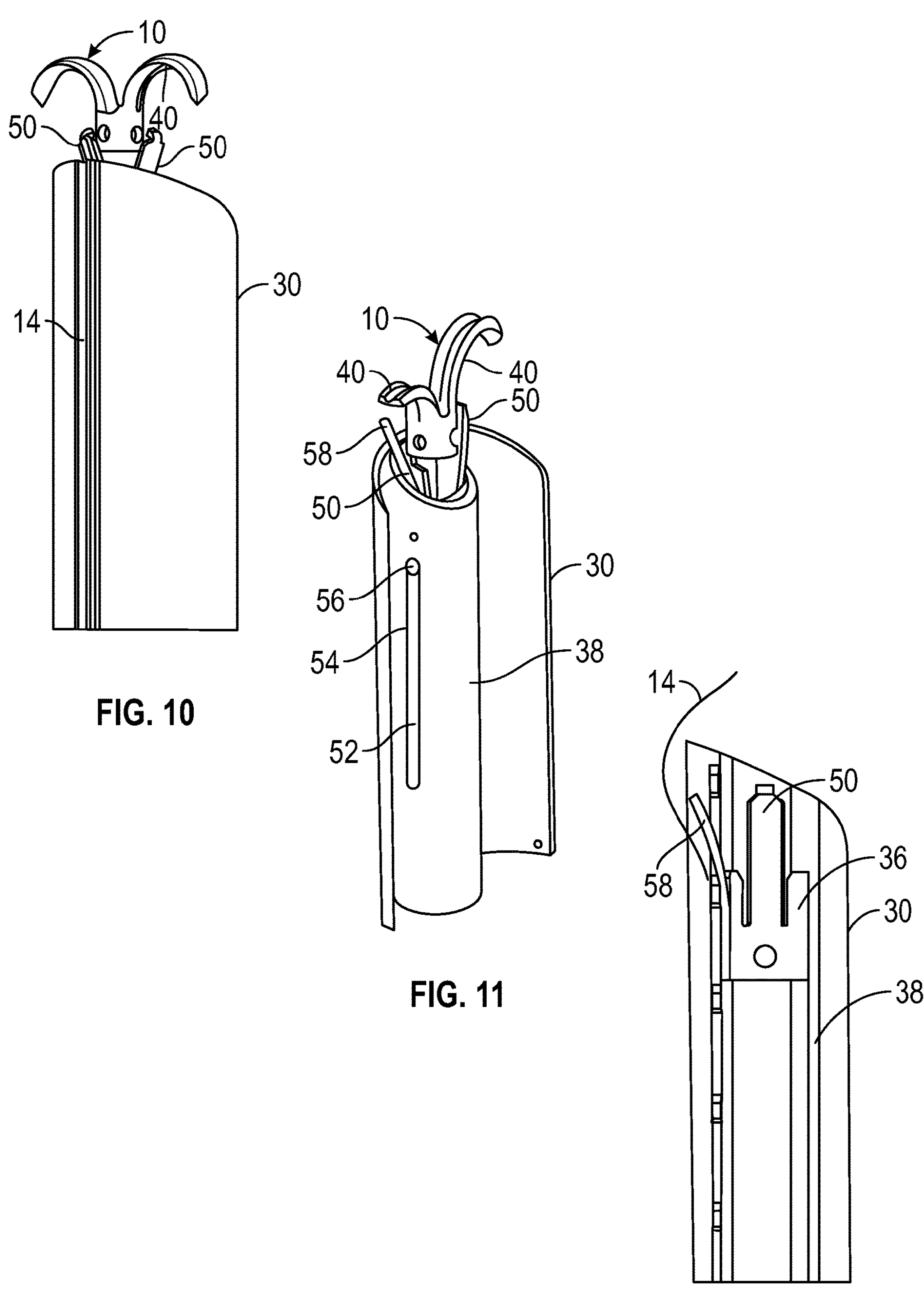

As noted above, an ejector unit 36 may be used as shown in FIGS. 8 to 12. With the use of the ejector unit 36 the leaflet anchor deployment mechanism allows for retraction and repositioning of the leaflet anchor 10 after deployment of the anchor 10 into the leaflet 12. This is achieved via the ejector unit 36, which includes a grasping device 50 with a first configuration, as shown in FIG. 8 and FIG. 9 and a second configuration as shown in FIG. 10 and FIG. 11.

In the first configuration the grasping device arranged to permit deployment of the leaflet anchor 10 into the leaflet 12 without disengagement of the leaflet anchor 10 from the ejector unit 36. Thus, the grasping device 50, which in this example comprises two grappling hooks 50 as shown, grips the leaflet anchor 10 and can advance along the leaflet anchor tube 38 from the fully stowed position as in FIG. 8, to a position in which the anchor 10 is deployed as shown in FIG. 9, without releasing the anchor 10. The grappling hooks 50 are held to the leaflet anchor 10 as they are constrained within the leaflet anchor tube 38. The ejector unit 36 is hence arranged so that it remains in the first configuration whilst the leaflet anchor 10 is being implanted.

With the leaflet anchor 10 implanted the grasping device 50 and ejector unit 36 can be used to test the connection of the leaflet anchor 10 to the leaflet 12, for example by a force being applied to the leaflet anchor from the ejector unit whilst the grasping device 50 is in the first configuration.

The grasping device 50 moves into the second configuration when the constraint from the leaflet anchor tube 38 is no longer present, for example when the grappling hooks 50 move beyond the end of the tube as shown in FIG. 10. Thus, if the connection has been tested and the physician decides to release the leaflet anchor 10 then they can further advance the ejector unit 36, which will move it into the second configuration. In this second configuration the grasping device 50 of the ejector unit 36 is disengaged from the leaflet anchor 10.

If the physician is not satisfied by the connection during the testing (for example, if there is too much movement of the anchor 10 and/or not enough resistance to force on the line) then the leaflet anchor 10 can be retracted and placed in another location. If the grasping device 50 did not change from the first configuration during this test then the latter procedure may be carried out by reversing the deployment of the ejector unit 36 and leaflet anchor 10, for example by drawing those parts back into the leaflet anchor deployment mechanism. If the second configuration was used before it was determined that the connection of the anchor was not adequate then to retract the anchor 10 the ejector unit 36 should be first moved back to the first configuration so that the grasping device 50 reengages with the leaflet anchor 10, and then after that the deployment of the ejector unit 36 and leaflet anchor 12 is reversed, for example by drawing those parts back into the leaflet anchor tube 38.

A groove 52 is provided in a wall of the leaflet anchor tube 38 for guiding the ejector unit 36. The groove 52 ensures that the ejector unit 36 remains a single orientation relative to the tube 38 while it is moved along the tube. The groove 52 can set maximum limits on the range of movement of the ejector unit 36 and thus may prevent it from going too far in either direction, out of or into the leaflet anchor tube 38. The ejector unit 36 has a guide pin 56 for engagement with the groove 52. A narrowing 54 in the groove 52 is provided to act as an indicator to let the operator know when the ejector unit 36 has reached a certain position. The size of the guide pin 56 and the width of the narrowing 54 are set so that engagement of the pin 56 with the narrowing 54 in the groove 52 will require an increased force before further movement can be made, thus providing tactile feedback to the operating physician.

The leaflet anchor deployment mechanism of FIGS. 8 to 12 also includes a line pusher 58 for directing the artificial chordae line 14 out of and away from the leaflet anchor tube 38 during deployment of the anchor 10. The line pusher 58 directs the artificial chordae line away from the leaflet anchor tube 38 so that it can be more readily accessed for later manipulation, such as for tightening the line 14 or for pulling on the implanted leaflet anchor 10 for testing of the connection. The line pusher 58 is actuated during the action of deployment of the leaflet anchor 10, with this actuation being triggered when the leaflet anchor 10 is released from the ejector unit 36. Thus, the line pusher 50 is released when the ejector unit 36 withdraws away from the implanted leaflet anchor 10.

In the example shown, the line pusher 58 transitions from a constrained state to a non-constrained state and moves radially outward to push the line 14 out, with this radially outward movement being permitted and the line pusher released once a constraint from the leaflet anchor 10 is removed. The line pusher 58 is an arm that extends axially forward from the ejector unit toward the leaflet anchor 10 and radially outward of the leaflet anchor tube 38 when the arm is at rest with no forces applied. Prior to deployment of the leaflet anchor 10 the arm of the line pusher 58 is bent elastically to place its distal end within the leaflet anchor 10, as shown in FIGS. 8 and 9, so that it is constrained and cannot move to its radially outward position until the leaflet anchor 10 and the ejector unit 36 move apart, as is best shown in FIG. 11. As the ejector unit 36 continues to withdraw into the leaflet anchor tube 38 the line pusher 58 remains in its unconstrained state with the line pusher 58 as well as the line 14 being pushed out of a slit in the leaflet anchor tube 38, as shown in FIG. 12.

Figure 14:
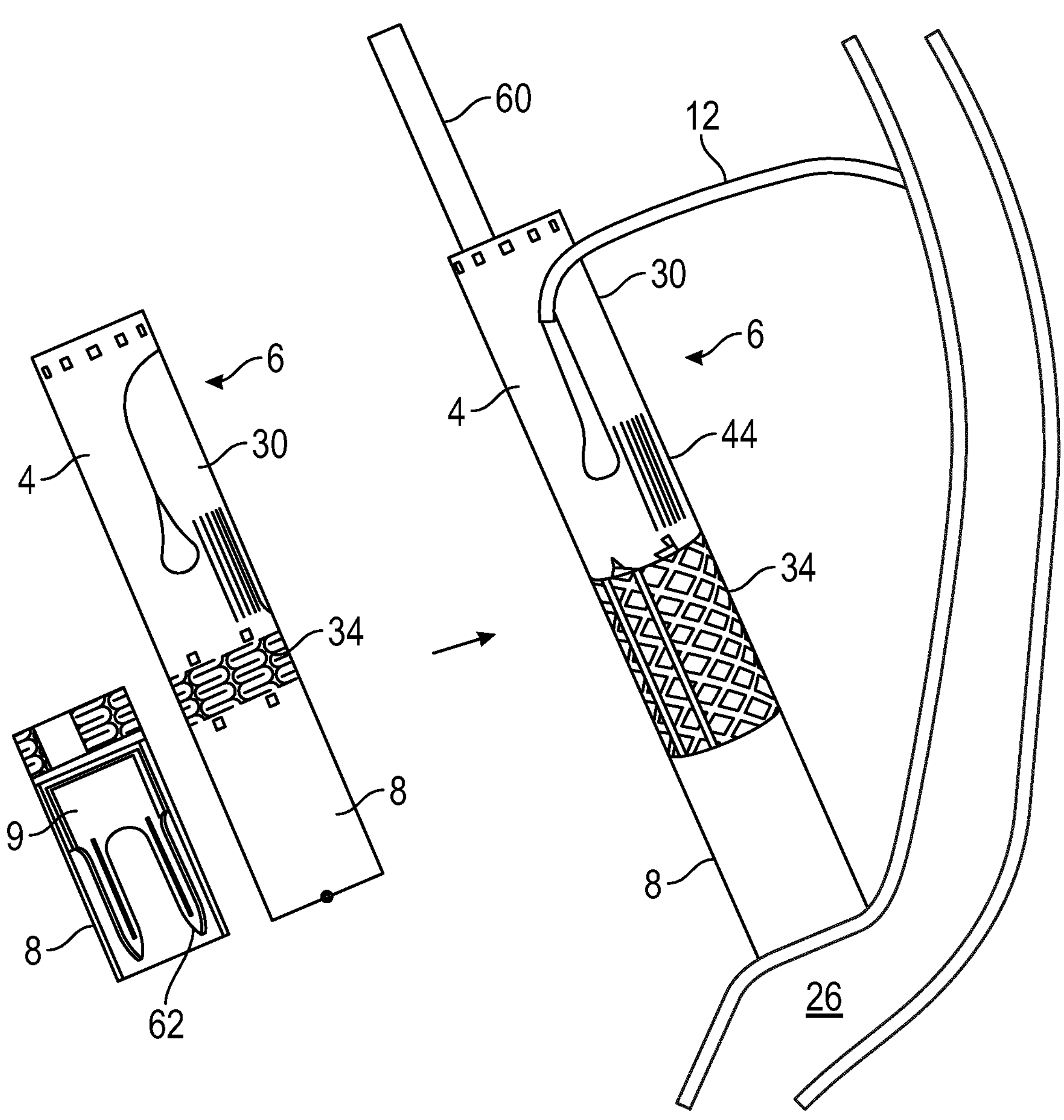
FIG. 14 shows movement of the distal end of the catheter device to the papillary muscle for placement of a papillary anchor.

With the leaflet anchor 10 implanted in the leaflet 12 the papillary anchor housing 8 at the end of the treatment catheter is then placed onto the papillary muscle 26. With the use of a flexible and extendable joint 34 this may be done as shown in FIG. 14. In this example, the flexible and extendable joint 34 is formed by flexible meandering sections cut into a tubular form of the main body. Advantageously the flexible and extendable joint 36 is formed integrally with a tubular distal part 8, which provides the papillary anchor housing 8 and with a tubular proximal part 4, which provides the gripper housing 4. Further advantageously the tubular form of the gripper housing 4 may include an integrally formed gripper arm 30, with a weakened section 44 of the tube providing a hinge. The flexible and extendable joint 34 can be extended by means of wires and/or rods 60 (or via an adjustment catheter 21, that also may push out the papillary anchor 9), which may apply a force to stretch elastic elements of the joint 34. This extension is used to move the papillary anchor 9, within its housing part 8, to place it against the papillary muscle 26, or close to it, since the wires/rods along with the papillary anchor 8 within the distal housing part 8 move with the housing 8 as the joint 34 extends. This can be due to friction between the papillary anchor 9 (or a papillary anchor push tube) and the internal surface of the distal part 8 of the housing section. The position can be confirmed by 3D ultrasound and/or other available sources.

When the distal end of the distal part 8 meets the body tissue, and as further force is applied the counterforce from the body tissue eventually surpasses the forces holding the papillary anchor 9 in place, at this point tissue is pushed flat below the base of the distal part 8 giving a maximal chance of placing all pins 62 of the papillary anchor 9 correctly in tissue, and force can be applied to the papillary anchor 9 so that the ends of the pins 62 then move beyond the distal end of the distal part 8 to meet the body tissue. This may be done via additional force on the papillary anchor 9 from rods or wires 60 or extending the adjustment catheter 21, or advantageously it may be done through a pre-tension on the papillary anchor 9 (or friction between the adjustment catheter 21 and the distal part 8) that is held by friction with the distal part until the forces from the body tissue on the distal part 8 changes the balance of forces with the friction sufficiently so that the papillary anchor 9 ejects in a way similar to a paper stapler. As the papillary anchor 9 is ejected the pins 62 fold out and form into the hook shape of the unconstrained papillary anchor 9 to thereby engage with the body tissue 26. At this point the connection can be pull tested by operator, and/or visually confirmed on x-ray and/or ultrasound. If the connection is not satisfactory, the papillary anchor 9 can be pulled back into the distal part 8 and re-placed to attempt an improved coupling of the anchor 9 with the body tissue 26.

Figure 15:
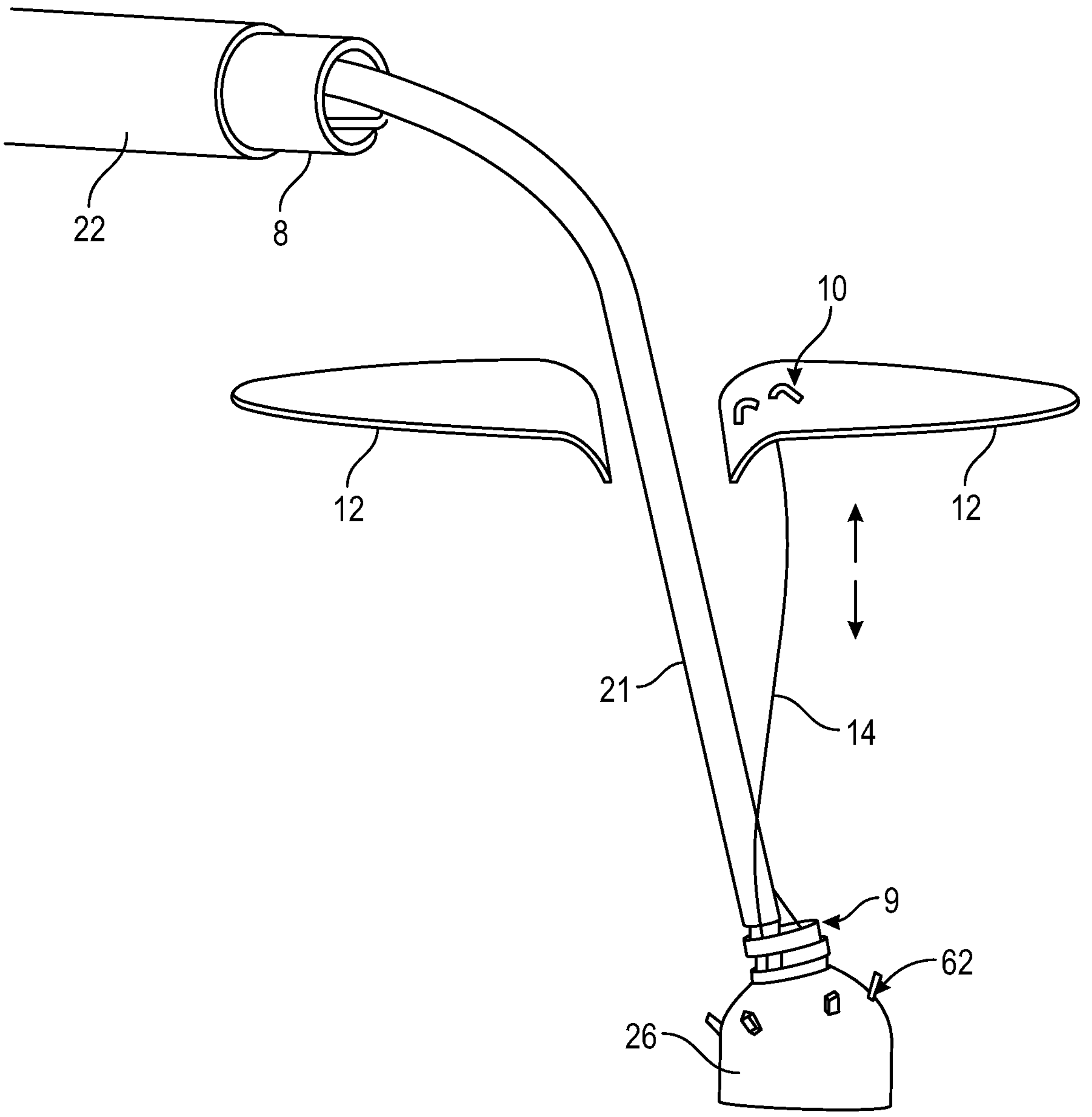
FIG. 15 illustrates withdrawal of a treatment catheter part of the device and adjustment of the chord length with an optional adjustment catheter.

FIG. 15 shows the possible next steps. The main part 4, 8 of the device is retracted to minimize influence on the moving leaflets 12. An adjustment catheter 21, which may comprise a Z-shaped fork 20 at its distal end as shown in FIGS. 20 to 22, can remain at the papillary anchor 9. The length of the artificial chordae line 14 can be adjusted with a wire from the outside. The length is continuously adjusted and the functioning of the leaflet 12 is monitored. The length of the artificial chordae line 14 can be reduced by pulling the chord wire back through the catheter. The length can also be increased by pushing the chord wire, which will slacken the artificial chordae line 14 and allow the movement of the leaflet 12 to pull it out of the adjustment catheter 21. The small size of the adjustment catheter 21 means that the effect of the device on the functioning of the leaflet 12 is minimised. The right length for the artificial chordae line 14 is confirmed with 3D ultrasound and/or other available sources.

When the correct length is confirmed then the device is disengaged from the papillary anchor 9. This process also locks the artificial chordae line 14 in place and cuts off any excess, which is retained in the catheter and withdrawn from the body when the catheter is removed. FIGS. 20 to 22 include more detail of the Z-shaped fork 20 and the cutting piece 18, as discussed below. The Z-shaped fork is used to hold open a locking segment 28 of the papillary anchor 9. The locking segment 28 is a band of the papillary anchor 9 that can be flexed to open a gap for the artificial chordae line 14 to pass through. In the natural shape of the papillary anchor 9, when no forced is applied, this locking segment 28 fits closely with the remainder of the anchor 9 and so it will hold the artificial chordae line 14 in place. The Z-shaped fork 20 is used to hold the locking segment 28 open until the artificial chordae line 14 is the correct length. The cutting piece 18 cuts the artificial chordae line 14, which is pulled against the blade when the adjustment process is completed.

FIGS. 16 to 19 include more details of the papillary anchor 9, including its hooks 62 which are formed by curving pins 62. FIGS. 16 and 17 show one possible form for the hooks 62, with a central slit 64 and a series of holes 66 threaded with a suture 68. As discussed above, this suture 68 and the holes 66 can allow the hooks 62 to better engage with body tissue during healing, as well as keeping the material of the hooks 62 connected to the main body of the papillary anchor 9 in the event of a breakage. FIG. 16 shows the folded/constrained shape of the hook 62, which is also the shape of a tine formed in a tubular section during manufacture of the anchor 9, prior to heat setting to form the curve. FIG. 17 shows the curved form of the hook 62, i.e. the unfolded/unconstrained form.

FIGS. 18 and 19 show an example of an entire papillary anchor 9, again illustrating the folded (FIG. 18) and unfolded (FIG. 19) configurations. This papillary anchor 9 includes hooks 62 with an opening in the form of a slit 64, which gives various advantages as discussed above, including better engagement with the body during healing as well as increased surface area without loss of flexibility.

The device can include a safety wire 72 that acts to prevent the papillary anchor 9 from escaping into the body in the event that it is not correctly placed. Once the locking and cutting have been done, and the papillary anchor 9 is seen to be secured to the papillary muscle 26 and to the leaflet anchor 10 then the safety wire 72 is cut.

In order to deploy the leaflet anchor then a U-rod can be used. This U-rod 30 would be housed within the gripper arm 30 and partly within the main part of the catheter, with a free end of the U-shape being used to push the leaflet anchor 10 (and ejector unit 36, where present) along the leaflet anchor tube 38. The U-rod has a bendable section so the gripper can open and close, while the U-rod is inside. Advantageously, this bendable section can act as a sort of a spring, applying a restoring force to return the gripper arm 30 to the closed position. The U-rod is made of a material with the ability to deform elastically to a high degree in order to allow for the bending of the bendable section. Suitable materials include shape memory materials, for example shape memory metals such as nitinol. A shape memory metal also has the advantage that the U-rod can be made stiff, which makes the transfer of force with the U-rod more efficient. The U-rod may consist of a thin nitinol wire and tubes on the outside of the wire, to make the U section stiffer. Alternatively, the U-rod could be made of several types of materials to achieve the required properties.

As noted above, imaging techniques such as 3-D ultrasound or fluoroscopy can be used when guiding the device and to confirm the correct location of the leaflet 12 within the gripper device 6. To assist in this, the echogenic properties of the device may be improved by abrasive blasting, mechanical texture or a special coating, for example an echogenic polymer coating. The gripper device 6 can also be provided with a detection system to confirm the location of the leaflet 12 within the gripper 6. In a modified gripper (not shown) a fluid based sensor system is provided. This uses holes on the gripping surface of the gripper housing 4. The holes are connected through tubes to a fluid supply, such as contrast fluid from a syringe. When the gripper pinches the leaflet (or other tissue), the holes will be blocked by tissue preventing the flow of fluid. This can be used to determine if the leaflet is in the correct position to deploy the leaflet anchor. The device could be built with various numbers of holes, for example three or four, with the combination of open and closed holes being used to determine the position of the leaflet/tissue within the gripper 4. If four valves are placed in a square pattern, two closed and two open valves could represent the correct position of the leaflet. In one example, the sensor system consists of one-four fluid channels that can be located in the instrument wall, opposite of the gripper arm, alternatively in the gripper arm tip. The channels are connected to ports on the instruments handle where they can be injected with a contrast fluid, which can be visible on either echocardiography or fluoroscopy. An absence (or reduction) of visible fluid and/or the increased resistance to inject fluid in both channels tells the operator that the leaflet is correctly placed prior to leaflet anchor deployment.

In another example a pump with a monitoring circuit constantly pumps a small amount of water through the tubes of the sensor. The detection circuit can detect pressure rise or change in the volume going through each tube, the rise in pressure can indicate which tubes that are obstructed and to some degree says something about how thick the tissue in the leaflet actually is (thinner tissue tend to cause less pressure rise, relative to thicker tissue). The monitor device can for example be equipped with simple LEDs that go green if leaflet is properly gripped. This will give physicians further confirmation (in addition to Ultrasound) that they have captured the leaflet correctly, which ultimately results in higher procedure success rates. In a slightly different embodiment the pump can be programmed to slowly pump fluid in and out of the tubes, which does not require additional fluid if the procedure takes long time.

The device may include a suture/line management system, to prevent tangling. Sutures may be held inside slits or tubes, until everything is ready for them to be released, this will reduce the chance of entanglement. The suture slit in the papillary housing 8 may be equipped with a one way "suture valve" cut from the nitinol tube itself, it will prevent native chordaes from entering the chordae channel.

The artificial chordae line 14 can be attached to the anchor(s) in several ways. For example, wire through holes with knots, welds or glue. The artificial chordae line 14 can be made of Gore-Tex® suture material, or a thin nitinol wire. This preferred embodiment uses Gore-Tex® since it is easier to cut once the length has been adjusted. The artificial chordae line 14 has a diameter of approximately 0.1-0.6 mm. The leaflet anchor 10 is approximately 1-2 mm in diameter, and approximately 4-6 mm in length (when straight).

The leaflet anchor pins can be cut with several different profiles to achieve different strength, and/or faster healing. Since the leaflet anchor 10 is cut from tubing using laser cutting then different shapes are easy to produce. The pins of the anchor may for example have a straight edge (minimum friction) or a profile for increased friction, such as a smooth or sharp saw tooth, or a barbed profile. The anchor shape can vary based on the requirements of the procedure. Different anchor designs could be available for a surgeon to select based on their assessment of the patient.

As with the leaflet anchor pins, the papillary anchor pins can be cut with several different shapes to achieve different pull out strength and/or faster healing. The pins of the anchor may for example have a straight edge (minimum friction) or a profile for increased friction, such as a smooth or sharp saw tooth, or a barbed profile. The anchor shape can vary based on the requirements of the procedure. Different anchor designs could be available for a surgeon to select based on their assessment of the patient.

FIGS. 20 to 22 illustrate interaction of the papillary anchor 9 with the chord and a cutting piece 18 of the catheter device. The cutting piece 18, is made of a suitable biocompatible material, preferably cut with laser and sharpened by grinding away some material. The material may for example be stainless steel, titanium or titanium alloy. Nitinol could also be used. The Z-shaped fork 20 is used to hold the locking segment 28 open to make room for the chord between the locking rings and locking segment 28 in the papillary anchor 9.

Once the papillary anchor 9 is placed and the delivery device is retracted, as discussed above, then a chordae-wire 14 is used to adjust the chordae length. An optional wire lock (not shown) can be pulled to gently pinch the artificial chordae line 14 in the temporary adjusted state during analysing of the length, the wire-chordae will in addition be held from the outside. Once the correct length is achieved, a locking wire 70 is pulled, which bends/retracts the Nitinol Z shape 20 and locks the chordae in place by releasing the locking segment 28. Then the cutting piece 18 is pulled and its nitinol knife engages with the artificial chordae line 14 as well as one strand of a papillary anchor holder suture 72. The papillary anchor 9 is now free from the adjustment and cutting device 18, 20.

The use of the Z shaped nitinol fork 20 to hold the locking segment 28 open allows the suture/chordae pathway to get a very gentle curve. It also allows the suture to come out of the device in line with the gripper opening. This is important to get as good as possible load conditions on the papillary anchor (Chorda comes out of the anchor in the correct place for optimal holding strength).

In one embodiment the cutter 18 is made from a thin sheet nitinol, which allows the blade to be pulled around a curved surface, to allow a minimal footprint of a relative long sliding action component (it can be pulled for example perpendicular to the cutting surface, taking up much less space). The Z-fork 20 can be produced from a laser cut heat set Nitinol sheet part, where certain sections can be grinded thinner, to obtain different thickness and flex along the part. It is possible to add in a simple temporary wire lock, when pulled it will gently squeeze the chordae 14 in order to maintain its temporary adjusted length, in addition to hold the wire that is connected to the chordae 14 on the outside (not in illustrations). Note that the supports inside the adjustment device 21 are not shown. The chamfer on the top part of adjustment "box" will allow the device to find the anchor 9 if it needs to be retrieved.

In one embodiment a push out tube connected to the papillary anchor 9 contains several markers that can be used as a rough reference point on the distance between the papillary anchor and the leaflet anchor, this could allow the physician to roughly adjust the chordae prior to do the final adjustments as they normally have a hunch about how long the final chordae length should be.

To prevent the cutter 18 from exceeding its desired range of motion, the cutter 18 may be equipped with two stopping features disposed at an upper and lower end of the cutter 18. To prevent the cutter 18 from moving further than its upper position in the housing, a cutter wire may be threaded through the housing and/or the cutter to stop the cutter 18 in an upper position. Even if the cutter wire were to break, the cutter 18 and a wire attached to the cutter operating it cannot escape from an upwards end of the housing as both are contained within the housing. To prevent the cutter 18 from moving further than its lower position in the housing, a cam may be used.

The shaft of the part of the catheter device 2 which houses the cutter 18 and the adjustment device 21 (not shown) can be constructed with two lumens: one chordae lumen and one cutter lumen. The construction can be reinforced with braiding around the chordae lumen (the shaft may also include any lumens required to house pullwires used for operating the device, which may also be reinforced with braiding). In addition to the braiding, a wire made out of Kevlar or another similar material may be implemented in the construction running along the length of the shaft, to increase the tensile strength of the device 2. Additionally or alternatively, a composite tube may be positioned around the lumens. The components and tubing of the shaft can also be embedded in a soft polymer, such as Pebax (e.g. by Pebax reflow), to allow for sufficient flex. The composite tubing may also be anchored in the distal end to prevent the tubing from being torn out of the soft polymer during actuation of the cutter wire. The composite tubing may be anchored in the distal end with, for example, a flat ribbon coil, a stainless steel hypotube ring, or a stainless steel collar.

The braid around the chordae lumen may comprise a laser cut hypotube, which increases the tensile and compression strength of the of the shaft construction. The laser cut hypotube can be 'flex tailored' such that different sections have different flex patterns to accommodate a desired movement of the shaft. The laser cut hypotube can also be welded directly onto the head of the cutter 18. The strong bond between the cutter head and the laser cut hypotube allows for more reliable retrieval of the papillary anchor if readjustment is desired. A braided composite tubing may be disposed outside the laser cut hypotube to form the wire lumens.

In some cases the natural chordae could be a problem for the device. There is a risk of fouling if one of the existing chordae is caught in the hole provided for the exit of the new artificial chordae line 14. One way to eliminate this is to have a one-way chord exit so that the artificial chordae line 14 can only go out of the device, and not in, although this feature is not essential.

Inside the papillary housing 8 there may be small notches in the walls to hold the pins of the papillary anchor 9 and prevent the papillary anchor 9 from rotating so that the pins could fold out in the opening for the new chord 14.

As set out above, one form for the anchor is a grapple hook shape. Another possibility with particular advantages for the leaflet anchor 10 is an anchor with an elongate shape, such as a slim straight body or an elongate tubular form. Examples of such anchors 10 are shown in FIGS. 23 to 28. The elongate anchor 10 can be used in place of the grapple hook shaped anchor 10 discussed above, and thus for example can be used in the catheter device and paired with a papillary anchor as shown in FIGS. 1 to 22.

Figure 23:
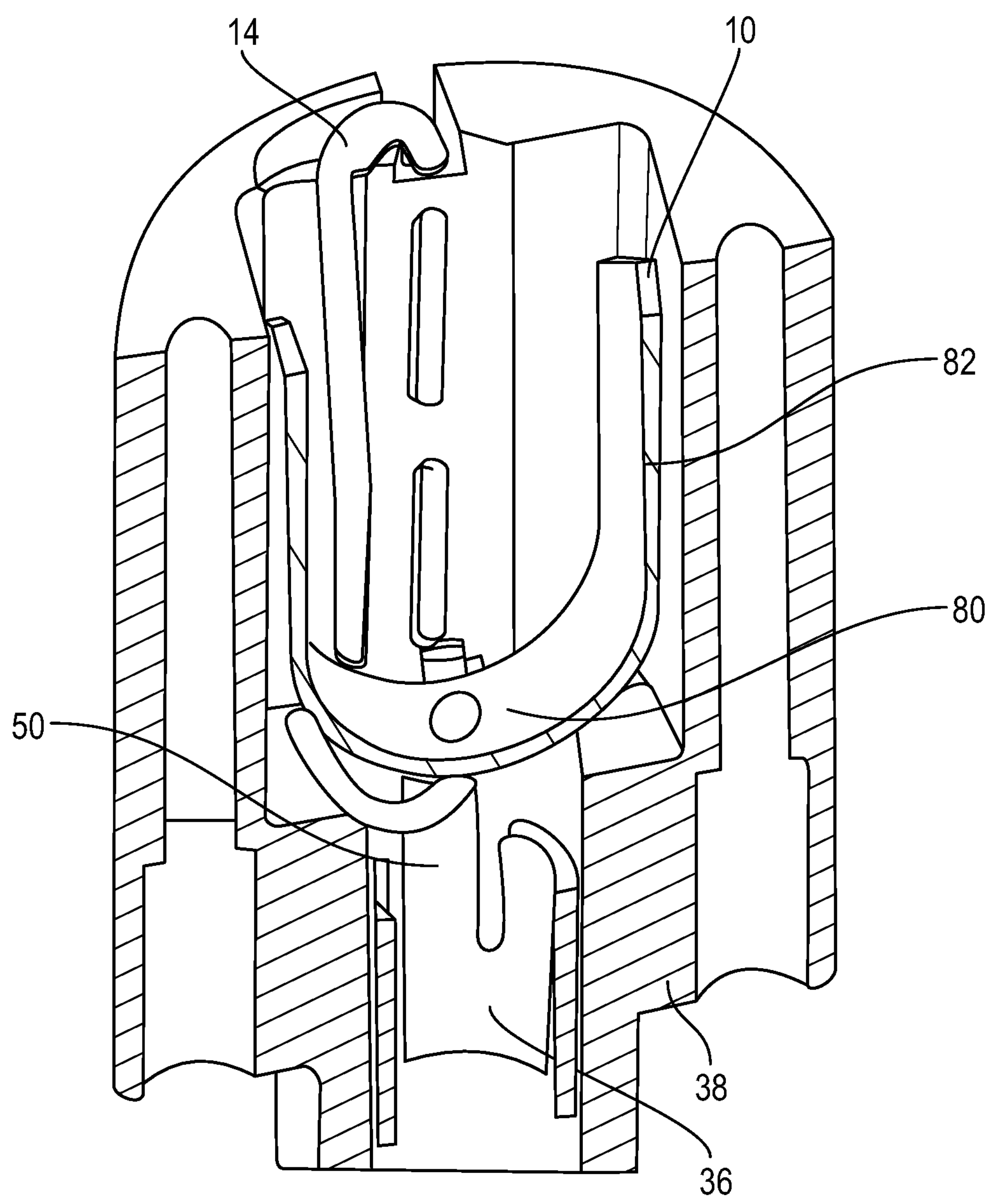
FIG. 23 is a cross-section of a leaflet anchor deployment mechanism using a leaflet anchor with a straight form when unfolded.
Figure 24:
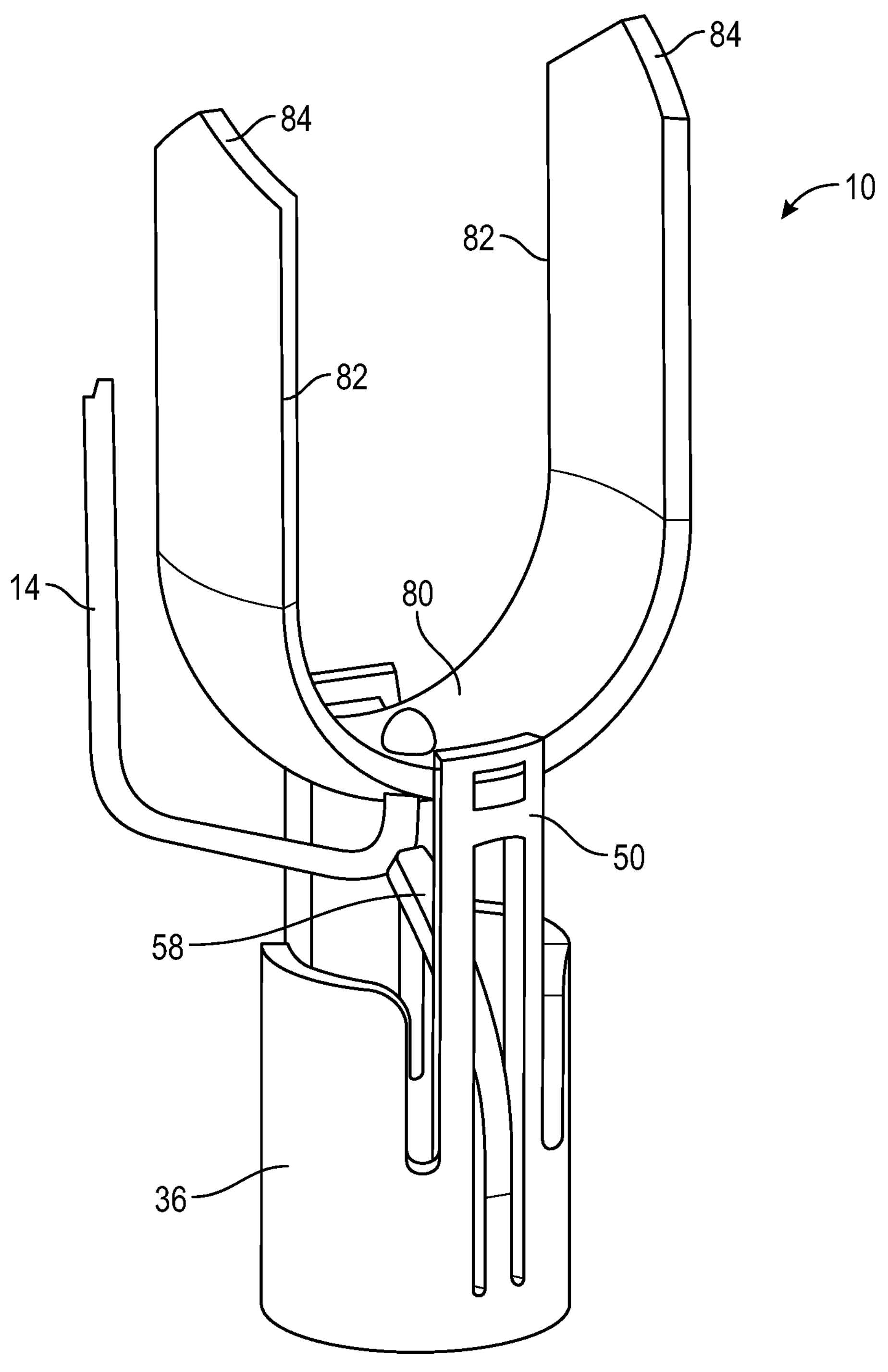
FIG. 24 shows the leaflet anchor and ejector unit of FIG. 23 with the leaflet anchor tube omitted.
Figure 25:
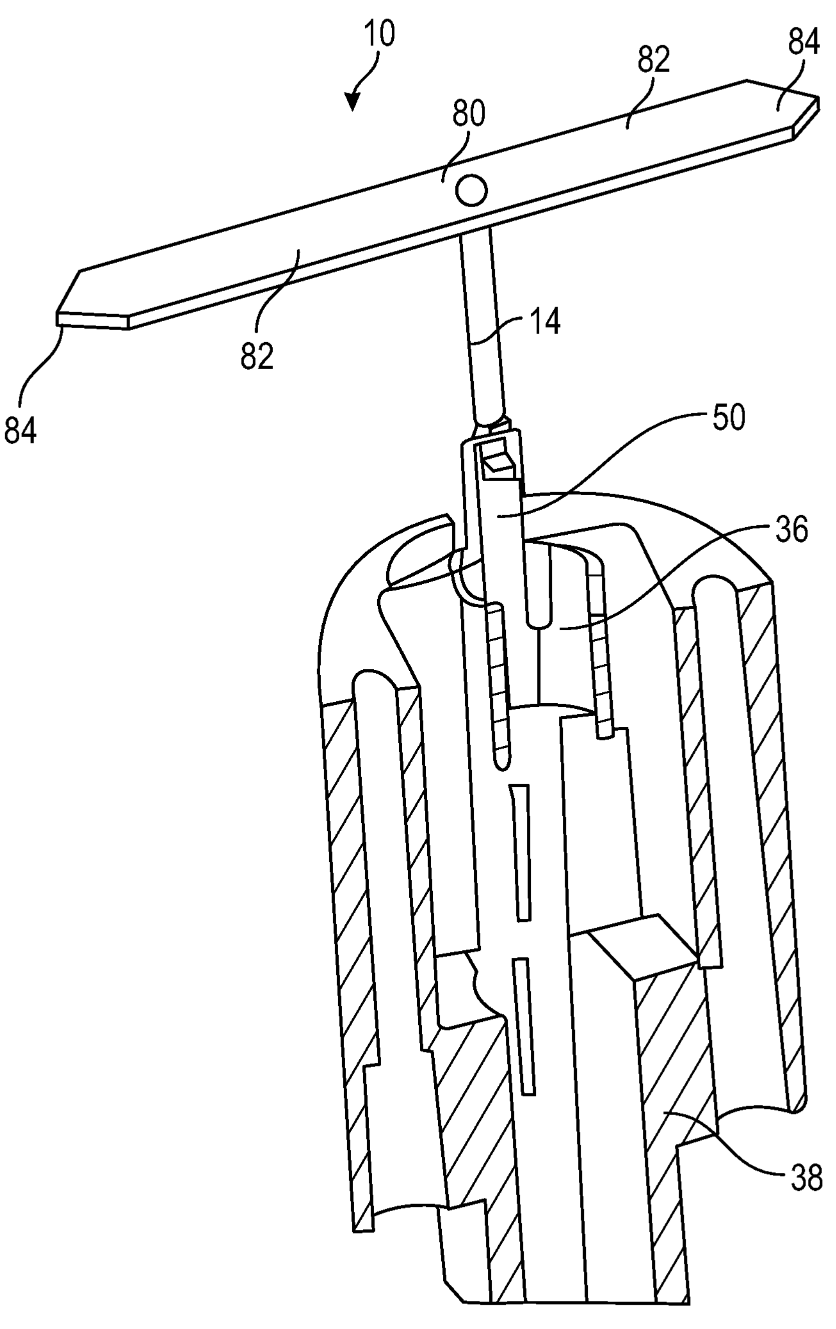
FIG. 25 shows the leaflet anchor of FIG. 23 after deployment.
Figure 26:
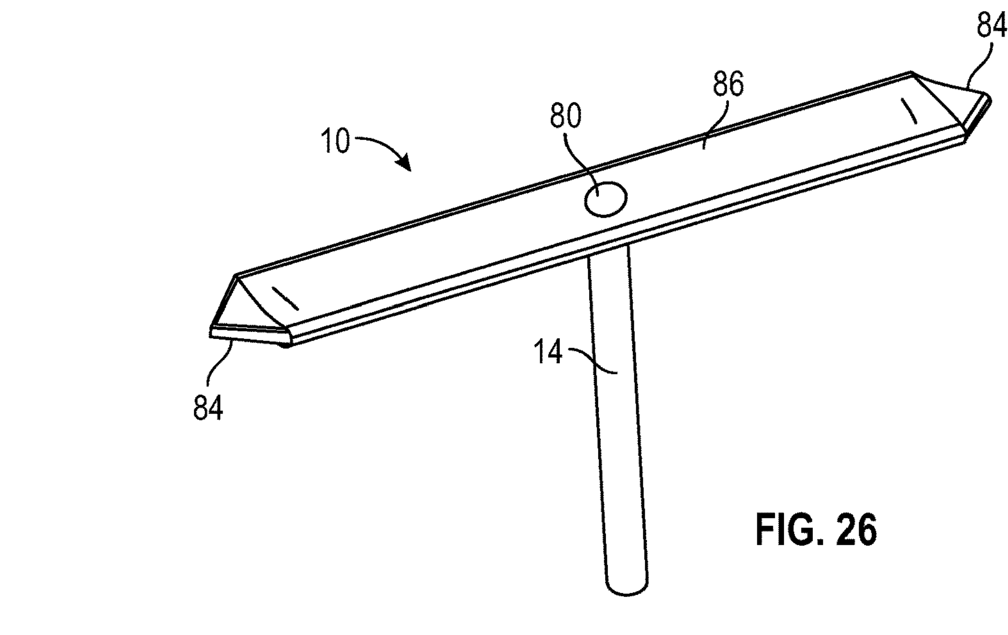
FIG. 26 illustrates the leaflet anchor of FIG. 23 with a covering about the anchor.

FIGS. 23 to 26 show one advantageous form of elongate anchor 10 in use as a leaflet anchor 10. The leaflet anchor 10 of FIGS. 23 to 26 has an unfolded configuration for placement within the body tissue, which is shown in FIGS. 25 and 26, and a folded configuration for use prior to deployment of the anchor 10, which is shown in FIGS. 23 and 24. The unfolded configuration is a U-shape and is permits placement of the anchor 10 into an anchor tube 38 prior to deployment using a similar mechanism to the leaflet anchor deployment mechanism described above. Thus, the example implementation uses an ejector unit 36 that grasps the leaflet anchor 10 via a grasping device 50, and the ejector mechanism 36 also includes a suture pusher (line pusher) 58. The anchor 10 is attached to an artificial chordae line 14, which can in turn be attached to a papillary anchor as discussed above. The function and structure of the leaflet anchor deployment mechanism is generally as discussed above, aside from that the anchor has a different form as shown.

The elongate leaflet anchor 10 can be elastically deformed into the folded configuration with a U-shape as shown in FIGS. 23 and 24, with FIG. 23 showing a cross-section including the leaflet anchor tube 38, and FIG. 24 showing the folded configuration with the leaflet anchor tube 38 omitted from the drawing. The elongate leaflet anchor 10 includes two pins 82, which form the arms of the U-shape in the folded configuration. There are sharp tips 84 at the end of each of the pins 82. The fold of the U-shape is centred on the anchor's centre 80, which is where the artificial chordae line 14 is attached. The ejector unit 36 grasps the elongate leaflet anchor 10 at either side of the centre 80 via hooked arms 50 similar to those described above. The anchor elongate leaflet 10 is held in the U-shape by application of a constraining force from the walls of the leaflet anchor tube 38, and it will return to the unfolded configuration when no constraining force is applied, which occurs when the elongate leaflet anchor 10 has been pushed out of the end of the leaflet anchor tube 38. FIG. 25 shows this configuration, with the ejector unit 36 also having been moved to its second configuration in order to release the elongate leaflet anchor 10. As noted above, the ejector unit 36 can have a form and function as described above, for example as described in connection with FIGS. 8 to 12. In the unfolded configuration the elongate leaflet anchor 10 straightens out into an elongate configuration in which the two anchor pins 82 extend in opposite directions to each other, preferably parallel and opposite to one another, with one pin 82 at either side of the centre 80, where the line 14 is attached.

Thus, when the elongate leaflet anchor is in its folded U-shape and it is advanced out of the end of the leaflet anchor tube 38 via the leaflet anchor deployment mechanism then the ends 84 of the anchor pins 82 will pierce the leaflet 12 and pass through it. As the centre 80 of the elongate leaflet anchor 10 approaches and then passes beyond the end of the anchor tube 38 then it will straighten out into the shape shown in FIG. 25. Hence, when the elongate leaflet anchor 10 assumes the unfolded configuration the elongate form will be threaded through the leaflet 12 with outer parts of the two pins 82 one side of the leaflet 12, and the centre 80 of the elongate leaflet anchor 10 as well as central parts of the two pins 82 on the opposite side of the leaflet 12.

FIG. 26 shows a possible further advantageous feature, where the elongate leaflet anchor 10 is enclosed with an ePTFE sheath 86. The purpose of the ePFTE sheath 86 is to promote tissue growth into and around the anchor during healing, as well as to protect the anchor 10 and allow it to be retained in a single piece in the event of a fracture. The sheath 86 is attached to the main body of the anchor 10 by sutures.

In the example of FIG. 23 to the anchor is formed from an elongate plate with a curve across its width. The curvature across the width is used to increase the stiffness of the anchor and hence to increase the force with which the anchor pushes back toward the unfolded configuration. Once the anchor is folded the bottom curvature will become flat, which means that further folding needs only a relatively small force. The original curvature impacts on the amount of elastic strain in the anchor material when it is flat, which in turn affects the elastic forces that urge the anchor to return to the unfolded configuration. A typical curvature might be in the range 1-5 mm radius for a thickness of the plate in the range 0.05 to 0.5 mm. To obtain a curved plate the anchor may be formed from a flat plate that is deformed and heat set. Alternatively a curved plate could be provided as a section cut from a tube of the required curvature. The latter approach can involve fewer manufacturing steps since pre-existing tubular sections can be used to provide the required curvature.

Figure 27:
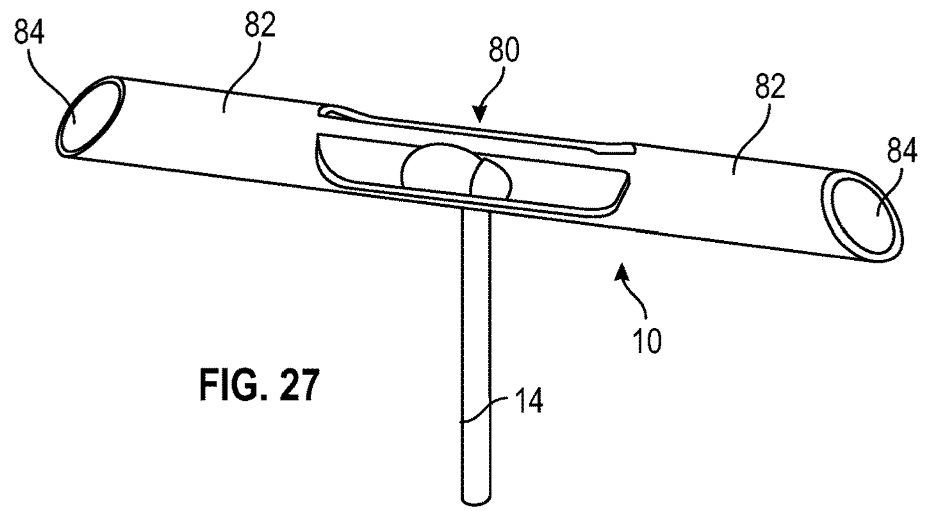
FIGS. 27 and 28 show an alternative form for a straight anchor in the unfolded and folded configurations.
Figure 28:
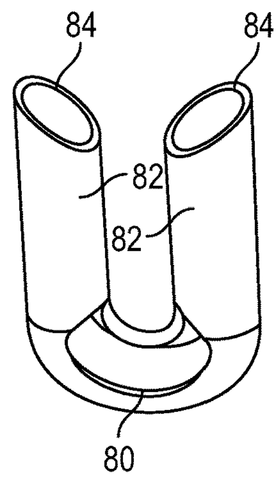

In an alternative example, as shown in FIGS. 27 and 28, an elongate leaflet anchor 10 can be formed from a tubular body with a weakened section at its centre 80 to allow for elastic bending of the tube. This elongate leaflet anchor 10 can be folded into a U-shape and unfolds into an elongate generally straight form as for the elongate leaflet anchor 10 of FIGS. 23 to 26, and it will be appreciated that it may be deployed via a leaflet anchor tube 38 and ejector unit 36 as discussed above. To provide sharp ends 84 of the pins 82 then diagonal cuts are made across the tube, leaving sharp ends 84 similar to those on hollow needles. The weakened section at the centre 80 of the tube can be provided by cutting one or more openings into the tube, such as shown in FIGS. 27 and 28.

Figure 29:
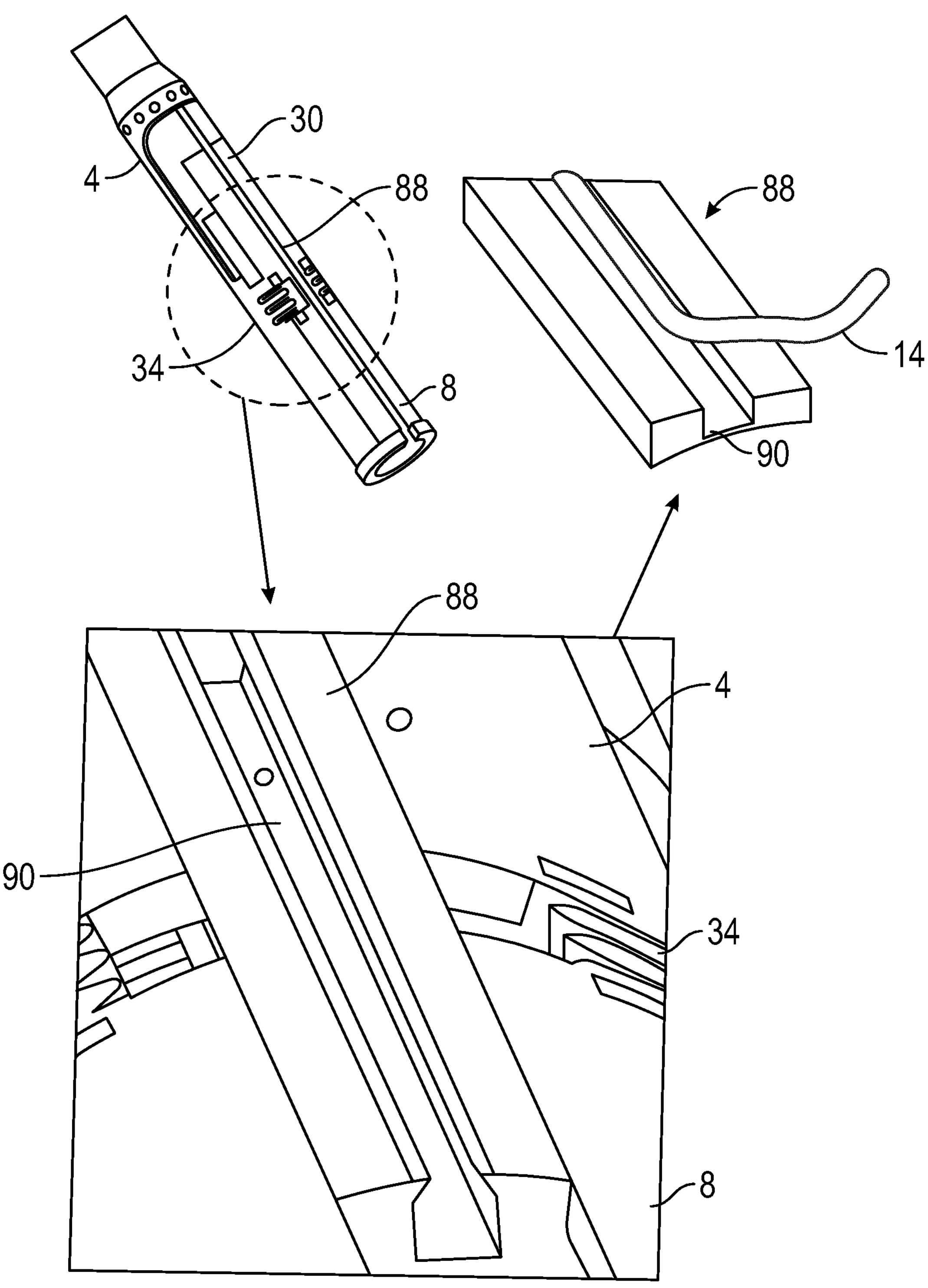
FIG. 29 shows a catheter device similar to that of FIGS. 4 to 6, modified via the use of a sliding chordae holder.

A possible further feature of the catheter device is shown in FIG. 29. This is a sliding chordae holder 88 that can be used in the pathway of the artificial chordae line 14 through the flexible and extendable joint 34 and down to the papillary anchor 9 in the distal part 8 of the housing. The sliding chordae holder 88 is fixed in place relative to the proximal end of the device and hence does not move relative to the proximal part 4 when the flexible and extendable joint 34 extends. It then slides relative to the distal part 8 of the housing. The sliding chordae holder 88 reduces the risk of pinching the artificial chordae line 14 in the flexible and extendable joint 34. As best seen in the lower enlarged section the sliding chordae holder 88 includes a channel 90 that holds the artificial chordae line 14. Further, as best seen in the upper right view, where the housing is omitted, the sliding chordae holder 88 has a profile formed with side rails for guiding the sliding movement.

In addition the sliding chordae holder 88 can reduce the risk of pinching the line 14 in any other flexible joints, such as a flexible hinge section that moves with the gripper arm 30 in the proximal housing part 4. A suture push out device can be provided to allow for the user to selectively push out the artificial chordae line 14 from channel 90 of the sliding chordae holder 88. In that case a thin line may be placed below the artificial chordae line 14 in the channel 90, with the thin suture being connected to a small sliding wedge such that when pulled the wedge moves inside the channel 90 in order to push the artificial chordae line 14 of out the channel 90. This feature allows the user to choose the point at which they release the artificial chordae line 14 from the device, which further reduces the risk of entanglement.

It would also be possible to use the thin wire in order to split open an initially closed channel by breaking along a weak point or by unfolding the tube about a slit. That could mean that the artificial chordae line 14 is initially enclosed, but when the wire is pulled then a protective cover is opened or otherwise removed from the outer surface of the channel 90 and allows the artificial chordae line 14 to escape the channel 90, or to be pushed out via the suture push out device.

Figure 30:
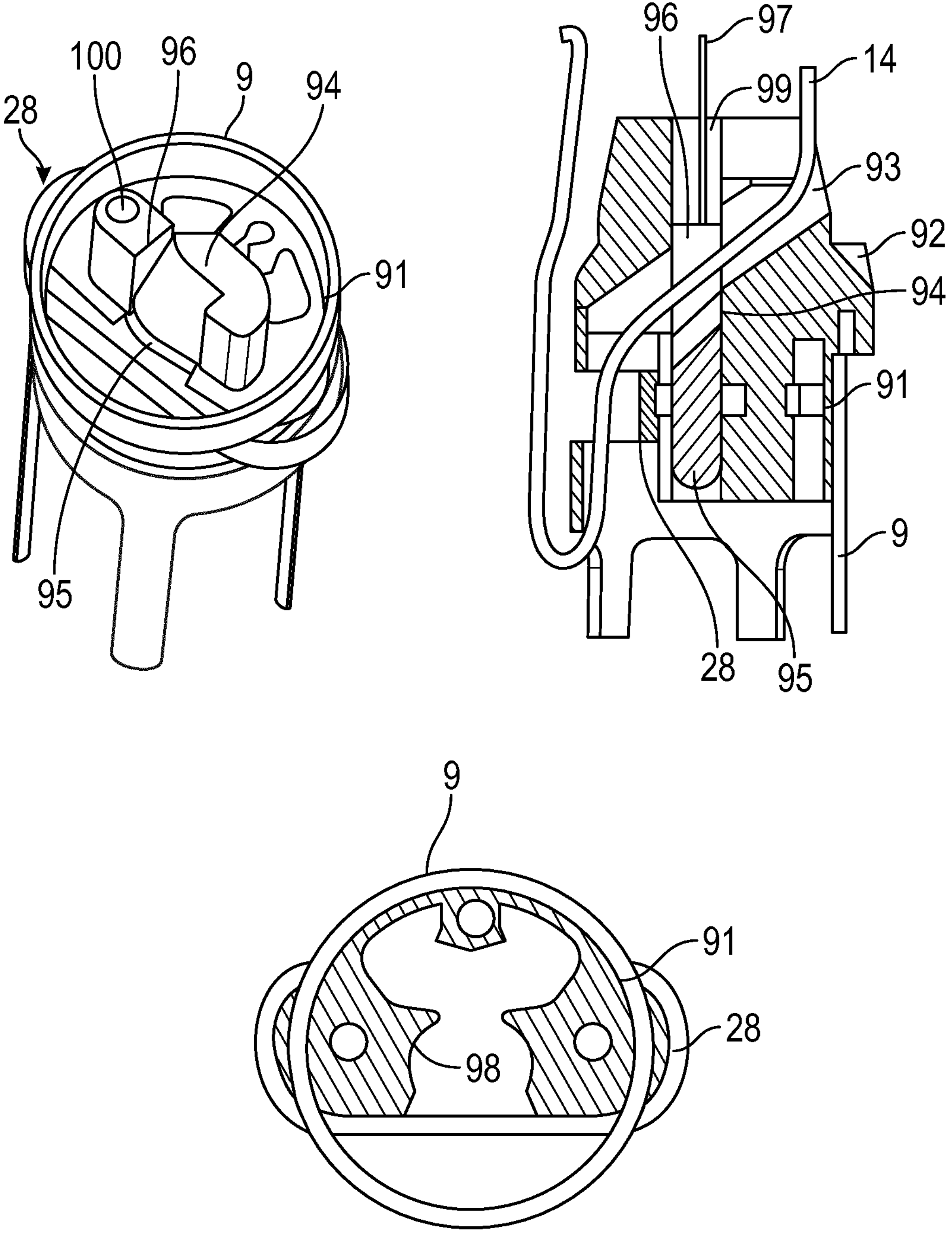
FIG. 30 shows another example of an adjustment and cutting catheter together with the papillary anchor.

FIG. 30 shows an alternative way to arrange the adjustment and cutting catheter 21 with features together with the papillary anchor 9. The arrangement shown holds the line clamping mechanism in an open position, fixes the papillary anchor 9 to the adjustment catheter 21 and provides a way to cut excess line 14.

An internal cam 91 may hold the papillary anchor locking segment 28 in an open position, i.e. with the slit open, and the cam 91 advantageously performs several tasks at the same time. The cam 91 can open the slit of the locking segment 28 as well as fixing the papillary anchor 9 to the adjustment catheter 21. In addition a cutting section 94 can be fitted to the cam wedge 95 that holds the cam 91 in the open position allowing the excess artificial chordae line 14 to be cut in the same movement. This reduces the need for wires going through the adjustment catheter 21. The cam 91 is held in place and supported by a holder that prevents the cam from twisting and or bending when actuated. The adjustment housing 92 may have protruding features or an interference fit around its perimeter that snaps in place with support brackets inside the distal part of the device, to allow the adjustment catheter 21 to extended the flexible and adjustable joint 34 then push out the papillary anchor 9, once the right amount of counter-pressure is exerted by tissue on the distal part 8 of the catheter device.

In this example the papillary anchor 9 locking segment 28 is held open with an internal cam 91. The cam 91 has a rest position (not shown in FIG. 30, but note that there is a similar arrangement in FIGS. 41 and 42 below) and one open position, as shown in FIG. 30, with the cam 91 in its open position the papillary anchor 9, and locking segment 28 are held open by internally applying a constraining force. The cam 91 is held in place by a housing 92 that supports the cam 91 structurally during its travel. In addition the adjustment housing 92 contains a line channel 93 and a sliding channel 99 for a combined cutting and cam wedge piece 96/95. When the cam wedge 95 is engaged with the cam's wedge-grooves 98 the anchor locking ring 28 is held open, the artificial chordae line 14 may then be threaded through the line channel 93 and through the open locking rings 28 with relatively free passage. Once a wire 97 connected through attachment hole 100 in the cutting wedge 96 is pulled, the wedge 95 disengages from the wedge-grooves 98 and the cam 91 returns to its rest position, clamping the line 14 and releasing the papillary anchor 9 from the adjustment housing 92. During the release of the cam 91, or immediately after, the cutting knife 94 engages with the line 14. The cam 91 and cutting wedge 96 may have a cylindrical shape, to accommodate tight tolerance machining. One or both of the cutting edges may also be fitted with flat or circular blades. An additional two legged fork structure (not shown) connected to the wedge 96 that holds locking segment 28 open may also be included to make sure the locking segment 28 of the anchor is completely open while the suture 14 is adjusted.

The adjustment housing 92 may have protruding features or an interference fit (not shown) around its perimeter that snaps in place with features in the distal part 8 of the device, to allow the adjustment catheter 20 to extended the flexible and adjustable joint 34 then push out the papillary anchor 9, once the right amount of counter-pressure is exerted by tissue 26 on the distal part 8 of the device. It will be understood that the arrangement of FIG. 30 can be combined with any of the prior embodiments for the catheter device in place or other arrangements for holding the papillary anchor 9 and for operating the locking ring 28.

The adjustment housing 92 may have a groove (not shown) for a locking tab (not shown) that holds the papillary anchor 9 in place to prevent it ejecting too early as previously described. The locking mechanism can be a tab connected to a torque wire that locks into the papillary anchor 9. A suitable locking mechanism might include a latch as described below with reference to the device of FIGS. 34 to 36.

A variation of the design of the two-part housing section of the catheter device 2 is shown in FIG. 31 and FIG. 32. FIG. 31 is a side view of the housing section with a flexible joint 34' angled and the gripper device 6 open. FIG. 32 shows the two-part housing section in a straight configuration, with a chordae channel 90' visible. This design for the two-part housing section may be used in place of the flexible and extendable version described above, with other features of the device remaining the same. It has been found that it is possible to reliably complete implantation of both of the anchors in a single procedure using such a device, where the flexible joint 34' allows the distal end to be angled toward the papillary muscle 26 for implantation of the papillary anchor 9 without the use of an extension of the distal end. This variation also illustrates the possible use of different materials, since the two-part housing section(s) and the gripper may be formed from a composite such as fibre reinforced PEEK, which again may be a variation applied to other arrangements for the catheter device 2 as discussed above. This type of composite material can give greater visibility of the device via ultrasound imaging during image guided surgery, with the visibility optionally further enhanced by added reflection enhancing features such as the use of dimples 102 as shown. The two parts of the two-part housing section are joined by a hinge element 104, which can be actuated via one or more wires (see FIG. 46). Pull wires that actuate the device may beneficially be threaded around the hinge element, which provides a low friction transition in the pulling direction. Other features of the device can be similar to those discussed above, such as the gripper mechanism 6, and the anchor deployment systems.

Figure 33:
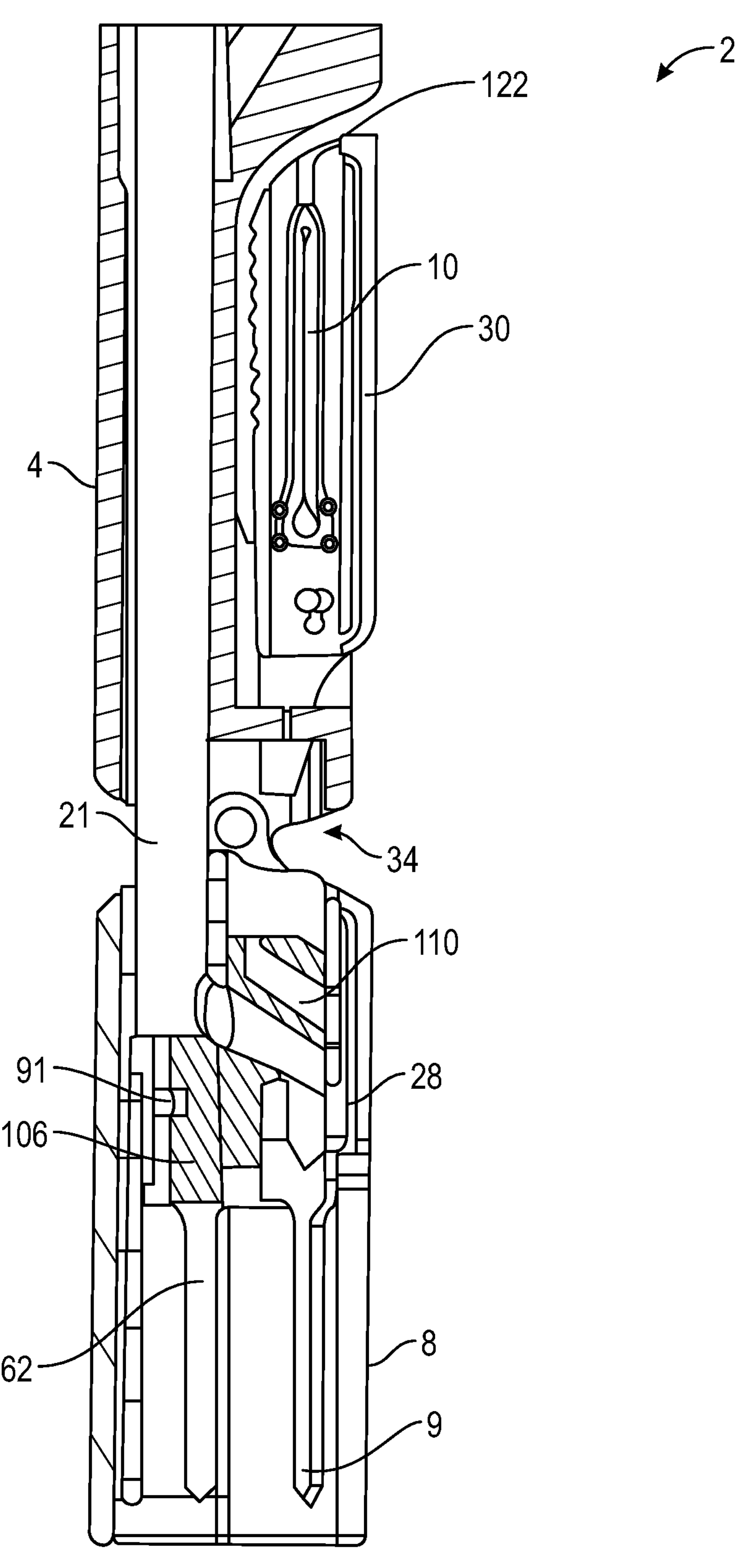
FIG. 33 shows another example of a catheter device with a cross-section through a housing section thereof.

FIG. 33 shows a cross-section view of another example of a catheter device 2. The gripper arm 30 may be seen engaged with the gripper housing 4 in a closed position, ready to deploy the leaflet anchor 10.

The leaflet anchor channel, inside the gripper arm 30 may be produced with one or more anti-rotation grooves 122 in the form of one or more slits or grooves 122 running along the inside of the leaflet anchor channel in the gripper arm 30. The grooves 122 assist in preventing rotation of the leaflet anchor 10 during its deployment when engaged with a suitable engaging mechanism (not shown). In this example at least one of the tips of the hooks of the leaflet anchor 10 slide inside the groove(s) 122, preventing the leaflet anchor 10 from rotating. A non-circular oval shape (not shown) may also be utilised to prevent unwanted rotation of the leaflet anchor 10.

Figure 34:
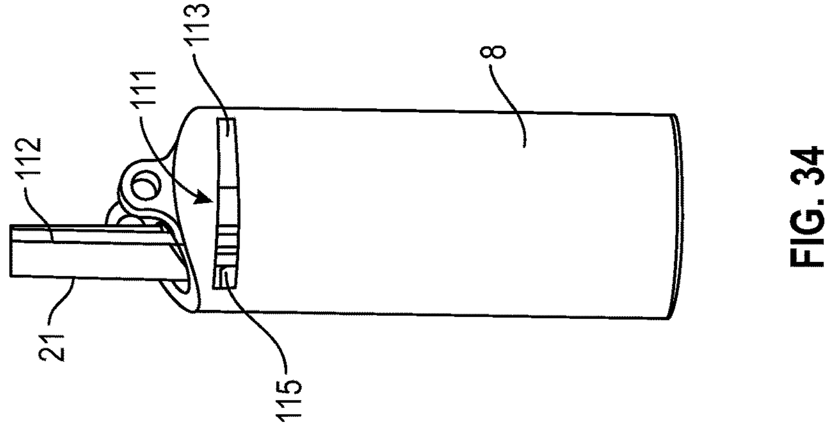
FIG. 34 shows a distal part of the housing section of the device of FIG. 33.

Running through the catheter device 2 of FIG. 33 and into a distal end of the catheter device 2 is an adjustment catheter 21. As described above, the adjustment catheter 21 is able to control the extension of the flexible joint 34 by means of wires and/or rods 60. The same wires and/or rods 60 also push out the papillary anchor 9 for deployment. As described above, the papillary anchor 9 comprises a number of pins 62 that in an unconstrained configuration form a number of hooks, and further comprises a locking segment 28 disposed within a wall of the papillary anchor 9. The papillary anchor 9 is housed within the papillary anchor housing 8. Further housed within the papillary anchor housing 8 is an adjustment housing 92. The adjustment housing comprises a piston 110, an anchor holder 106 and a cam 91. To prevent unwanted deployment of the papillary anchor 9, a deployment lock mechanism 111 using a latch 113 may be disposed within the papillary anchor housing 8, as shown in FIG. 34. The deployment lock mechanism 111 is actuated via a locking spring that acts on the latch 113 and a deployment lock wire 112. The latch 113, the locking spring, and the deployment lock wire 112 may be formed from a suitable elastically deformable alloy such as nitinol. The latch 113 is engaged with a recessed slot 115 of the papillary anchor housing 8 in order to lock the adjustment housing 92 in place relative to the housing 8. The deployment lock wire 112 may be situated within the adjustment catheter 21 for operating the latch 113. The deployment lock wire 112 extends from the latch 113 to the proximal end of the catheter device 2. The deployment lock wire 112 may also be enclosed in a flexible tube (not shown) which may assist in facilitating reengagement of the deployment lock wire with the latch 113, if necessary.

Figure 35:
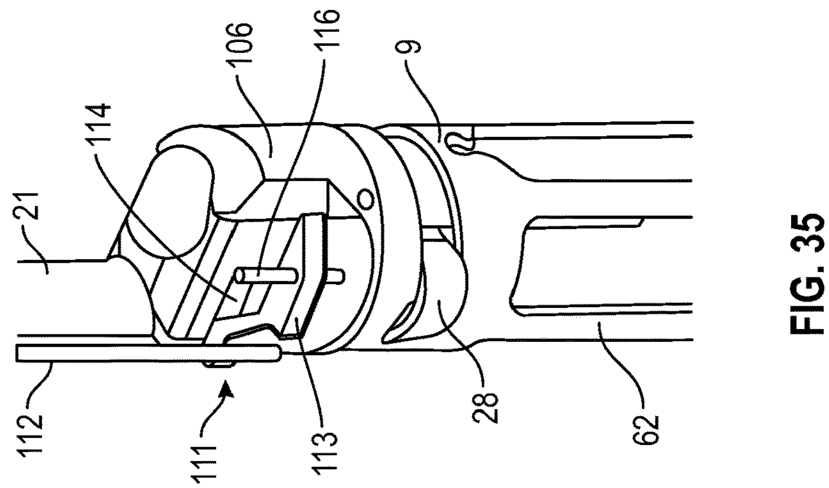
FIG. 35 is a perspective view of an anchor and adjustment housing of the device of FIG. 33, with the housing section omitted to show detail of the anchor in the stowed position.

FIG. 35 shows the deployment lock mechanism 111 in a locked position without the papillary anchor housing 8. A retainer pin 116 permanently constrains one end of the latch 113 to be engaged with the papillary anchor housing 8, and acts as a pivot for the latch 113. The deployment lock wire 112 temporarily constrains the other end of the latch 113 to be engaged with a chamfered cavity 114 of the anchor holder 106, the anchor holder 106 capping the end of the papillary anchor 9 opposite to its hooks.

Figure 36:
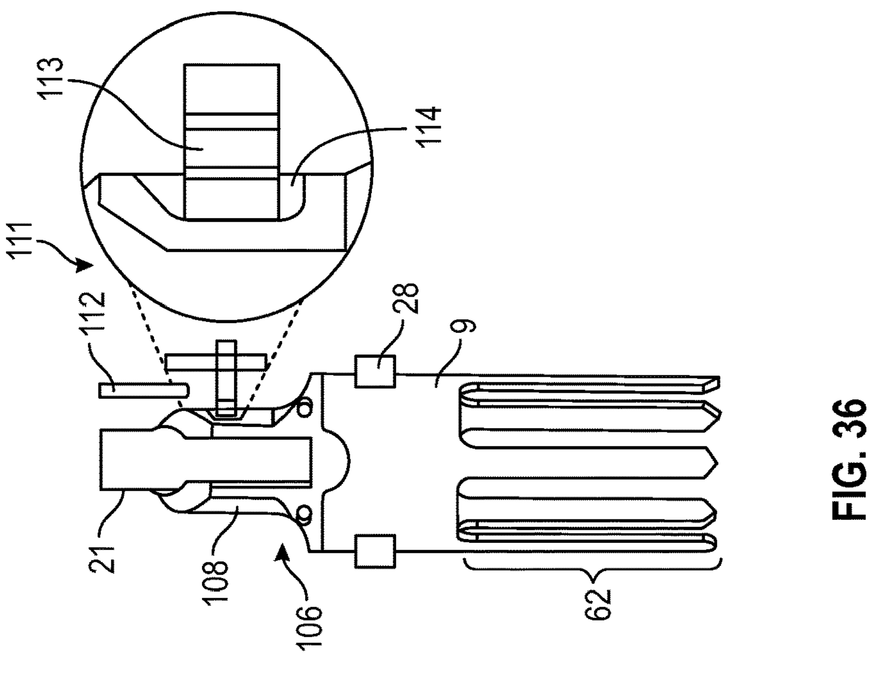
FIG. 36 illustrates a side view of an anchor and adjustment housing of the device of FIG. 33, with the housing section omitted and a deployment lock wire in a retracted position.

As shown in FIG. 36, the deployment lock wire 112 may be retracted. Once retracted the deployment lock wire 112 no longer constrains the latch 113 to engage with the chamfered cavity 114 of the anchor holder 106. The locking spring can then move the latch 113 as set out below.

Shown in a magnified illustration within FIG. 36, without constraint from the deployment lock wire 112 the latch 113 only rests within the chamfered cavity 114 of the anchor holder 106. When a forward pressure from the wires and/or rods 60 within the adjustment catheter 21 are operated, a forward pressure is applied to the anchor holder 106 and papillary anchor 9, which in turn releases the anchor holder 106 from the latch 113. This is achieved due to the shape of the chamfered cavity 114 deflecting the latch 113 during the deployment motion. Advantageously, if an operator of the catheter device 2 wishes to reengage the deployment lock mechanism 111 with the anchor holder 106; a chamfer on the proximal end of the anchor holder 106 may deflect the latch 113 in order to reengage with the chamfered cavity 114 in its rest position. The deployment lock wire 112 may then be reengaged with the latch 113. As such, the deployment lock mechanism 111 may suitably be engaged and disengaged as required to allow or prevent deployment of the papillary anchor 9.

It will be appreciated that the lock deployment wire 112 may be used to constrain the latch 113 against the chamfered cavity 114, whereby the latch 113 instead has an undeformed position whereby it does not rest within the chamfered cavity 114. However, if the latch 113 is in an open configuration at rest the capability of the deployment lock mechanism 111 to be reengaged may be lost.

Figures 37, 38:
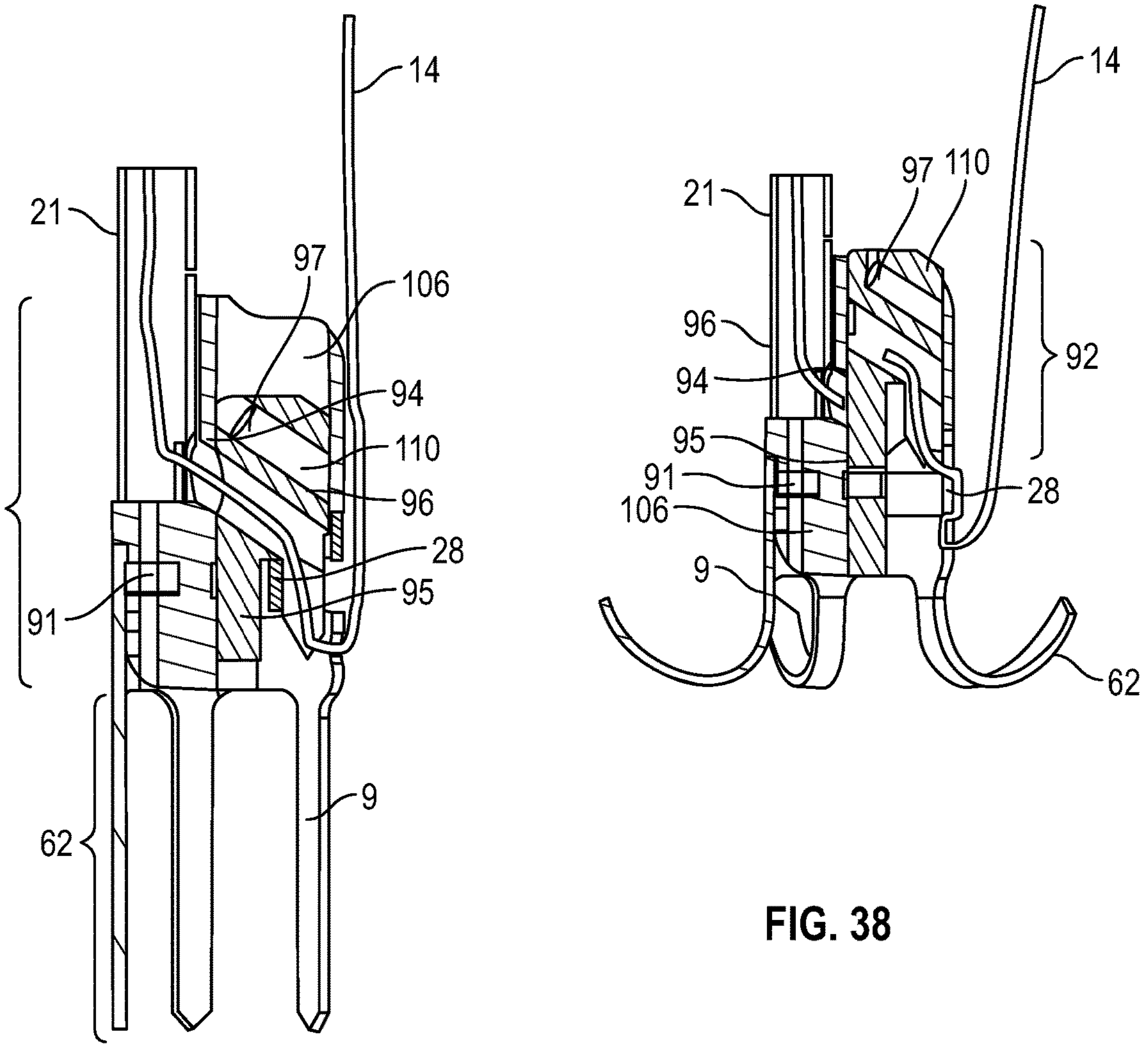
FIG. 37 is a cross-sectional view of a papillary anchor when undeployed with an adjustment housing mounted on top.
FIG. 38 shows a cross-section similar to FIG. 37 with the anchor in the deployed, unfolded state.

FIG. 37 illustrates a cross-sectional view of the papillary anchor 9 when undeployed with the adjustment housing 92 mounted on top. Contained within the adjustment housing 92 is an anchor holder 106, a piston 110 and a cam 91. The piston 110 comprises a fork-wedge formation 95, which is configured to elastically deform the cam 91 and the papillary anchor 9, and a cutting wedge 96, which is configured to cut the chordae 14 in combination with a cutting section 94 of the anchor holder 106. The fork-wedge can be considered with two main parts, a cam wedge where at least one tine of the fork-wedge 95 is used to open the cam 91, and a piston wedge where at least one tine of the fork-wedge 95 is used to open the locking segment 28. The pointed end of the piston wedge advantageously assists in deflecting the locking segment 28 when the piston wedge and the locking segment are engaged, making engagement/deployment of the anchor 9 with the piston wedge easier. When the cam 91 is engaged by the fork-wedge 95, the cam 91 elastically deforms the locking mechanism 28 of the papillary anchor 9 to an open position. In the configuration shown in FIG. 37, the open locking mechanism 28 and the positioning of the piston 110 within the adjustment housing 92 allows the chordae 14 to slide through with minimal friction. The chordae 14 is attached to the leaflet anchor 10 (not shown) above the papillary anchor 9. In this configuration the chordae is thus easily adjustable in length. The piston 110 ideally features a piston wire location 97 which allows a pull-wire (not shown) to be attached to the piston 110. The pull-wire is ideally disposed through the adjustment catheter 21 (inside a separate lumen in the adjustment catheter 21) without running through the path proximal to the cutting wedge 96 and cutting section 94. When the piston pull-wire is pulled, the piston 110 slides in a direction away from the papillary anchor 9.

FIG. 38 illustrates a cross-sectional view of the papillary anchor 9 when deployed with the adjustment housing 92 mounted on top. The piston 110 slidably moves away from the papillary anchor 9 during deployment. In doing so the fork-wedge 95 of the piston is no longer engaged with the cam 91 and the locking segment 28. The cam 91 no longer elastically deforms and the cam 91 as well as the locking segment 28 of the papillary anchor 9 returns to their at rest/undeformed positions. In doing so, the chordae 14 is locked in position and its length is no longer adjustable. Concurrently, when the locking mechanism 28 returns to its undeformed position the cutting section 94 and the cutting wedge 96 cut the chordae 14. Thus in one motion the papillary anchor 9 may be deployed and the chordae 14 suitably attached in place. By disposing the piston pull-wire in the piston pull-wire location 97 above the cutting location, the piston pull-wire may avoid being cut in the same action and thus leaves the device fully operational should readjustment be required.

To prevent the piston 110 from exceeding its desired range of motion, the piston 110 may be equipped with two stopping features disposed at an upper and lower end of the piston 110. To prevent the piston 110 from moving further than its upper position in the housing 92, a cutter wire (not shown) may be threaded through the housing and/or the piston to stop the piston 110 in an upper position. Even if the cutter wire were to break, the piston 110 and a wire attached to the piston 110 operating it cannot escape from an upwards end of the housing 92 as both are contained within the housing 92. To prevent the piston 110 from moving further than its lower position in the housing 92 is the cam 91.

FIGS. 39 to 42 show the adjustment housing 92 and the papillary anchor 9 interactions in more detail.

Figure 39:
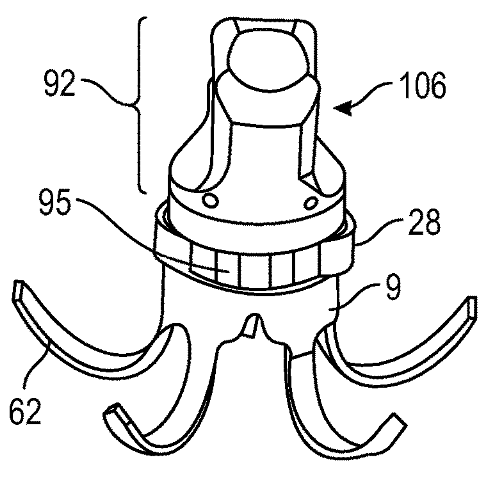
FIGS. 39 and 40 show further details of the adjustment housing of FIGS. 35-38.

FIG. 39 illustrates the adjustment housing 92 mounted on top of the papillary anchor 9 when the papillary anchor 9 hooks are not constrained. The adjustment housing 92 may be formed of a material such as stainless steel or a composite material, such as CRF PEEK or a combination where the cutting edges may be Stainless steel while the structural components may be a composite material. The fork-wedge 95, which in this embodiment comprises three legs but could comprise one or more legs or tines, of the piston 110 is engaged with the locking mechanism 28 of the papillary anchor 9. The fork-wedge 95 prevents the locking mechanism 28 from returning to its undeformed position and thus allows for adjustment of the chordae line 14 passing through it. The cutting wedge 96 is disposed on one of the tines corresponding to the fork-wedge 95.

Figure 40:
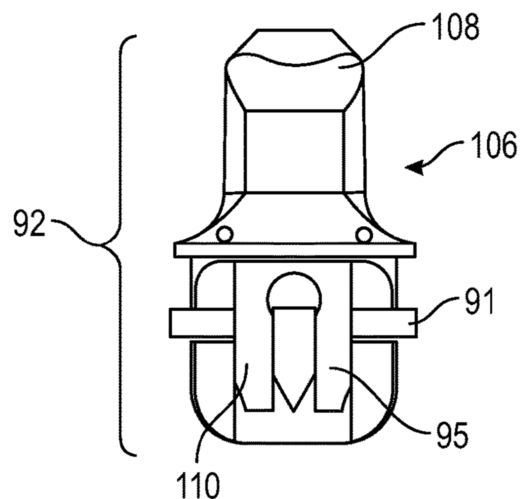

FIG. 40 shows the adjustment housing 92 without the papillary anchor 9. The adjustment housing 92 comprises the anchor holder 106, the piston 110 and the cam 91. The adjustment housing 92 is in an adjustment configuration, shown by the piston 110 engaging with the cam 91 via the fork-wedge 95 to elastically deform the cam 91 to a wide position. FIG. 40 also shows an engaging portion 108 of the anchor holder 106. The engaging portion 108 is shaped such that it fits within the papillary anchor housing in a specific orientation whereby rotation is restricted.

Figure 41:
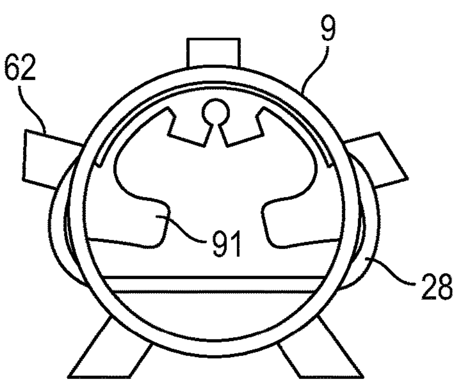
FIGS. 41 and 42 show an internal cam of the adjustment housing.

FIG. 41 is a birds-eye view of the cam 91 engaged with the papillary anchor 9 in the deformed position. The deformation is the result of the piston 110 engaging with the cam 91 via the cam wedge part of the fork-wedge 95. The deformation of the cam 91 constrains the locking mechanism 28 of the papillary anchor to display an ovoid shape. The ovoid shape of the locking mechanism 28 not only allows for the passage of the chordae 14 through the locking mechanism 28 with minimal friction, but also creates a shape of the papillary anchor 9 that may be utilised to restrict rotation of the papillary anchor 9 when disposed within the papillary anchor housing 8.

Figure 42:
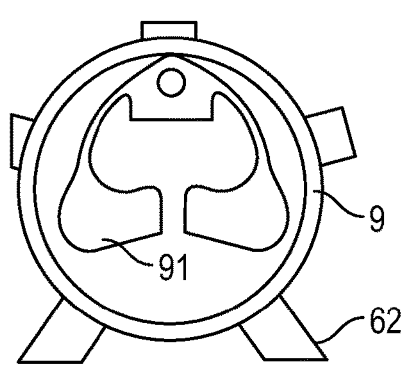

FIG. 42 is a birds-eye view of the cam 91 in its undeformed position. The piston 110 is not engaged with the cam 91 in this configuration. As such the cam 91 does not engage with the locking mechanism 28 of the papillary anchor 9. The locking mechanism 28 when undeformed matches the tubular shape of the papillary anchor 9.

Figures 43, 44:
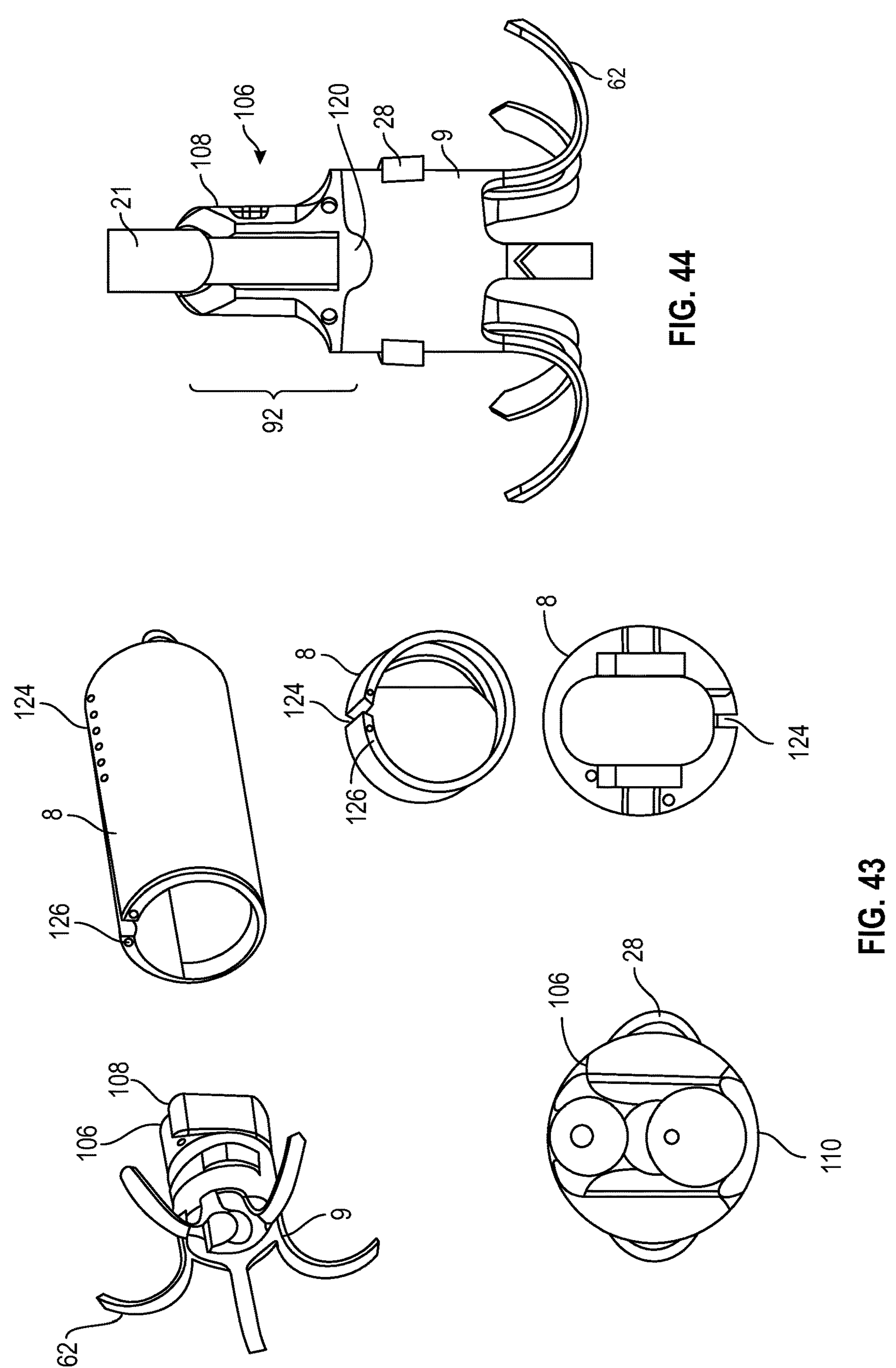
FIG. 43 is an exploded view of various parts of the catheter device of FIG. 33.
FIG. 44 is a side view of the anchor and adjustment housing with the anchor in the deployed, unfolded state.

FIG. 43 shows two perspective views of the papillary anchor 9 with the adjustment housing 92 mounted on top, and three perspective views of the papillary housing 8. The engaging portion 108 of the anchor holder 106 features an ovoid cross-section with bevelled edges. During insertion of the papillary anchor 9 into the papillary anchor housing 8, the curved internal shape of the papillary anchor housing 8 deflects the engaging portion 108 due to the complementary curved shapes. The papillary anchor 9 thus orients itself such that the ovoid shape of the locking segment 28 will then engage with the complementary internal shape of the papillary anchor housing 8.

The internal shape of the papillary anchor housing 8 may be seen clearly in the middle perspective view of FIG. 43, looking from the distal end of the papillary anchor housing 8. Towards the proximal end, a shape complementary to the engaging portion of the anchor housing 106 is graduated from the ovoid shape complementary to the locking mechanism 28. The funneling shape assists in deflecting the engaging portion 108 of the anchor housing 106 such that the correct orientation is easily achieved to insert the papillary anchor 9 within the papillary anchor housing 8. The funneling allows for the correction of relatively large rotational misalignment before the anchor holder 106 engages with the corresponding slot within the papillary anchor housing 8 which greatly restricts rotational movement.

The specific shapes of the locking mechanism 28, the engaging portion 108 of the anchor holder 106 and the internal shape of the papillary anchor housing 8 restrict rotation of the papillary anchor 9. Restricting possible rotation of the papillary anchor 9 advantageously ensures proper alignment of the papillary anchor 9 with the target deployment location. Additionally, the engaging portion 108 of the anchor holder 106 may feature chamfering to assist in more easily inserting the anchor holder 106 into the distal part 8 of the catheter device 2.

Restricting rotation of the papillary anchor 9 may also assist in preventing twisting of the chordae 14, the lock deployment wire 112, the piston pull-wire and the wires/rods 60 used to deploy the papillary anchor 9.

A number of the wires such as the lock deployment wire 112, the piston pull-wire and the wires/rods 60 used to deploy the papillary anchor 9 are disposed in the distal part 8 of the catheter device 2 to ensure proper functionality of the device 2. However, as the distal part 8 of the catheter device 2 is able to actuate to bend and/or extend, slack may be introduced to some or all of the wires/rods used within the device 2 to operate its various components. This can lead to entanglement of the wires which may affect proper functionality of the device 2. To ensure that the wires/rods remain taut, a constant tension device may be used within the device 2. The constant tension device may be disposed in the handle used to operate the device 2. An example of a constant tension device includes but is not limited to a constant force spring.

A constant tension device as described above could also be implemented for use with the U-rod wire 30 which, being disposed in the proximal part 4 of the catheter device 2, is still susceptible to entanglement due to bend or steering of the shaft of the device 2. Similarly, a constant tension device as described above could be implemented for use with the artificial chord 14 when it is disposed in the device 2 before adjustment and deployment.

FIG. 44 shows another view of the papillary anchor 9, when the piston 110 is engaged with the cam 91. The locking mechanism 28 is elastically deformed and protrudes from the wall of the papillary anchor 9. The ovoid shape of the protrusion is utilised to restrict rotation of the papillary anchor 9 within the papillary anchor housing 8. The bevelled shape of the engaging portion 108 may also be seen, which assists with deflection of the anchor holder 106 to ensure correct orientation when inserting the papillary anchor 9 within the papillary anchor housing 8. Also visible is a keyed joint arrangement 120 for guided alignment of the papillary anchor 9 as it engages with the anchor holder 106 of the adjustment housing 92. The circular tubular form of the example papillary anchor 9 fits with a concentric arrangement to an outer cylinder of the distal part of the anchor holder 106. A cut-out in the papillary anchor 9 can interlock with a protrusion on the anchor holder 106 to provide the keyed joint 120. It will be understood that the opposite arrangement of the cut-out and protrusion could also be used.

Figure 45:
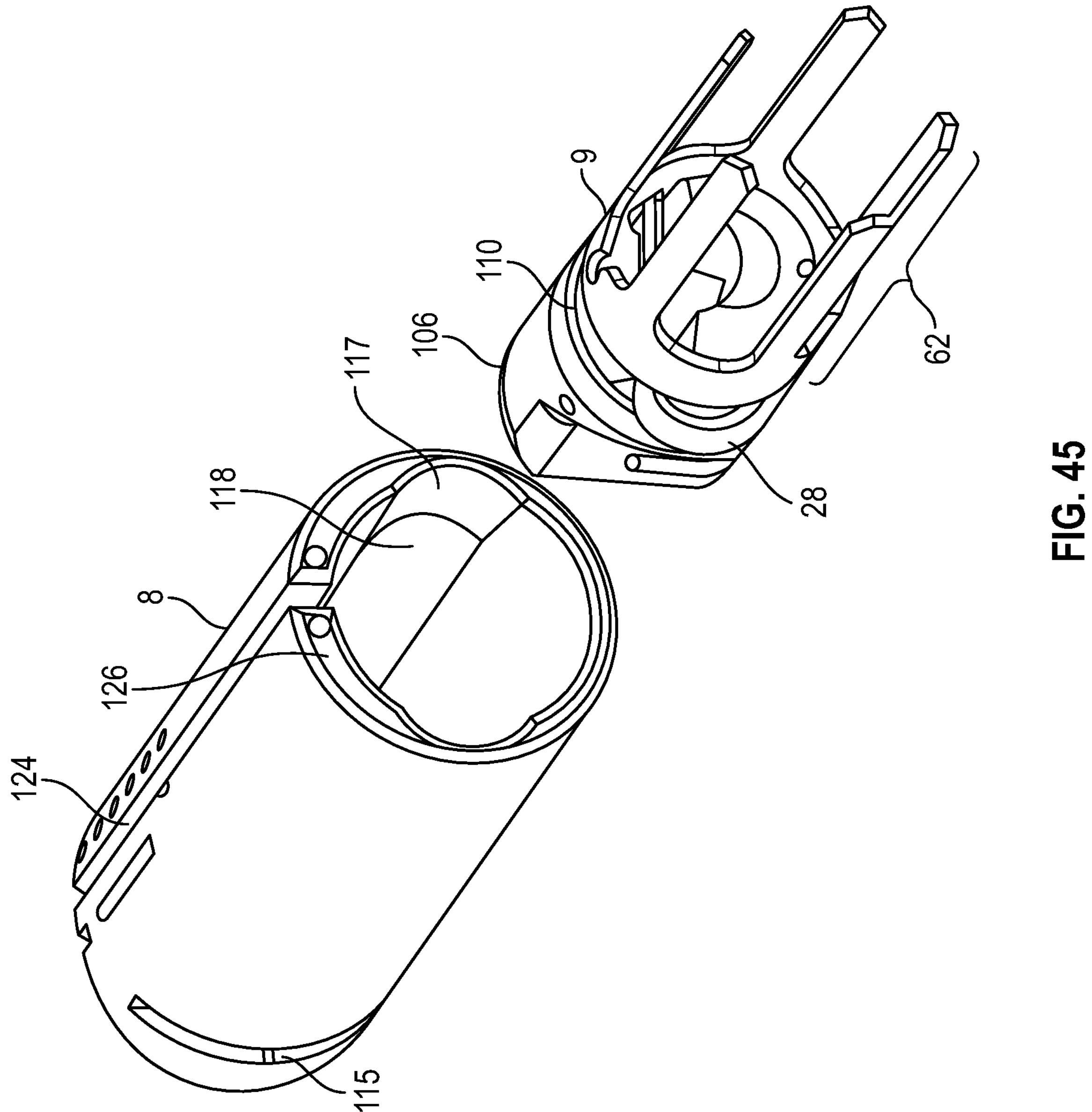
FIG. 45 shows a non-circular shape in the distal part of the device including an engagement funnel.

FIG. 45 shows more detail of possible advantageous features for the distal part 8 of the housing. In this instance the housing includes a non-circular mating groove 118 in the papillary anchor housing 8, which may be formed to allow for engagement with an ovoid shape of the locking segment 28 as discussed above. To allow for guided engagement of the papillary anchor 9 and the anchor housing 108 a funneled section 117 is provided to facilitate rough alignment of the papillary anchor 9. Once the engagement is completed then the a key groove 118 prevents any rotation of the non-circular shaped papillary anchor 9 and/or the anchor holder 106 while it is slid further along the papillary anchor housing 8, i.e. the distal part 8 of the housing. Another feature that is best seen on FIG. 45 is the presence of a chordae channel 124 running along the length of the papillary anchor housing 8. This channel 124 allows space for placement of the chordae line 14. As it is formed via a slit along the length of the papillary anchor housing 8 then it also acts to reduce the rigidity of the papillary anchor housing 8, allowing for some elastic deformation as the anchor 9 is engaged/reengaged. Advantageously, the chordae channel 124 is placed in a thicker section 126 of the wall of the papillary anchor housing 8, with this thicker section 126 being formed due to the non-circular shape of the recess within the housing 8 as well as the fact that this non-circular shape is placed eccentrically, i.e. off-centre with reference to the centre of the outer form of the papillary anchor housing 8.

Figure 46:
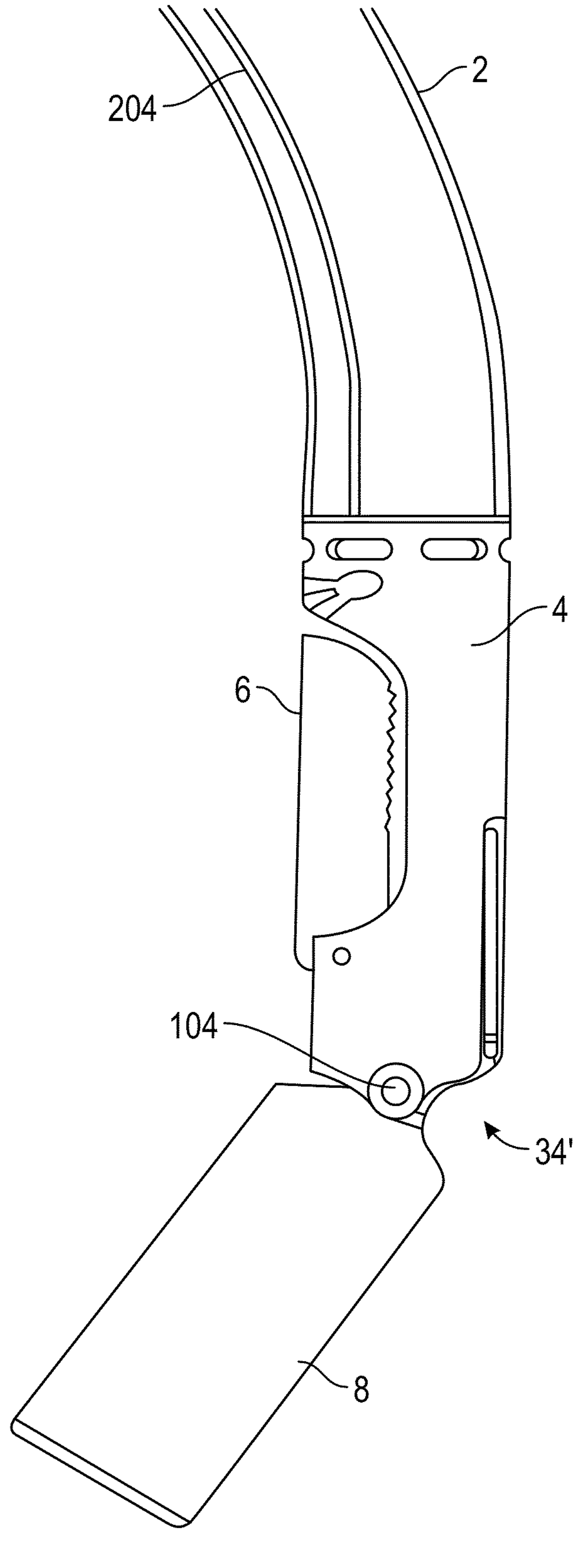
FIG. 46 is a side view of the catheter device displaying how a hinge pullwire may be arranged.

FIG. 46 shows how a hinge pullwire 204 for actuating the hinge element 104 of the flexible joint 34' of the catheter device 2 may be arranged. Although a single hinge pullwire 204 is shown in the figure, more than one hinge pullwire 204 may be utilised to achieve the desired operation of the hinge element 104 of the flexible joint 34'. The hinge pullwire 204 passes through a shaft of the catheter device 2, through the proximal part 4 of the two-part housing section and to the hinge element 104, configured to angle a centreline of the distal part 8 of the catheter device relative to a centreline of the proximal part 4. As described above, the hinge pullwire 204 that actuates the device may be beneficially threaded around the hinge element 104, which provides a low friction transition in the pulling direction.

As can be seen in FIG. 46, the hinge pullwire 204 is off-centre relative to the catheter device 2 and is instead disposed proximate a wall of the catheter device 2. Thus the hinge pullwire 204 is routed to sit inside a front side of the device 2, i.e. the side of the catheter device 2 where the mechanical gripper device 6 is disposed. To angle the distal part 8 of the catheter device 2, the hinge pullwire 204 is pulled. By locating the hinge pullwire 204 inside the front side of the device 2, the shaft of the catheter device 2 is also deflected in the direction the distal part 8 is angled to relative to the proximal part 8. The actuation of the hinge element 104 and the deflection of the device 2 may be sequential or simultaneous during operation of the hinge pullwire 204. For example, during operation of the hinge pullwire the device shaft may deflect at the same time the hinge element bends, or during the operation of the pullwire the hinge element may bend first and the device shaft may deflect second. Beneficially, the shaft of the device 2 may thus be steered by the hinge pullwire 204 as the distal part 8 of the device 2 is angled. Additionally, this assists in ensuring that the distal part 8 is positioned perpendicularly to the target wall of the heart during anchor deployment.

Figures 47A, 47B:
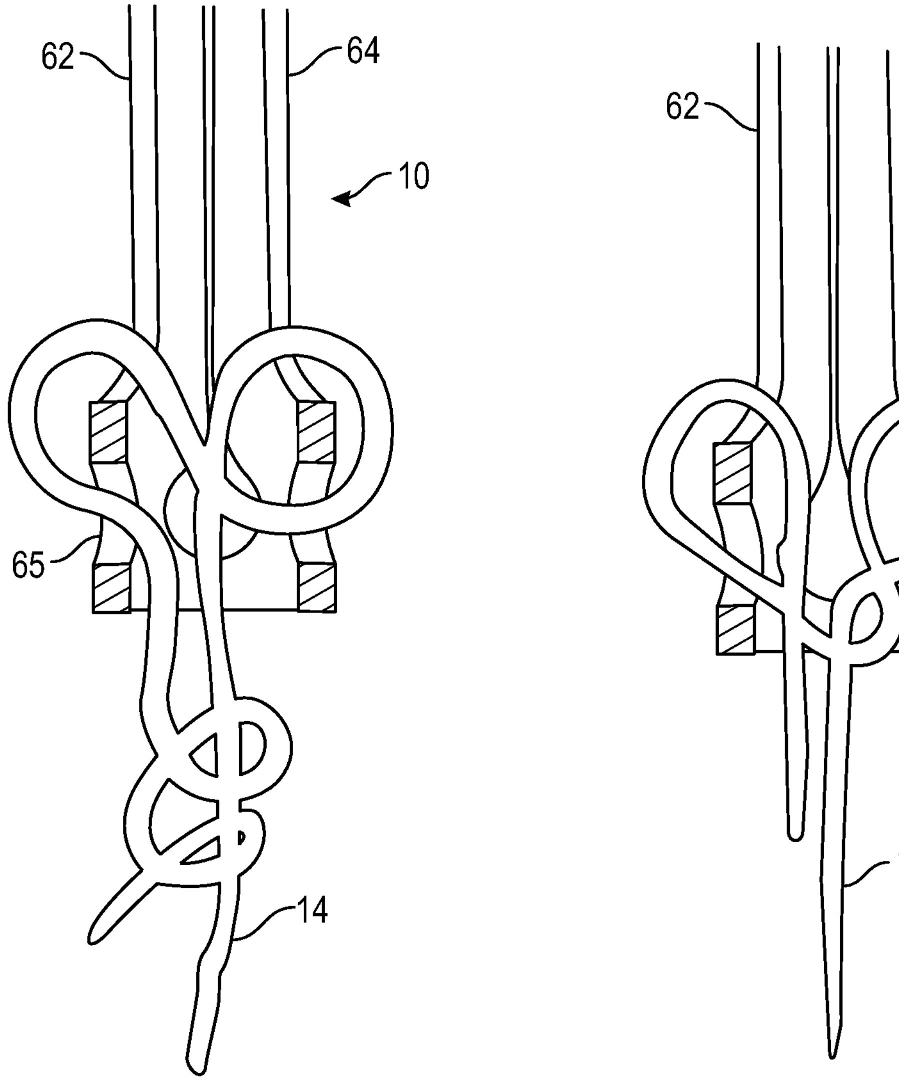
FIGS. 47A and 47B show exemplary self-locking knots which can be used to attach a suture and/or artificial chord to the leaflet anchor.

FIGS. 47A and 47B show exemplary knots that may be utilised to attach an artificial chord 14 to the leaflet anchor 10. The leaflet anchor 10 could be in accordance with any of the embodiments of the leaflet anchor 10 discussed herein. The knots shown in particular are self-locking, i.e. when tension is applied from the end of the artificial chord 14 not attached to the leaflet anchor 10, a stable knot forms. The exemplary self-locking knots shown in the Figures can increase the tensile strength of the leaflet anchor 10 connection by up to a factor of 2.5 times compared to the tensile strength of anchors 10 implementing conventional knots.

Anchor holes 65 located in the base of the anchor 10 accommodate the knot. The holes 65 allow for many threading patterns that give a significant amount of friction to the artificial chord 14. The friction given from the leaflet anchor 10 reduces the change of the artificial chord 14 from slipping out of the anchor holes 65. Over time, ingrowth of tissue in the anchor base and therefore the knot improves the strength of the knot over time.

Figure 48B:
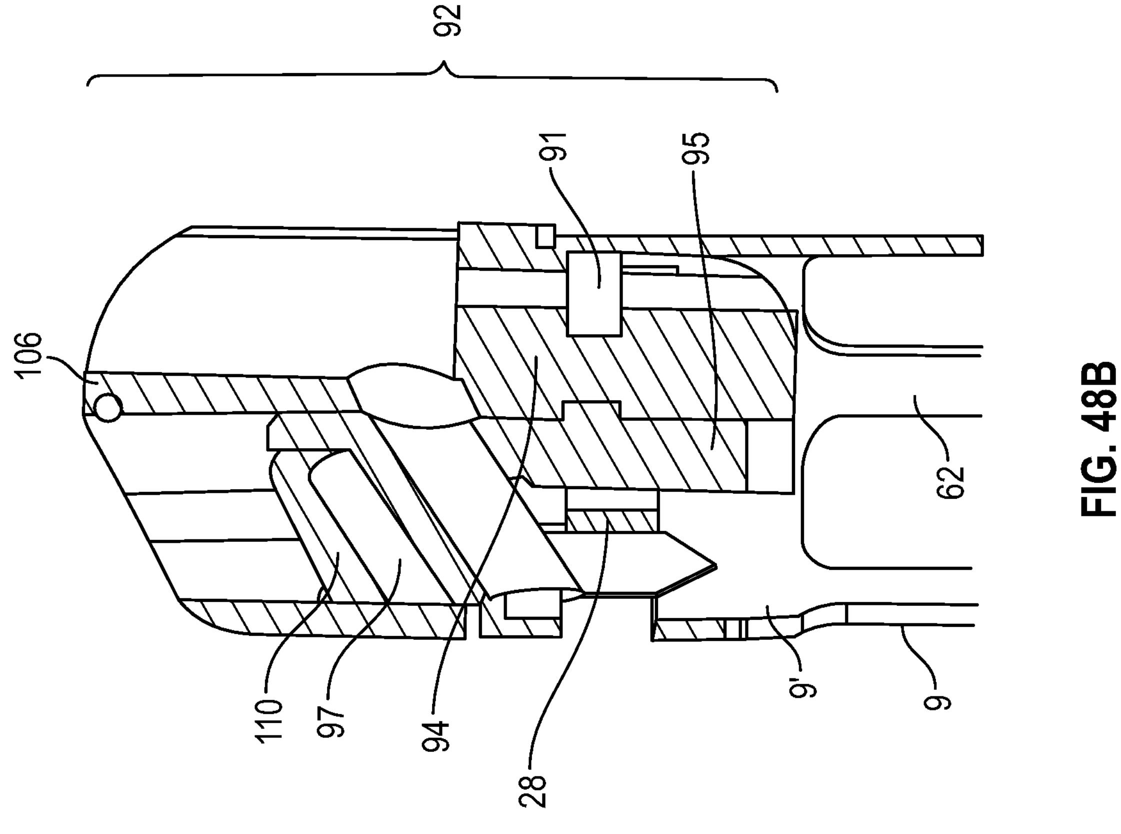
FIGS. 48A and 48B show two different perspectives of the piston wedge engaged with the locking segment, the piston wedge not in contact with an internal wall of the anchor.
Figure 48A:
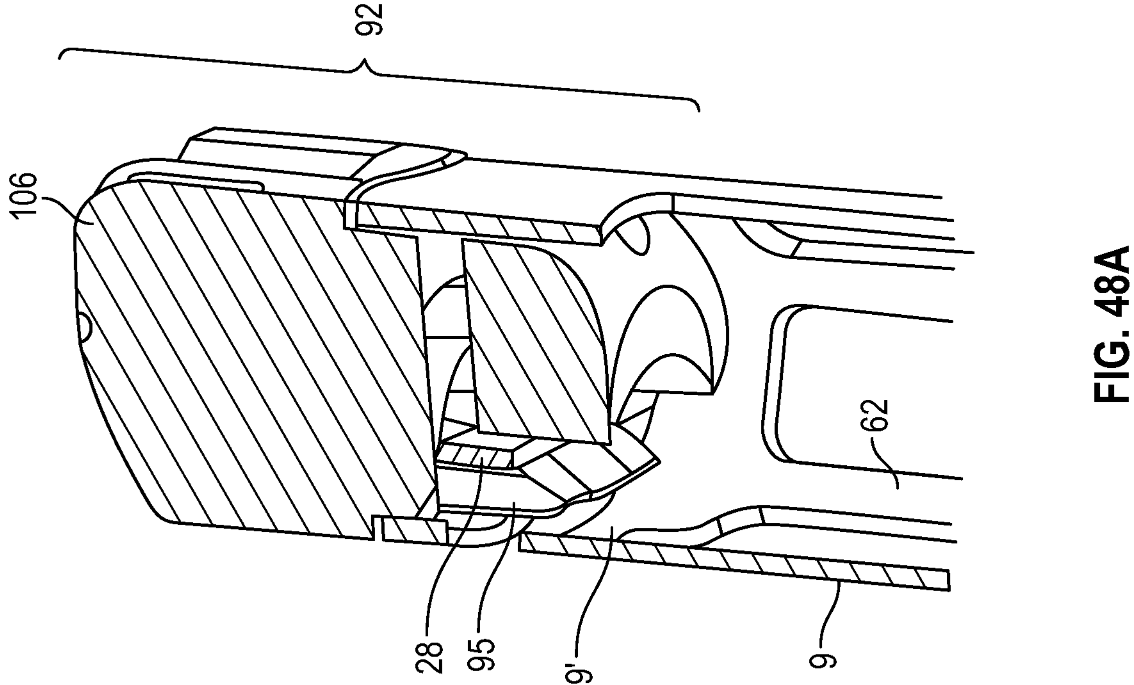

As shown in FIGS. 48A and 48B, the piston wedge of the piston 110 may be arranged such that the piston wedge is never in contact with an internal wall 9' of the papillary anchor 9. When the locking segment 28 is required to be in an open position (e.g. for adjustment of the artificial chord length 14), the piston wedge engages the locking segment 28 without engaging the papillary anchor wall 9'. Advantageously, as there is a smaller contact surface area between the piston wedge and the papillary anchor wall 9' than if the piston wedge were in contact with the wall 9', there is less friction between the piston 110 and the papillary anchor 9. Thus, during deployment of the papillary anchor from the anchor holder 110, the piston wedge does not move with the anchor 9, hence ensuring that the piston wedge disengages with the locking segment 28 in the desired manner.

Still in reference to the embodiment shown in FIGS. 48A and 48B, the locking segment 28 exerts a contact force on the piston wedge, due to its elasticity, which could encourage the piston 110 to move such that the piston wedge contacts the papillary anchor wall 9'. To overcome this undesirable force the piston 110 is arranged in the anchor holder 106 such that the piston 110 acts as a cantilever, preventing the piston wedge from being pulled towards the papillary anchor wall 9'. To ensure that the piston wedge is not bent towards the locking segment 28 by the reaction force of cantilever action provided by the piston 110 in response to the force exerted by the locking segment 28, the piston 110 and the piston wedge may be made of a suitably rigid material. As would be readily understood, the piston 110 of the embodiment as shown in FIGS. 48A and 48B is compatible with any other of the embodiments concerning the piston 110 and its features discussed herein.

As described herein, wires, rods and/or sutures may need to be pulled to be operated and/or adjusted within the catheter device 2. Some of the operations that these components are designed to perform may require a limited force. To aid an operator of the device 2 in knowing when such a force is applied to these components, a clutch can be utilised that releases when a certain torque is released. In various embodiments, it is valuable to allow the operator to know when the clutch is engaging. When the clutch is therefore a ratchet clutch, the operator may be notified that the clutch is engaged due to the clutch producing audible clicks. The type of clutch capable of being implemented in the present invention is not limited to a ratchet clutch and can in fact be any known clutch compatible with the embodiments described herein. For example, an O-ring squeeze clutch may be implemented. In this example, the clutch releases when a certain torque is reached to prevent further force being applied to the wires, rods and/or sutures with which it is engaged.

Figures 49A, 49B:
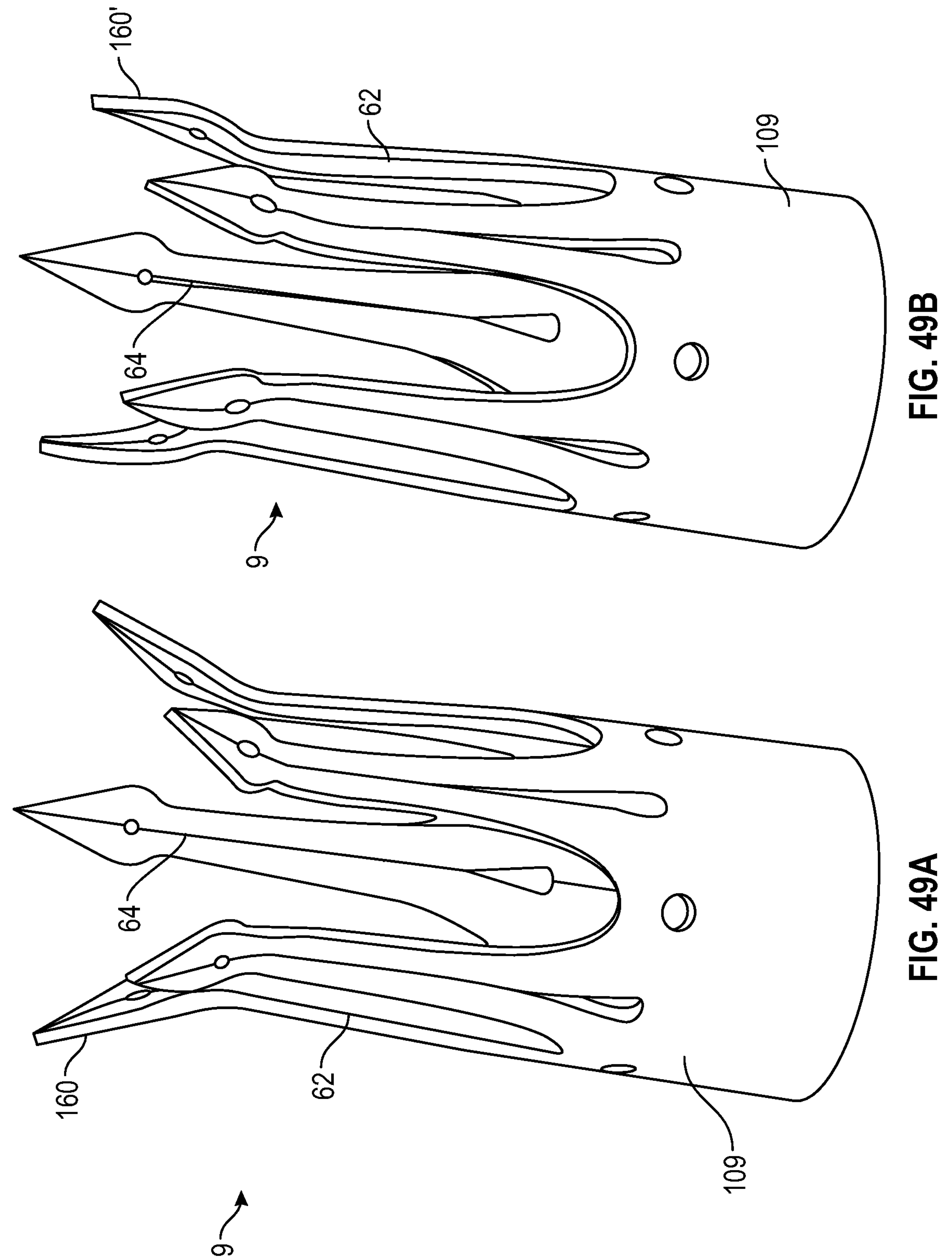
Figure 50A:
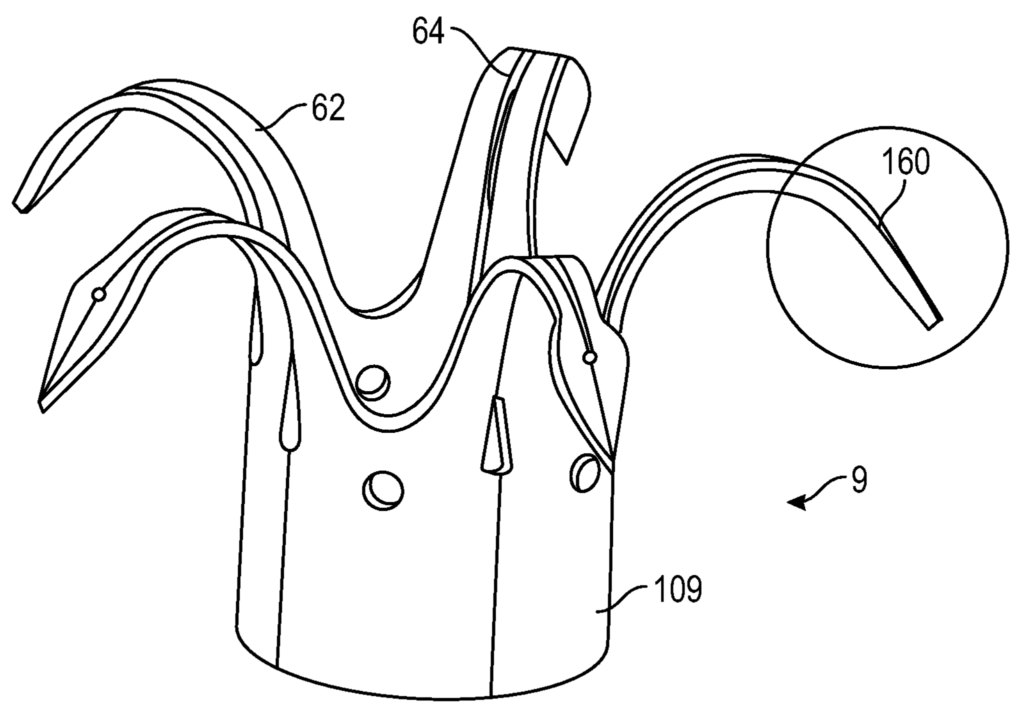
Figure 50B:
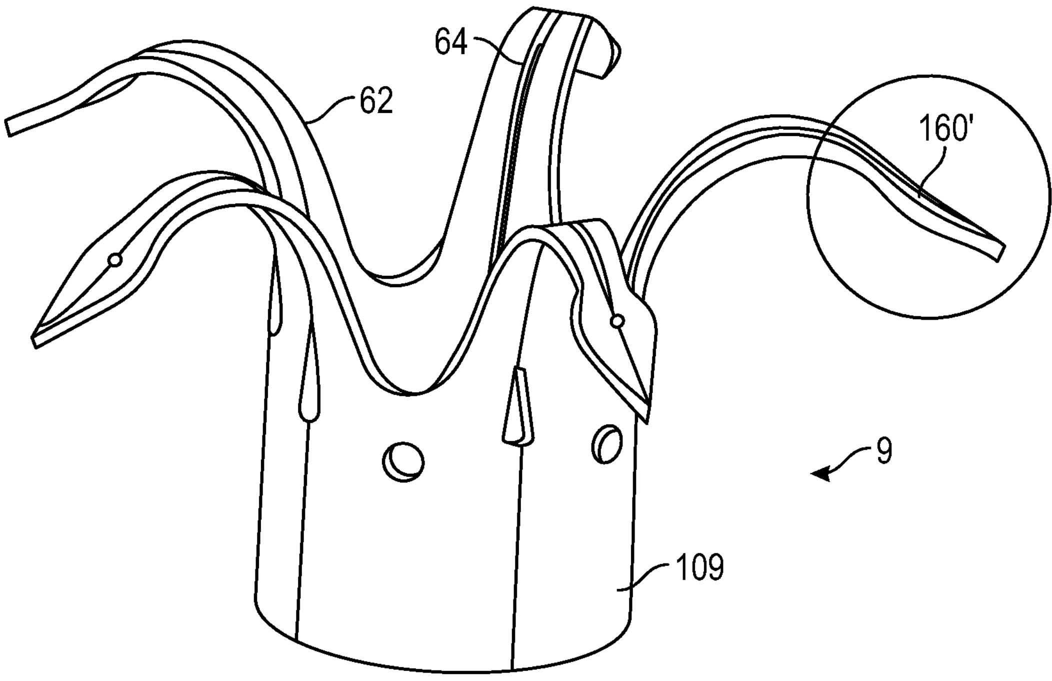
FIG. 50B shows the anchor of FIG. 49B in an unfolded position.

As shown in FIGS. 49A and 49B, an anchor 9 is in a folded configuration. Whilst FIG. 49A shows the anchor 9 having tips 160 which are not curved towards a central axis of the anchor 9, FIG. 49B shows an anchor 9 having tips 160' which are curved towards a central axis of the anchor 9. FIGS. 50A and 50B show how the hooks 62 of the anchor 9 are shaped in the unfolded configuration. FIG. 50A shows the unfolded configuration for tips 160 as in FIG. 49A, whilst FIG. 50B shows the unfolded configuration for tips 160' curved as in FIG. 49B.

Focusing on the anchor 9 shown in FIG. 49B, the anchor 9 comprises a number of hooks 62 which extend from a base 109 of the anchor to a distal end of the anchor. The ends of each hook 62 comprise a tip 160'. The hooks may also have openings 64 running along their length. The tips 160' are curved towards a central axis of the anchor 9, such that when the anchor 9 is constrained by a constraining force in its folded configuration by a container device (for example, the distal part 4 of the catheter device 2 as discussed above) the tips 64 of FIG. 49B do not contact the inner wall of the container device at their pointed ends. Instead, the contact point between the container tube and the anchor 9 is a tangential contact between the tips 160' and/or hooks 62, such that a smoother portion makes contact between the anchor 9 and the container device. As a smoother contact is made, less force is needed to eject the anchor 9 from its housing during implantation in a target body tissue. Additionally, inward curvature of the tips 160' prevents scraping and/or scratching between the tips 160' and an inner surface of the container device. This in turn prevents the production of shavings of the material the container device is made from, which may be deposited in the region around the target body tissue and may otherwise lead to hemorrhaging and/or an embolism that could result in stroke. The production of shavings is most prevalent when the container device is made of a softer material than the anchor 9. For example, this issue arises when the container device is made of CRF PEEK and the anchor 9 is made from either nitinol or stainless steel.

As may also be seen in FIG. 49B, the curvature of the tips 160' curving back towards a central axis of the anchor 9 may assist in ensuring that the tips 160 are perpendicular to a surface of a target body tissue that the anchor is to be implanted in. This minimises an axial force needed to implant the anchor 9, as the force pushing the anchor 9 into the body tissue is more efficiently transferred to the tips 160' of the anchor 9. The force pushing the anchor 9 may be applied by the anchor container tube, the anchor container tube comprising a number of wires and/or rods 60 as described above. The anchor 9 may be deployed via a mechanism as described herein with reference to the other Figures, such as a mechanism including anchor holder 106 and/or a piston 110 as discussed above.

Whilst the curvature of the tips 160' seen in FIG. 49B are shown as being perpendicular, it will be appreciated that the tips 160' of the anchor 9 may be angled relative to a surface of a target body tissue that the anchor is to be implanted in, i.e. curving towards the central axis of the anchor 9. Thus, the curvature of the tips 160' may be in the range of 0 to 30 degrees to the normal of the surface of the target body tissue that the anchor 9 is to be implanted in. In various embodiments the range of values the curvature of the tips 160' could take may be 0 to 5 degrees, 0 to 10 degrees, 0 to 15 degrees, 0 to 20 degrees, 0 to 25 degrees or 5 to 15 degrees.

The curvature of the hooks 62 and the tips 160' of the anchor 9 assists in pulling the anchor 9 through the target body tissue during implantation. This effect is realised due to a 'springback' force exhibited as the anchor 9 unfolds from its folded configuration to its unfolded configuration. As the tips 160' display curvature towards the central axis of the anchor 9, the hooks 62 are pulled through the tissue during unfolding of the anchor 9. As a result the force required during implantation of the anchor 9 in a target body tissue is reduced. It will be appreciated that a consideration of the advantages achieved by the tips 160' of the anchor 9 being angled versus perpendicular to a surface of the body tissue for implantation is to be considered such that the force required to implant the anchor may be effectively reduced.

Anchors 9 having hooks 62 which do not curve back towards a central axis when in a folded configuration (as shown in FIG. 49A) tend to immediately bend back into their unfolded configuration (as shown in FIG. 50A) without penetrating any particular distance into the target body tissue, unless a large amount of axial force is applied to the anchor 9 during implantation. However, anchors 9 having hooks where the tips are formed to curve towards a central axis (as shown in FIGS. 49B and 50B) will tend to penetrate a larger distance into the target body tissue before the tips 160' of their hooks 62 begin to curve outward from the central axis as they move into their unfolded configuration (as shown in FIG. 50B), because the inward curvature of the tips 160' causes the first penetration of the tissue to be inward and/or parallel with the axis of the anchor 9. Thus, a reduced axial force is required to be applied to the anchor 9 from the container device to cause the initial penetration of the anchor 9, and in some cases this may be no force with the unfolding of the anchor 9 acting to draw it into the tissue so long as a distal end of the container device is in contact with a surface of the target body tissue. The springback force of the anchor 9 resulting from the inward curvature of the tips 160' facilitates a trajectory of the hooks 62 of the anchor 9 that cause the anchor 9 to move along a deeper curve into the tissue, thereby causing the pulling effect as described.

The curvature of the tips 160' that prevents contact between the pointed ends of the tips 160' and an inner surface of the container tube may be best described as follows. In the folded configuration of FIG. 49B the hooks 62 have a first curve portion extending towards a central axis of the anchor 9. The hooks 62 and the tips 160 then have a second curve portion that extends away from a central axis of the anchor 9. Finally, there is a third curve portion where the tips 160' curve back towards a central axis of the anchor 9 such that the pointed ends of the tips 160' are angled away from the inner surface of the container tube applying the constraining force. As such the curvature of the hooks 62 display at least one point of inflection. In other words, the curvature of the tips 160 and/or hooks 62 may be described as at least one of a reverse curvature, an opposite curvature or a sigmoid curvature.

When in the unfolded configuration, as shown in FIG. 50B, the hooks 64 extend away from the central axis of the anchor 9 in a grappling hook type shape. In the unfolded configuration the hooks have a curvature with at least one point of inflection, and the direction of curvature of the hook reverses at the tip 160', with a different shape to the alternative curvature used for the anchor 9 of FIG. 50A, as can be seen by comparison of the encircled part of FIGS. 50A and 50B.

As may also be seen in FIGS. 50A and 50B, the hooks 62 of the anchor 9 shown in the unfolded configuration of FIG. 50B cover a larger planar extent than the hooks 62 of the anchor 9 shown in the unfolded configuration of FIG. 50A. By requiring that the tips 160' are curved as described above when unfolded, the surface area covered by the unfolded anchor 9 is increased. This spreads the force applied by the anchor 9 across the body tissue it is to be implanted in across a larger area and thus reduces the strain on the tissue during implantation of the anchor.

As shown in FIGS. 49A, 49B, 50A and 50B, the tips 160, 160' may be shaped such that the widest part of the tip 160, 160' is wider than a preceding portion of the hooks 62. When tissue regrowth occurs around the anchor 9 once it has been implanted, the tissue may regrow around the hook 62 which extends through the body tissue. As the widest part of the tips 160, 160' is wider than the preceding portion of the hook 62, more force is required to remove the implanted anchor 9. This beneficially reinforces the implantation of the anchor 9.

The shape of the tips 160, 160' may be described as that of a teardrop, a leaf or a petal. That is, the tips 160, 160' comprise a generally ovate shaped body which has a pointed end for engaging the body tissue during implantation of the anchor 9. The ovate body is preferably adjacent to the hooks 62, with the pointed end at a distal end of the anchor 9.

Whilst the shape of the tips 160, 160' is shown in FIGS. 49A, 49B, 50A and 50B as described above, the tips 160, 160' may instead comprise a taper extending from the hooks 62 to the end of the tips 160, 160'.

Although not shown in FIGS. 49A, 49B, 50A and 50B, the anchor 9 may comprise any of the other features suitable for the anchor 9 discussed herein. For example, the openings 64 need not be limited to the openings 64 shown in the Figures. Moreover, the base 109 of the anchor 9 may comprise a locking segment 28 as discussed herein.

Figure 51:
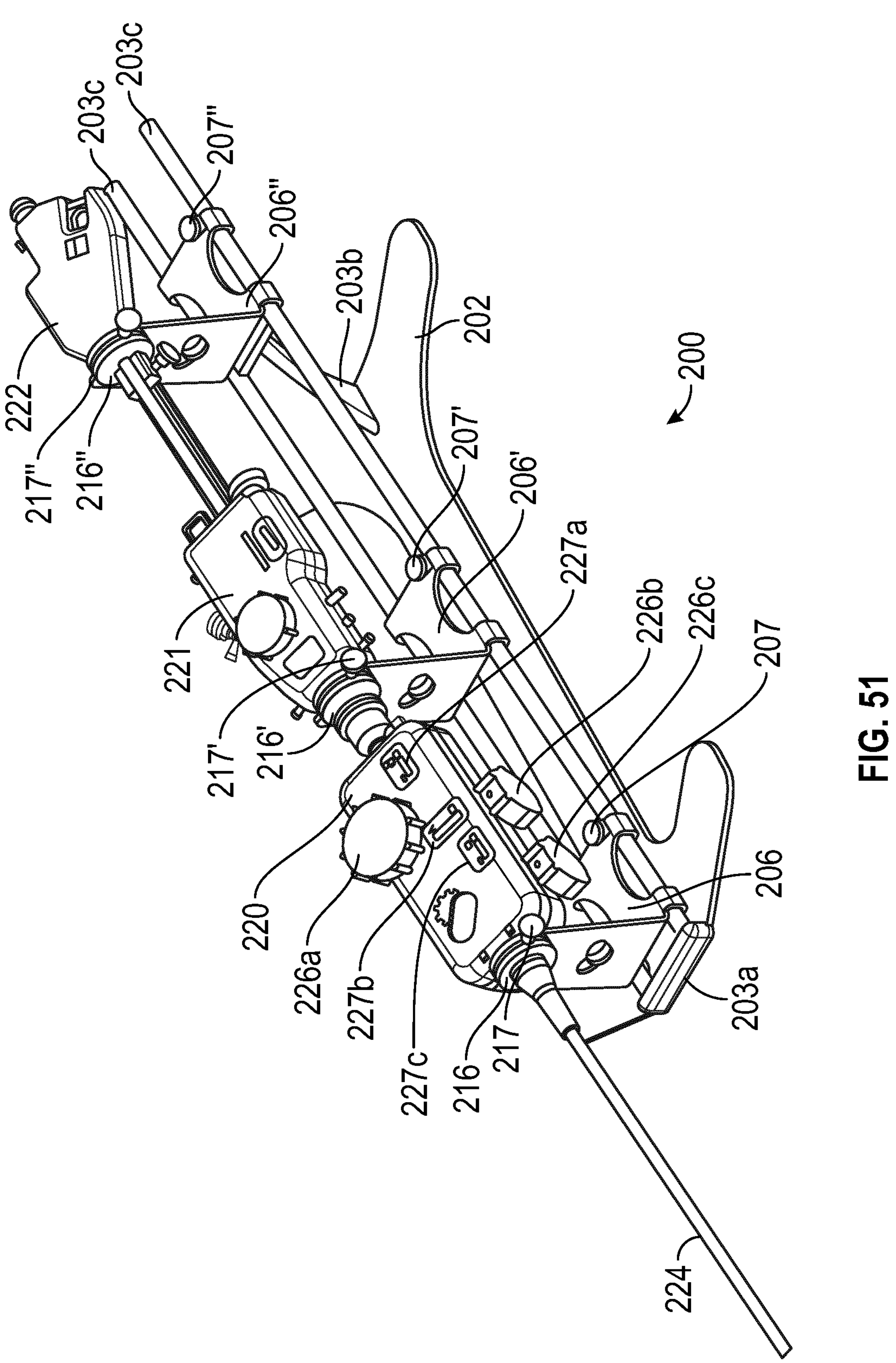
FIG. 51 shows a device handle capable of operating the catheter device.

FIG. 51 displays a device handle 200 for operating and controlling the catheter device 2 as well as a steerable introducer (not shown) for the catheter device. The device handle 200 comprises a rack 202, on which one or more rack wagons 206, 206', 206" may be mounted. The rack wagons 206, 206', 206" provide a number of supports to which one or more operating handles 220, 221, 222 may be mounted. The operating handles 220, 221, 222 in turn are used to actuate one or more pullwires housed within a pullwire sheath 224 of the catheter device 2, to control the functionality of the catheter device 2 as described above. The pullwire sheath 224 may be a catheter, such as a 24 French catheter or any other size suitable for use with the catheter device. The pullwires disposed within the pullwire sheath 224 may be disposed through the walls of the pullwire sheath 224, or along its centre, as required for the desired functionality of the pullwires. The pullwire sheath 224 may be steerable and thus may be a steerable catheter.

The rack 202 shown in FIG. 51 comprises a base structure to which at least two supports are mounted. A first support 203*a* is located at a distal end of the rack 202, whilst a second support 203*b* is located at a proximal end of the rack 202. The supports 203*a*, 203*b* provide a mounting surface for a rail 203*c*. Whilst the second support 203*b* is seen to be at a greater raised height from the surface of the rack 202 than the first support 203*a*, it will be readily understood that various support shapes and structures may be utilised to provide the mounting surface for the rail 203*c*. The rail 203*c* provides a support structure to which the rack wagons 206, 206', 206" may be slidably mounted to. It will be readily appreciated that a number of suitable arrangements of the rack 202 may be implemented in the device handle 200 of the catheter device 2. For example, the rack 202 may comprise more than two supports 203*a*, 203*b*, and the rail 203*c* may take on a number of configurations as long as the rack wagons 206, 206', 206" may be slidably mounted on the rail 203*c*.

Whilst three rack wagons 206, 206', 206" are shown in FIG. 51, any number of rack wagons 206, 206', 206" may be utilised in the device handle 200 as appropriate. Focusing now on a single rack wagon 206, the rack wagon 206 is formed from a single piece of sheet metal. The rack wagon 206 comprises a bent shape, with a first portion of the rack wagon 206 being perpendicular to a second portion of the rack wagon 206. The first rack portion may lie in a plane parallel to that of the rail 203*c*, and comprise a number of legs which allow the rack wagon 206 to be slidably mounted onto the rail 203*c*. A thumb screw 207 may then be used to clamp the rack wagon 206 to the rail 203*c*, to prevent the rack wagon 206 from moving from its desired position. Thus during assembly (and vice versa for disassembly) of the delivery handle 200 shown in FIG. 51, the rack wagons 206, 206', 206" may be slid on to the rail 203*c* from the proximal end of the rack 202. Thumb screws 207, 207', 207" are then tightened to clamp the rack wagons 206, 206', 206" at their respective locations. Advantageously, this allows the rack wagons 206, 206', 206" to be mounted and/or removed from the rack 202 without using any specialised tools. The components of the device handle 200 may then be taken for sterilisation following any operation or procedure with relative ease.

Still with reference to a single rack wagon 206, a second portion of the single piece of sheet metal may be perpendicular to the first portion. The second portion may comprise, at its end furthest from the bend in the rack wagon 206, a slot of semi-circular, ovoid or any other suitable cross section to which a number of clamping devices may be attached. The second portion of the rack wagon 206 may also comprise a flange disposed adjacent the slot, the flange configured to receive a thumb screw 217. The clamping devices may comprise a number of washers, O-rings and/or clamps which themselves provide support for the pullwire sheath 224 and the operating handles 220, 221, 222. In addition to or as an alternative to the washers, O-rings and/or clamps, a number of discs 216, 216', 216" comprising round grooves may be disposed around the pullwire sheath 224 and positioned on the slot of the respective rack wagon 206, 206', 206". A thumb screw 217, 217', 217" may be passed through the flange of each rack wagon 206, 206', 206" to constrain the rotation of each disc 217, 217', 217" and thus constrain rotation of the pullwire sheath 224 if needed.

Turning now to the operating handles 220, 221 and 222 shown in FIG. 51, a number of spacers and washers, O-rings and/or clamps keep the operating handles 220, 221, 222 in their desired positions rigidly along the pullwire sheath 224. The spacers and washers, O-rings and/or clamps may themselves also be disposed about the pullwire sheath 224. Whilst three delivery handles 220, 221, 222 are shown mounted to the delivery handle 200, it will be readily appreciated that any number of delivery handles 220, 221, 222 may be mounted in the delivery handle 200 to achieve the desired operation of the catheter device 2 and the associated introducer.

Focusing on the operating handle 220 shown mounted between the first rack wagon 206 and the second rack wagon 206', the operating handle 220 may comprise a number of gears and/or dials 226*a*, 226*b*, 226*c*. Each gear and/or dial 226*a*, 226*b*, 226*c* may control the actuation of a pullwire disposed in the pullwire sheath 224. The operating handle 220 is used to control the steering action of the steerable introducer, for example with the pullwire actuated by any one of the gears and/or dials 226*a*, 226*b*, 226*c* being a part of a steering control mechanism or a twisting control mechanism for the steerable introducer.

The arrangement of the operating handles 220, 221, 222 can be changed to suit the user preference and to align with a desired procedure. For example, instead of control of wires for the steerable introducer, the pullwire actuated by any one of the gears and/or dials 226*a*, 226*b*, 226*c* could be, but not limited to, the pullwire 204 operating the hinge element 104 of the catheter device 2, and so on. Similarly, the gears, dials and other control inputs for the operating handles 221 and 222 may control various elements of the catheter device 2. In one arrangement, the proximal operating handle 220 controls the steerable introducer as well as advancement of the catheter device 2, the middle operating handle 221 controls various functions of the catheter device 2 relating to grasping the leaflet and implantation of the leaflet anchor, and the proximal operating handle 222 controls further operations linked to implantation of the artificial chord 14, such as adjustment and/or cutting of the chord 14. In addition, the relative location of the operating handles 220, 221, 222 on their respective rack wagons 206, 206', 206" can be varied to move elements of the device at the distal end of the 24 French 224, for example sliding of the proximal rack wagon 206" may advance the papillary anchor 9 and thereby implant it into the papillary muscle.

To indicate the amount of tension and/or deflection applied to each pullwire controlled by the gears and/or dials 226*a*, 226*b*, 226*c* of the catheter device, a number of indicators 227*a*, 227*b*, 227*c* may also be disposed on an outer surface of the operating handle 220. These may be used as feedback indicators to indicate to the operator of the catheter device 2 how much tension is currently applied to the pullwires, along with their current behaviour/positioning. The indicators 227*a*, 227*b*, 227*c* may be used in addition to and/or alternatively to the various clutch configurations discussed above.

Whilst the functionality of the operating handle has only been discussed in relation to a single operating handle 220, it will be readily understood that some or all of the features discussed herein may be applied to the other operating handles 221, 222 of the delivery handle 200.

Figure 52A:
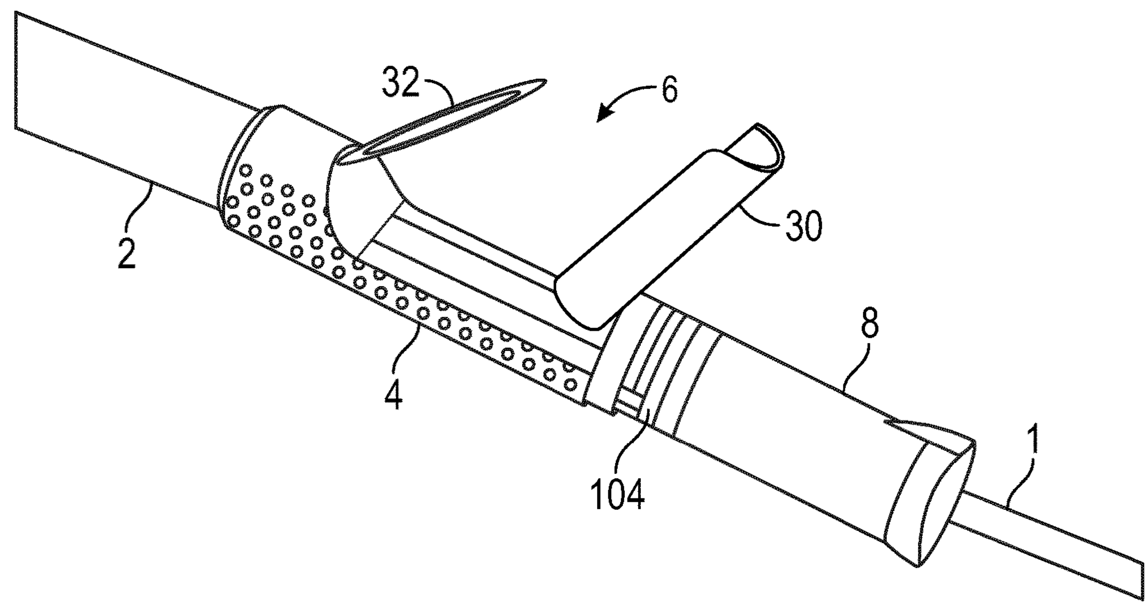
Figure 52B:
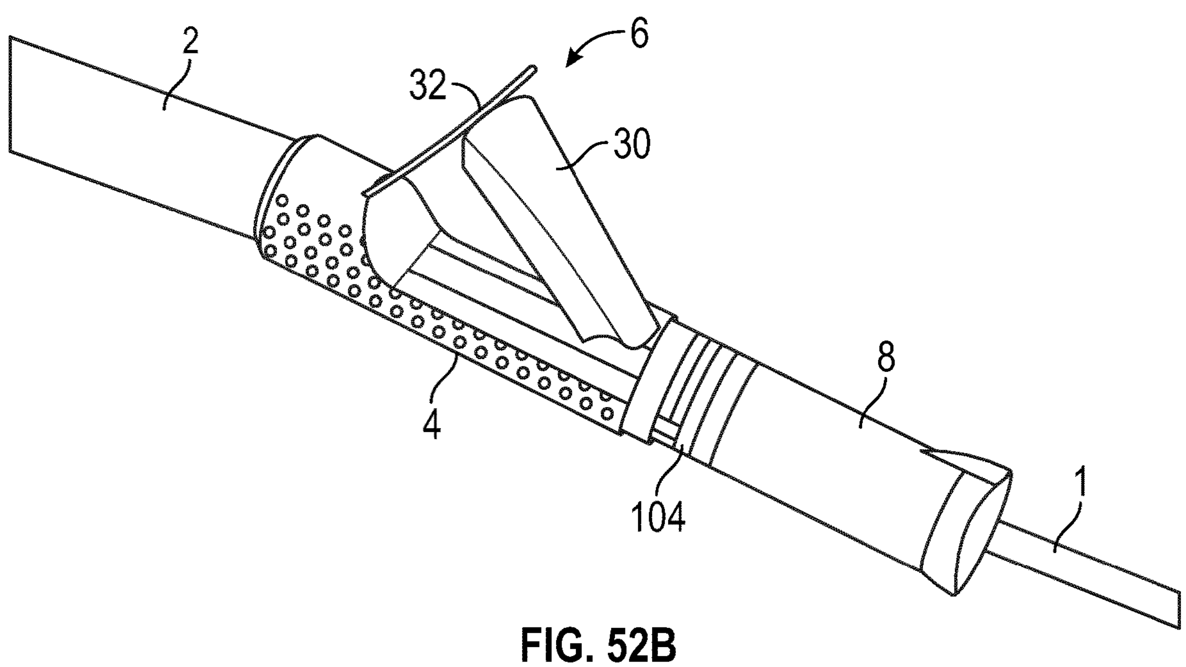
FIG. 52B shows the two gripper arms of the gripper device closed together.

FIGS. 52A and 52B show the main body of the catheter device 2. The main body comprises a proximal part 4 and a distal part 8, the two parts connected to one another at the hinge element 104. The distal part 4 may house the papillary anchor 9 as discussed above and as shown in the previous Figures. The hinge element 104 may operate as discussed above with reference to the flexible joint and as shown in the previous Figures. A guide wire 1 runs through the catheter device 2 and extends out of the distal part 8. The main body of the catheter device 2 may be formed of a composite material, for example glass reinforced PEEK, or carbon reinforced PEEK. The proximal part 4 of the catheter device 2 may be joined to a steerable catheter of the catheter device 2 by reflowing polymer at the location of the joint.

Focusing on the proximal part 4 of the catheter device 2, the mechanical gripper device 6 may be seen. The mechanical gripper device 6 comprises a first gripper arm 30 and a second gripper arm 32, with the mechanical gripper device 6 being in accordance with one of the embodiments previously discussed. FIG. 52A shows the first gripper arm 30 and the second gripper arm 32 moved away from a main body of the catheter device 2. The mechanical gripper device 6 may be configured such that the first gripper arm 30 moves to meet the second gripper arm 32. The first gripper arm 30 may be moved until a contact is made between the two arms 30, 32. With the second gripper arm 32 configured to be placed on top of a leaflet 10 to suppress its motion, the first gripper arm 30 may then be rotatably moved back in to the proximal part 4 of the main body of the catheter device 2. As it does so, the first gripper arm 30 is able to grasp the restrained leaflet 10 between itself and the main body of the catheter device 2. The leaflet anchor 10 may be housed within the first gripper arm 30 in accordance with any of the embodiments discussed above.

As shown in FIGS. 52A and 52B, the second gripper arm 32 may be a leaflet motion suppressor 32 comprising a loop of wire. The wire may be made of a suitably elastic material, for example nitinol or stainless steel. Thus, when the leaflet motion suppressor 32 is not housed within the main body of the catheter device 2, it is in an undeformed state. The elasticity of the leaflet motion suppressor 32 allows the leaflet motion suppressor 32 to suppress the motion of the leaflet 10 during a cardiac cycle, whilst allowing the first gripper arm 30 to contact the leaflet motion suppressor 32 without damaging the leaflet 10 restrained between the two arms 30, 32. The elasticity of the leaflet motion suppressor 32 allows the leaflet motion suppressor 32 to curve as shown in FIG. 52B when it comes into contact with the first gripper arm 30, thus helping to avoid any pinching of the leaflet 10 which may result in damage of the leaflet 10 as it is restrained.

The leaflet motion suppressor 32 may be housed within a lumen (not shown) of the catheter device 2. When housed within the lumen, the leaflet motion suppressor 32 comprises an elastically deformed state. The lumen may run parallel to a main axis of the catheter device 2, before angling to meet a surface of the proximal part 4 proximal the location of the mechanical gripper device 6. The lumen may be angled such that the leaflet motion suppressor is angled as shown in FIGS. 52A and 52B.

The loop formed in the loop of wire may prevent the leaflet motion suppressor 32 from being fully withdrawn into the catheter device 2. For example, the end of the lumen may feature a pin extending across an opening of the lumen, located at the surface of the proximal part 4. The loop of the wire may engage the pin when it is slidably moved into the catheter device, thus preventing the leaflet motion suppressor 32 from being withdrawn any further into the catheter device 2. The loop of the wire may therefore move from a location flush with the outside surface of the proximal part 4 to a position away from the main body of the catheter device 2, as shown in FIGS. 52A and 52B.

Figures 53A, 53B, 53C, 54A, 54B, 54C, 55A, 55B, 55C:
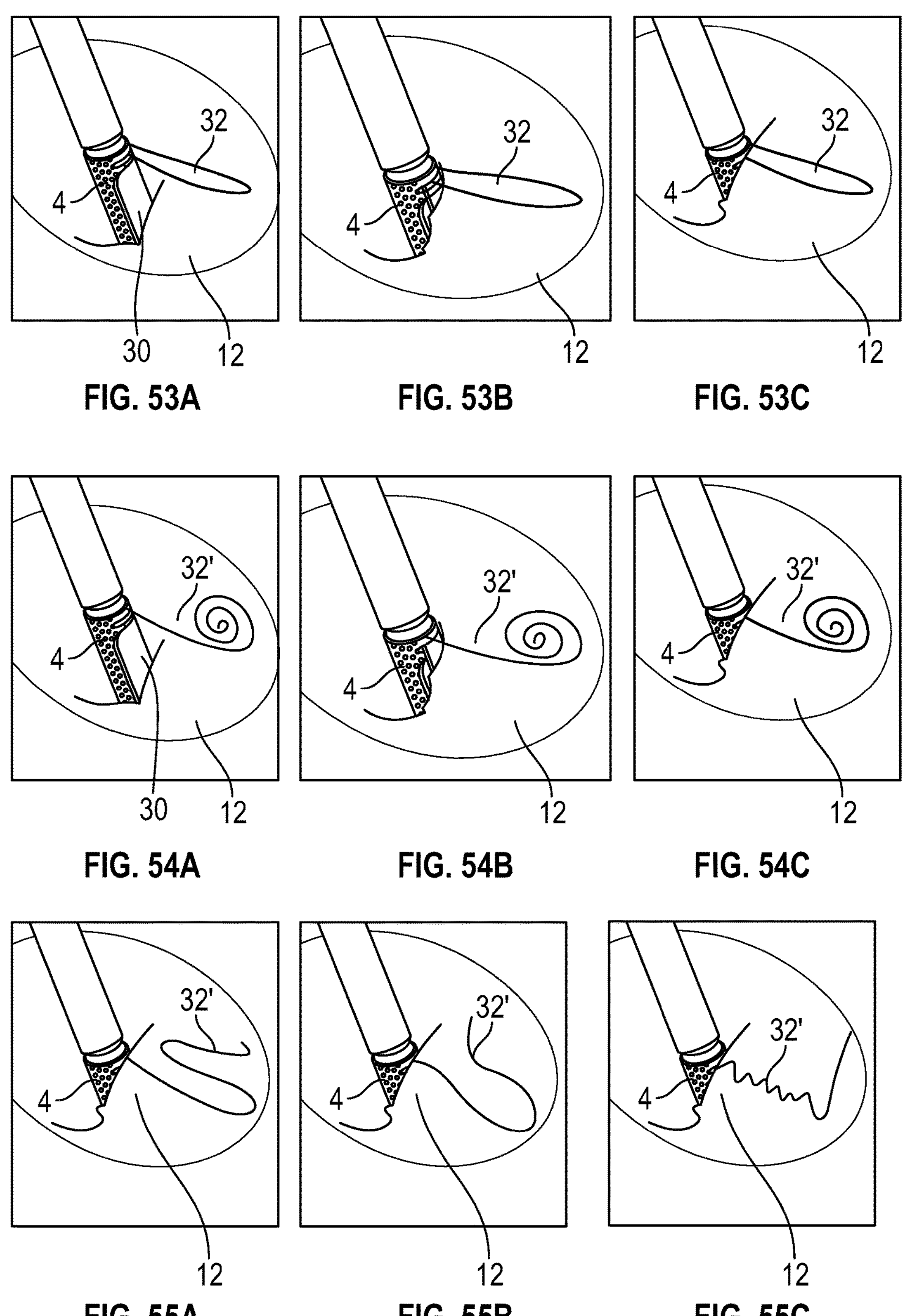
FIGS. 53A and 54A show the gripper device passing through a model leaflet valve with the leaflet motion suppressor above the leaflet and the first gripper arm grasping from below (not shown)
FIGS. 53B and 54B show the gripper device passing under the leaflet valve with the leaflet motion suppressor still above the leaflet and the first gripper arm grasping from below (not shown)
FIGS. 53C and 54C show the gripper device grasping the leaflet, with the leaflet motion suppressor grasping the leaflet from above and the second arm grasping from below (not shown)
FIGS. 55A, 55B and 55C show alternative arrangements suitable for the leaflet motion suppressor.

FIGS. 53A, 53B and 53C show the leaflet motion suppressor 32 engaging with a leaflet 12 of a model mitral valve at various stages of its operation. For example, the catheter device 2 may approach the mitral valve from a top-down approach (i.e. from the left atrium into the left ventricle). As shown in FIG. 53A, the leaflet motion suppressor 32 is slid out of its lumen, engaging with a top surface of the leaflet 12. The loop extends over a suitably large distance such that there is sufficient contact between the leaflet 12 and the leaflet motion suppressor 32. The first gripper arm 30 remains closed. The catheter device 2 is then moved down through the mitral valve before the first gripper arm 20 is rotated outwards, away from the main body of the catheter device 2, as shown in FIG. 53B. Finally, the first gripper arm 30 may be moved towards the leaflet motion suppressor 32, such that the leaflet 12 is firmly restrained by the mechanical gripper device 6 via a contact force between the leaflet motion suppressor 32 and the first gripper arm 30. The contact may be a slidable contact, such that the first gripper arm 30 may then rotate back towards the main body of the catheter device 2 with the leaflet 10 still being restrained, before the leaflet is then grasped between the first gripper arm 30 and the main body of the catheter device 2, in the mechanical gripper device 6. The leaflet anchor 10 (as in the prior Figures) may then be deployed and implanted in the leaflet 12, with the motion of the leaflet 12 suppressed during the gripping motion.

Whilst FIGS. 53A, 53B and 53C show the leaflet motion suppressor 32 comprising a loop of wire, the leaflet motion suppressor 32 may comprise a number of shapes and/or arrangements to achieve its objective function. For example, FIGS. 54A, 54B and 54C show an alternative embodiment of the leaflet motion suppressor 32' comprising an open-ended piece of wire, an end of the wire being located outside of the main body of the catheter device 2. The over-arching principle of the leaflet motion suppressor 32' shown in FIGS. 54A, 54B and 54C is aligned with that of the leaflet motion suppressor 32 as shown in FIGS. 53A, 54B and 54C respectively, as described above.

To prevent the leaflet motion suppressor 32' comprising a single piece of wire from being completely withdrawn into the catheter device 2 as it is slidably moved back into the lumen which houses it, a wire stopper (not shown) may be disposed at the end of the wire located outside the main body of the catheter device 2. It will be appreciated that the wire stopper will need to be of a shape suitably larger than the opening formed by the lumen, such that the wire stopper is incapable of being housed within the lumen.

As the leaflet motion suppressor 32' is withdrawn into the lumen, the leaflet motion suppressor 32' will elastically deform from its undeformed state to its elastically deformed state. For example, the wire may straighten and may comprise the shape of the lumen it is housed within.

The leaflet motion suppressor 32' shown in FIGS. 54A, 54B and 54C comprises a spiral shape towards the end of the wire. The spiral shape provides a larger surface area for engagement with the leaflet 12. Additionally, the end of the wire may be located at the centre of the spiral shape. This encloses the end of the wire, such that it is less likely that the end of the wire may pierce and/or damage the tissue that it contacts. The spiral shape may be described as a pig-tail shape. When a constraining force is applied (i.e. by the internal walls of the lumen), the wire may straighten but when the constraining force is removed (i.e. the wire is moved out of the lumen, the end of the wire moving away from the main body of the catheter device), the wire may coil into the spiral shape shown in the Figures.

FIGS. 55A, 55B and 55C show alternative arrangements for the leaflet motion suppressor 32', each arrangement capable of being implemented similarly to the examples discussed above. As shown in the Figures, the leaflet motion suppressor 32' may comprise a number of bends and/or curves which increase its effective surface area of engagement with the leaflet 12. In its undeformed state the piece of wire displays the bends and/or curves it is formed with. However, when withdrawn into the lumen, it will be understood that the elastic wire deforms and straightens out, taking on a shape which complements the structure of the lumen. The leaflet motion suppressor 32' comprising an open-ended wire, as shown in FIGS. 54A to 55C may comprise a soft tip at the end of the wire to decrease the likelihood of the wire piercing and/or damaging the surrounding tissue, such as the leaflet 12.

The wire component of the leaflet motion suppressor 32, 32' may be an off-the shelf wire, such as a guide wire, readily available for use in cardiac interventions. Accordingly, an operator of the catheter device 2 can then choose a wire that they find appropriate for suppressing motion of the leaflet 12 during an operation. In other words, different wires of an identical predefined size may be implemented with different stiffness and/or tip structure (i.e. bends, curves and/or loops) as desired. For example, if a first wire did not function as desired, a second wire having similar or different characteristics may be used. As such, the leaflet motion suppressor 32, 32' may not be stored within the lumen of the catheter device 2, but may be selected from a storage device and inserted into a port of the catheter device 2 during a particularly challenging insertion of a leaflet anchor 10 into a leaflet 12.

The invention claimed is:

1. A catheter device for implanting a leaflet anchor during a procedure for implanting an artificial chordae line into a heart, the catheter device comprising:

a leaflet anchor for attachment to a leaflet of the heart; and a leaflet anchor deployment mechanism for deploying the leaflet anchor;

wherein the leaflet anchor deployment mechanism allows for retraction and repositioning of the leaflet anchor after deployment of the leaflet anchor into the leaflet via an ejector unit having a grasping device with a first configuration arranged to permit deployment of the leaflet anchor into the leaflet without disengagement of the leaflet anchor from the ejector unit, and a second configuration in which the leaflet anchor is reversibly released from the ejector unit;

wherein in the first configuration the grasping device of the ejector unit grasps a proximal end of the leaflet anchor, whilst a distal end of the leaflet anchor is unimpeded by the grasping device to enable it to be implanted in the leaflet; and wherein in the second configuration the grasping device of the ejector unit is disengaged from the leaflet anchor.

2. The catheter device as claimed in claim 1, wherein the leaflet anchor is formed from a flexible material with a hooked shape in an unfolded configuration and is arranged to deform elastically into a folded configuration when constrained by the leaflet anchor deployment mechanism.

3. The catheter device as claimed in claim 1, wherein prior to deployment the ejector unit is placed within the leaflet anchor deployment mechanism inboard of the leaflet anchor and when the ejector unit and leaflet anchor are within the leaflet anchor deployment mechanism the ejector unit holds the leaflet anchor with the grasping device in the first configuration.

4. The catheter device as claimed in claim 1, wherein the grasping device is arranged to remain in the first configuration during deployment of the leaflet anchor, with the ejector unit being arranged so that it cannot move to the second configuration until after the leaflet anchor is implanted.

5. The catheter device as claimed in claim 1, wherein the leaflet anchor and the ejector unit are housed inside a leaflet anchor tube of the leaflet anchor deployment mechanism prior to deployment, with the ejector unit further inside the leaflet anchor tube than the leaflet anchor.

6. The catheter device as claimed in claim 5, wherein the leaflet anchor tube has an opening that can be directed toward the leaflet, with the opening of the leaflet anchor tube being directed toward the proximal end of the catheter device, in order that the leaflet anchor is insertable through the leaflet from a bottom of the leaflet.

7. The catheter device as claimed in claim 5, wherein the leaflet anchor is arranged to be deployed by advancing both the leaflet anchor and the ejector unit along the leaflet anchor tube, with the leaflet anchor having pins at its distal end that form into hooks of a hooked shape as the pins leave an opening of the leaflet anchor tube.

8. The catheter device as claimed in claim 5, wherein a change from the first configuration of the ejector unit to the second configuration of the ejector unit is actuated by movement of the ejector unit along the leaflet anchor tube, and wherein the grasping device is permitted to open when the ejector unit reaches a certain position in the leaflet anchor tube.

9. The catheter device as claimed in claim 5, wherein the ejector unit has a constrained configuration as the first configuration, and a non-constrained configuration as the second configuration, and wherein the catheter device is arranged so that a transition from the first configuration to the second configuration occurs by movement of the ejector unit to a point at which a constraint from walls of the leaflet anchor tube is removed, so that the grasping device opens.

10. The catheter device as claimed in claim 5, wherein the grasping device comprises two or more grappling hooks arranged to engage with the leaflet anchor at their ends when in the first configuration, and wherein the grasping device is arranged to engage and disengage from the leaflet anchor via a radial movement of the grappling hooks relative to the leaflet anchor tube.

11. The catheter device as claimed in claim 5, comprising a groove in a wall of the leaflet anchor tube for guiding the ejector unit via a guide pin on the ejector unit.

12. The catheter device as claimed in claim 11, including a narrowing in the groove for acting as an indicator to let an operator know when the ejector unit has reached a certain position, wherein a size of the guide pin and a width of the narrowing are set so that engagement of the guide pin with the narrowing in the groove will require an increased force before further movement of the guide pin along the groove can be made.

13. The catheter device as claimed in claim 12, wherein the narrowing is provided in order to signify that the leaflet anchor has been moved to a deployed position, whilst the ejector unit remains in the first configuration, and to inform an operator that once the ejector unit is pushed further then the ejector unit will move to the second configuration.

14. The catheter device as claimed in claim 1, wherein the leaflet anchor deployment mechanism includes a line pusher for directing a line out of and away from the leaflet anchor deployment mechanism during deployment of the leaflet anchor.

15. The catheter device as claimed in claim 14, wherein the line pusher is arranged to be actuated during deployment of the leaflet anchor and when the leaflet anchor is released from the ejector unit.

16. The catheter device as claimed in claim 14, wherein the line pusher is arranged to transition from a constrained state to a non-constrained state with a radially outward movement to push the line out, with this radially outward movement being permitted once a constraint is removed.

17. The catheter device as claimed in claim 16, wherein the constraint on the line pusher is from the leaflet anchor.

18. The catheter device as claimed in claim 1, comprising:

a two-part housing section extending from a distal end of the catheter device along a length of the catheter device toward the proximal end of the catheter device, the two-part housing section being arranged to be placed between a papillary muscle and the leaflet of the heart during use of the catheter device, and the two-part housing section comprising a distal part at the distal end of the catheter device and a proximal part located on a proximal side of the distal part;

the leaflet anchor deployment mechanism being at the proximal part of the two-part housing section;

a papillary anchor deployment mechanism at the distal part of the two-part housing section for deployment of a papillary anchor for attachment to the papillary muscle, wherein the papillary anchor deployment mechanism is arranged for deployment of the papillary anchor by moving it outward in a distal direction relative to the distal part; and a flexible joint located between the proximal part and the distal part of the two-part housing section, wherein the flexible joint allows a centreline of the distal part to be angled relative to a centreline of the proximal part.

19. The catheter device as claimed in claim 1, wherein the leaflet anchor deployment mechanism comprises a mechanical gripper device for grasping the leaflet of a heart valve, wherein the mechanical gripper device comprises a leaflet anchor tube for housing the leaflet anchor in a folded configuration; the mechanical gripper device and leaflet anchor being arranged such that when, in use, the mechanical gripper device grasps the leaflet, the leaflet anchor can be pushed out of the leaflet anchor tube to pierce the leaflet and form the leaflet anchor into an unfolded configuration so that hooked formations of the leaflet anchor can, in use, secure the leaflet anchor in the leaflet; wherein the mechanical gripper device includes a first gripper arm rotatably coupled to a main body of the catheter device so that the first gripper arm can rotate relative to the catheter device to move an outer end of the first gripper arm away from the main body of the catheter device and a second gripper arm rotatably and/or slideably coupled to the main body of the catheter device so that the second gripper arm can rotate and/or slide relative to the main body of the catheter device to move an outer end of the second gripper arm away from the main body of the catheter device; and wherein the first and second gripper arms are arranged so that they can move to come into contact with one another at a point spaced apart from the main body of the catheter device.

20. The catheter device as claimed in claim 1, wherein the leaflet anchor comprises a number of hooks for engagement with body tissue and having a folded position and an unfolded position, wherein the leaflet anchor is made of an elastic material such that it can be elastically deformed into the folded position by application of a constraining force, and will return to the unfolded position when no constraining force is applied, and wherein the hooks are formed with openings along their length.

21. A method of use of the catheter device of claim 1 for implanting a leaflet anchor into the heart during a procedure for implanting an artificial chordae line, the method comprising:

deployment of the leaflet anchor into the leaflet using the leaflet anchor deployment mechanism with the ejector unit initially remaining in its first configuration; and later movement of the ejector unit into the second configuration to thereby release the leaflet anchor.

22. The method of use of the catheter device as claimed in claim 21, further comprising:

testing a connection of the leaflet anchor before moving the ejector unit from the first configuration to the second configuration.

23. A method of manufacture of the ejector unit for the catheter device of claim 1, the method comprising:

forming tines into an elastic metal tube via cutting; and deforming an end of the tines with heat setting in order to form a hooked configuration.

24. The catheter device as claimed in claim 5, wherein the grasping device of the ejector unit grips the leaflet anchor and can advance along the leaflet anchor tube from a fully stowed position to the first configuration, wherein the grasping device is capable of moving back to the first configuration from the second configuration so that the grasping device reengages with the leaflet anchor and deployment of the leaflet anchor can be reversed.

25. The catheter device as claimed in claim 1, wherein the leaflet anchor secures the artificial chordae line into the heart.

26. The catheter device as claimed in claim 1, wherein leaflet anchor is fully released from the ejector unit in the second configuration.

* * * * *